United States Patent
Shi et al.

(10) Patent No.: US 9,101,655 B2
(45) Date of Patent: *Aug. 11, 2015

(54) METHODS AND COMPOSITIONS FOR TREATING MAMMALIAN NERVE TISSUE INJURIES

(71) Applicant: PURDUE RESEARCH FOUNDATION, West Lafayette, IN (US)

(72) Inventors: Riyi Shi, West Lafayette, IN (US); Richard B. Borgens, Delphi, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/912,499

(22) Filed: Jun. 7, 2013

(65) Prior Publication Data
US 2014/0100289 A1    Apr. 10, 2014

Related U.S. Application Data

(63) Continuation of application No. 12/508,184, filed on Jul. 23, 2009, now Pat. No. 8,460,646, which is a continuation-in-part of application No. 09/438,206, filed on Nov. 12, 1999, now Pat. No. 7,582,680, said
(Continued)

(51) Int. Cl.
*A61K 31/765* (2006.01)
*A61K 31/77* (2006.01)
(Continued)

(52) U.S. Cl.
CPC ............... *A61K 31/765* (2013.01); *A61K 31/00* (2013.01); *A61K 31/74* (2013.01); *A61K 31/77* (2013.01)

(58) Field of Classification Search
CPC ...... A61K 31/00; A61K 31/74; A61K 31/765; A61K 31/77; A61K 2300/00
USPC ......................... 424/78.08; 514/715, 724, 738
See application file for complete search history.

(56) References Cited

U.S. PATENT DOCUMENTS 4,369,769 A    1/1983    Edwards
4,599,354 A    7/1986    Shulman
(Continued)

FOREIGN PATENT DOCUMENTS

EP    04 84 186 A1    5/1992
EP    04 84 186 B1    12/1999
(Continued)

OTHER PUBLICATIONS

Adams-Graves et al., "RheothRx (poloxamer 188) injection for the acute painful episode of sickle cell disease: a pilot study," *Blood*, Sep. 1, 1997; 90(5):2041-6.
(Continued)

*Primary Examiner* — Blessing M Fubara
(74) *Attorney, Agent, or Firm* — Mueting, Raasch & Gebhardt, P.A.

(57) ABSTRACT

To achieve, an in vivo repair of injured mammalian nerve tissue, an effective amount of a biomembrane fusion agent is administered to the injured nerve tissue. The application of the biomembrane fusion agent may be performed by directly contacting the agent with the nerve tissue at the site of the injury. Alternatively, the biomembrane fusion agent is delivered to the site of the injury through the blood supply after administration of the biomembrane fusion agent to the patient. The administration is preferably by parenteral administration including intravascular, intramuscular, subcutaneous, or intraperitoneal injection of an effective quantity of the biomembrane fusion agent so that an effective amount is delivered to the site of the nerve tissue injury.

14 Claims, 34 Drawing Sheets

Related U.S. Application Data application No. 12/508,184 is a continuation of application No. 10/132,542, filed on Apr. 24, 2002, now Pat. No. 7,837,987.

(60) Provisional application No. 60/108,145, filed on Nov. 12, 1998, provisional application No. 60/286,200, filed on Apr. 24, 2001.

(51) Int. Cl.
*A61K 31/74* (2006.01)
*A61K 31/00* (2006.01)

(56) References Cited

U.S. PATENT DOCUMENTS

| | | | |
|---|---|---|---|
| 4,919,140 | A | 4/1990 | Borgens et al. |
| 5,346,903 | A | 9/1994 | Ackerman et al. |
| 5,382,584 | A | 1/1995 | Balasubramanian |
| 5,470,568 | A | 11/1995 | Lee |
| 5,523,492 | A | 6/1996 | Emanuele |
| 5,545,648 | A | 8/1996 | Hansebout et al. |
| 5,605,687 | A | 2/1997 | Lee |
| 6,090,823 | A | 7/2000 | Ishikawa |
| 6,432,434 | B1 | 8/2002 | Meyerhoff et al. |
| 6,440,455 | B1 | 8/2002 | Benowitz |
| 6,495,532 | B1 | 12/2002 | Bathurst et al. |
| 6,858,409 | B1 | 2/2005 | Thompson et al. |
| 7,199,110 | B2 | 4/2007 | Borgens et al. |
| 7,582,680 | B1 * | 9/2009 | Shi et al. ............ 514/723 |
| 7,837,987 | B2 * | 11/2010 | Shi et al. ............ 424/78.37 |
| 8,460,646 | B2 * | 6/2013 | Shi et al. ............ 424/78.08 |
| 2003/0118545 | A1 | 6/2003 | Shi et al. |
| 2004/0214790 | A1 | 10/2004 | Borgens |
| 2005/0069520 | A1 | 3/2005 | Shi et al. |

FOREIGN PATENT DOCUMENTS

| | | |
|---|---|---|
| WO | WO 97/35577 A1 | 10/1997 |
| WO | WO 02/092107 A1 | 11/2002 |
| WO | WO 2004/060146 A2 | 7/2004 |
| WO | WO 2004/060146 A3 | 3/2005 |

OTHER PUBLICATIONS

Ahkong et al., "Movements of fluorescent probes in the mechanism of cell fusion induced by poly(ethylene glycol)," *J. Cell Sci.*, 1987; 88:389-98.

Aldewinckel et al., "Effects of Poly (Ethylene Glycol) on Liposomes and Erythrocytes permeability changes and membrane fusion," *Biochim. Biophys. Acta.*, 1982; 689:548-560.

Allen, "Surgery of experimental lesion of spinal cord equivalent to crush injury of fracture dislocation of spinal column," *J. Am. Med. Assoc.*, Sep. 9, 1911; 57:878-880.

Altizer et al. "Endogenous electric current is associated with normal development of the vertebrate limb" *Developmental Dynamics* 2001;221(4):391-401.

Anderson et al., "Characteristics of intraspinal grafts and locomotor function after spinal cord injury," *Proceedings of the Third Altschul Symposium on Neural Cell Specification: Molecular Mechanisms and Neurotherapeutic Implications* (Juurlink et al., eds.,), Plenum Press: New York, NY; 1995. pp. 249-266.

Anderson et al., "Regeneration of spinal neurons in inframammalian vetebrates: morphological and developmental aspects," *J. Hirnforsch.*, 1983; 24:371-398.

Armstrong et al., "Inhibition of red blood cell-inducted platelet aggregation in whole blood by a nonionic surfactant, poloxamer 188 (RheothRx® injection)," *Thrombosis Research*, 1995; 79(5/6):437-50.

Asano et al., "Horseradish peroxidase used to examine the distribution of axonal damage in spinal cord compression injury in vitro," *J. Neurotrauma*, 1995; 12:993 (Abst. No. TS2).

Bajaj, Cahndrjit, "Geometric and solid modeling with algebraic surfaces," Grant Abstract No. 92-22467. Division of Computer and Communication Foundations; National Science Foundation. Project dates Apr. 1, 1993 to Mar. 31, 1997 [retrieved on Aug. 9, 2009]. Retrieved from the Internet: <http://www.nsf.gov/awardsearch/showAward.do?AwardNumber=9222467>; 2 pgs.

Basso et al., "A Sensitive and reliable locomotor rating scale for open field testing in rats," *J. Neurotrauma*, 1995; 12(1):1-21.

Benzel, *Spine Surgery: Techniques, Complication Avoidance and Management*, Philadelphia, PA 1999; cover page, title pages, table of contents and 369-387 and 389-400.

Benzon et al. "The Effect of Polyethylene Glycol on Mammalian Nerve Impulses," *Anesth. Analg.* 1987;66:553-9.

Berne et al. (eds.), "Generation and Conduction of Action Potentials," *Physiology, 3rd Edition*, Mosby: St. Louis, MO; 1993. pp. 36-54.

Bernstein et al., "Spinal cord regeneration: synaptic renewal and neurochemistry," *Neuronal Plasticity*, Cotman, ed., Raven Press, New York, 1978; 49-71.

Bernstein et al., "Synaptic frequency alteration on rat ventral horn neurons in the first segment proximal to spinal cord hemisection: an ultrastructural statistical study of regenerative capacity," *J. Neurocytol.*, 1977; 6:85-102.

Bernstein et al., "Synaptic reorganization following regeneration of goldfish spinal cord," *Exp. Neurol.*, 1973; 41:402-410.

Berry, "Chapter 4: Regeneration in the central nervous system," *Recent Advances in Neuropathology*, Smith et al., eds., Churchill Livingstone, New York, 1979; 67-111.

Bisby, "Regeneration of peripheral nervous system axons," in *The Axon Book* (Waxman et al., eds.), Oxford UP: New York, NY; 1995. pp. 553-578.

Bittner et al. "Reconnection of Severed Nerve Axons With Polyethylene Glycol" *Brain Research*, 1986; 367(351-355).

Bittner, "Long-term survival of anucleate axons and its implications for nerve regeneration," *TINS*, 1991; 14(5):188-193.

Blight et al., "Cutaneus Trunci Muscle Reflex of the Guinea Pig" *The Journal of Comparative Neurology*, 1990; 296:614-633.

Blight, "Delayed demyelination and macrophage invasion: A candidate for secondary cell damage in spinal cord injury," *Central Nervous System Trauma*, 1985; 2(4):299-315.

Blight, "Effect of 4-Aminopyridine on Axonal Conduction-Bloack in Chronic Spinal Cord injury," *Brain Research Bulletin* 1989; 22:47-52.

Blight et al., "The effects of 4-aminopyridine on neurological deficits in chronic cases of traumatic spinal cord injury in dogs: a phase I clinical trial," *J. Neurotrauma*, 1991; 8(2):103-119.

Blight, "Morphometric Analysis of a Model of Spinal Cord Injury in Guinea Pigs, with Behavioral Evidence of Delayed Secondary Pathology," *Journal of the Neurological Sciences* 1991; 103:156-171.

Blight et al., "Morphometric analysis of experimental spinal cord injury in the cat: the relation of injury intensity to survival of myelinated axons," *Neuroscience*, 1986; 19(1):321-341.

Blight, "Remyelination, Revascularation, and Recovery of Function in Experimental Spinal Cord Injury," in *Advances in Neurobiology: Neural Injury and Regeneration*, (Seil, ed.), Raven Press: New York, NY; 1993. vol. 59, pp. 91-104.

Borgens, "Acute Repair of Spinal Injury with Fusogens," Grant Abstract, Grant No. 5R01NS039288-01A1 [online] National Institute of Neurological Disorders and Stroke Project dates Jun. 1, 2000-Feb. 28, 2003. [retrieved on Feb. 23, 2004]. Retrieved from the Internet: 2004 <http://crisp.cit.nih.gov/crisp/CRISP_LIB.getdoc?textkey=6193809&p_grant_num=1R01N>.

Borgens, "Acute Repair of Spinal Injury with Fusogens," Grant Abstract, Grant No. 5R01NS039288-01S1 [online] National Institute of Neurological Disorders and Stroke Project dates Jun. 1, 2000-Feb. 28, 2003. [retrieved on Feb. 28, 2004]. Retrieved from the Internet: 2004 <http://crisp.cit.nih.gov/crisp/CRISP_LIB.getdoc?textkey=6401733&p_grant_num=3R01N>.

Borgens, "Acute Repair of Spinal Injury with Fusogens," Grant Abstract, Grant No. 5R01NS039288-02 [online] National Institute of Neurological Disorders and Stroke. 2001. [retrieved on Feb. 8, 2003]. 2003.

(56) References Cited

OTHER PUBLICATIONS

Borgens, "Acute Repair of Spinal Injury with Fusogens" Grant Abstract, Grant No. 5R01NS039288-03 [online] National Institute of Neurological Disorders and Stroke Project dates Jun. 1, 2000-Feb. 28, 2003. [retrieved on Feb. 8, 2003]. Retrieved from the Internet: 2003 <http://commons.cit.nih.gov/crisp3/crisp_lib.getdoc?textkey=6531108&p_grant_num=5R>.

Borgens, "Acute Treatment of Contusion Injury to the Spinal Cord," Grant Abstract, Grant No. DHHS-R49-CCR-503590-03. (Jun. 16, 1993) [online]. National Center for Injury Prevention and Control [retrieved on Feb. 8, 2003]. 2003.

Borgens, "Acute Treatment of Spinal Trauma by Electrical Fields," Final Report PHS: CDC/CIC #R49/CCR509137. NTIS Item No. PB98155849 (1998) 168 pages.

Borgens, "Chapter 5: Applied Voltages in Spinal Cord Reconstruction: History, Strategies and Behavioural Models," in *Spinal Cord Dysfunction III: Functional Stimulation* (Illis, ed.), Oxford UP: New York, NY: 1992. pp. 110-144.

Borgens et al. "Axonal Regeneration in Spinal Cord Injury: A Perspective and New Technique," *Journal of Comparative Neurology*, 1986; 250:157-167.

Borgens et al., "Behavioral recovery induced by applied electric fields after spinal cord hemisection in guinea pig," *Science*, Oct. 16, 1987; 238:366-369.

Borgens et al., "Behavioral recovery from spinal cord injury following delayed application of polyethylene glycol," *J. Exp. Biol.*, 2002; 205:1-12.

Borgens, "Concept and Innovation: Cellular Engineering: Molecular Repair of Membranes to Rescue Cells of the Damaged Nervous System," *Neurosurgery*, Aug. 2001; 49(2):370-379.

Borgens et al., "Delayed application of direct current fields in experimental spinal cord injuries," *J. Rest. Neurol. Neurosci.*, 1993; 5(5):173-179.

Borgens et al., "Effects of applied electric fields on clinical cases of complete paraplegia in dogs," *J. Rest. Neurol. Neurosci.*, 1993; 5:305-322.

Borgens, "Electrically Mediated Trauma Repair," Grant Abstract, Grant No. DAMD17-94-J-4242 [online] Project dates Aug. 22, 1994-Aug. 21, 1998 [retrieved on Feb. 8, 2003].

Borgens, Richard B. "Electrically Mediated Trauma Repair," Grant No. DAMD17-94-J-4242. Final Report. NTIS Item No. ADA 359272. Sep. 1998. 139 pages.

Borgens, Richard B., "Electronic Facilitation of Functional Recovery Following CNS Trauma," Grant Abstract, Grant No. 9631560 [online]. National Science Foundation, Sep. 15, 1996 to Aug. 31, 1999 [retrieved on Oct. 12, 2002]. Retrieved from the Internet: <URL:https://www.fastlane.nsf.gov/servlet/showaward?award=9631560>; 2 pgs. 2002.

Borgens et al., "Functional recovery after spinal cord hemisection in guinea pigs: The effects of applied electrical fields," *J. Comp. Neurol.*, 1990; 296:634-653.

Borgens et al., "Immediate recovery from spinal cord injury through molecular repair of nerve membranes with polyethylene glycol," *FASEB J.*, Jan. 2000; 14(1):27-35.

Borgens et al., "An Imposed Oscillating Electrical Field Improves the Recovery of Function in Neurologically Complete Paraplegic Dogs," *J. Neurotrauma*, Nov. 7, 1999; 16:639-657.

Borgens et al., "Large and persistent electrical currents enter the transected lamprey spinal cord," *Proc. Natl. Acad. Sci. U.S.A.*, Feb. 1980; 77(2):1209-1231.

Borgens et al., "Rapid Recovery from Spinal Cord Injury After Subcutaneously Administered Polyethylene Glycol," *J. Neurosci. Res.*, 2001; 66:1179-1186.

Borgens et al., "The Responses of Mammalian Spinal Axons to an Applied DC Voltage Gradient," *Exp. Neurol.*, Jun. 1997; 145(2):376-389.

Borgens, "Restoring Function to the Injured Human Spinal Cord" in *Advances in Anatomy, Embryology and Cell Biology*, vol. 171. 1997. Title Page and Table of Contents Only.

Borgens et al. "A subcutaneous tri-block copolymer produces recovery from spinal cord injury" *J. Neurosci. Res.* 2004;76:141-154.

Borgens et al., "Transected dorsal column axons within the guinea pig spinal cord regenerate in the presence of an applied electric field," *J. Comp. Neurol.*, 1986; 250:168-180.

Borgens, "Voltage Gradients and Ionic Currents in Injured and Regenerating Axons," *Advances in Neurology*, vol. 47: *Functional Recovery in Neurological Disease*, (Waxman, ed.), 1988, Raven Press: New York, NY. pp. 51-66.

Boutin, "Purdue research offers hope for canine, human spinal injuries," Dec. 3, 2004 *Purdue University News*. Available online [retrieved on Oct. 14, 2009]. Retrieved from the Internet: 2009 <http://news.uns.purdue.edu/html4ever/2004/041203.Borgens.PEG.html>; 5 pgs.

Bracken et al., "A randomized, controlled trial of methylprednisolone or naloxone in the treatment of acute spinal-cord injury: Results of the Second National Acute Spinal Cord Injury Study," *New Eng. J. Med.*, May 17, 1990; 322(20):1405-1411.

Bracken et al., "Efficacy of methylprednisolone in acute spinal cord injury," *JAMA*, Jan. 6, 1984; 251(1):45-52.

Bregman et al., "Chapter 26: Intervention strategies to enhance anatomical plasticity and recovery of function after spinal cord injury," *Advances in Neurology.*, (Seil, ed.), 1997; 72:257-275.

Bregman et al., "Recovery of function after spinal cord injury: Mechanisms underlying transplant-mediated recovery of function differ after spinal cord injury in newborn and adult rats," *Exp. Neurol.*, Sep. 1993; 123(1):3-16.

Bregman et al., "Recovery from spinal cord injury mediated by antibodies to neurite growth inhibitors," *Nature*, Nov. 30, 1995; 378:498-501.

Bregman et al., "Transplants, neruotrophic factors and myelin-associated neurite growth inhibitors: Effects on recovery of locomotor function after spinal cord injury in adult rats," *Soc. Neurosci. Abst.*, 1996; 22:764.

Brown, "Management of diskogenic pain using epidural and intrathecal steroids," *Clinical Orthopedics and Related Research*, Nov./Dec. 1977; 129:72-78.

Cajal, "Degeneration and regeneration of the nervous system," translated by R.M. May, (DeFilipe and Jones, Eds.), Oxford UP: London, England; 1928. Cover pg., publication pg., and table of contents only. (15 pgs.).

Callahan "Help for paralyzed dogs," *Star Tribune* Dec. 4, 2004, p. A5.

Carafoli et al., *Calcium ions and mitochondria, Symposium of the Society for Experimental Biology: Calcium and Biological Systems*, vol. 30, Cambridge UP, New York, 1976, 89-115.

Carafoli et al., "The Calcium Signal," *Sci. Am.*, Nov. 1985; 253:70-78.

Carpenter et al. "Response of dogs to repeated intravenous injection of polyethylene glycol 4000 with notes on excretion and sensitization," *Toxicol. Appl. Pharmacol.* 1971; 18:35-40.

Carr Jr. et al., "Effects of poloxamer 188 on the assembly, structure and dissolution of fibrin clots," *Thrombosis & Haemostasis*, 1991; 66(5):565-8.

Center for Paralysis Research, Purdue University, Institute for Applied Neurology, *Synapses*, Summer 2003. 4 pages.

Center for Paralysis Research, Purdue University, Institute for Applied Neurology, *Synapses*, Fall 2002. 5 pages.

Center for Paralysis Research, Purdue University, Institute for Applied Neurology, *Synapses*, Spring 2002. 4 pages.

Center for Paralysis Research, Purdue University, Institute for Applied Neurology, *Synapses*, Fall 2001. 4 pages.

Center for Paralysis Research, Purdue University, Institute for Applied Neurology, *Synapses*, Fall 2000. 4 pages.

Center for Paralysis Research, Purdue University, Institute for Applied Neurology, *Synapses*, Spring 2000. 4 pages.

Cheng et al., "Gait Analysis of Adult Paraplegic Rats after Spinal Cord Repair," *Exp. Neurol.*, Dec. 1997; 148(2):544-557.

Chernoff et al., "Review: Developmental aspects of spinal cord and limb regeneration," *Develop. Growth Differ.*, Apr. 1995; 37(2):133-147.

Cho et al., "Functionalized mesoporous silica nanoparticle-based drug delivery system to rescue acrolein-mediated cell death," *Nanomed.* Aug. 2008 3(4):507-519.

(56) References Cited

OTHER PUBLICATIONS

Cho et al., "Repairing the damaged spinal cord and brain with nanomedicine," *Small* Oct. 2008; 4(10):1676-1681. Available online on Sep. 16, 2008.

Choi, "Glutamate neurotoxicity and diseases of the nervous system," *Neuron*, 1988; 1:623-634.

Choi et al., "The role of glutamate neurotoxicity in hypoxic-ischemic neuronal death," *Ann. Rev. Neurosci.*, 1990; 13:171-182.

Coates et al., "Clinicopathologic Effects of a 21-Aminosteroid Compound (U74389G) and High-Dose Methylprednisolone on Spinal Cord Function After Simulated Spinal Cord Trauma," *Veterinary Surgery*, 1995; 24(2):128-139.

Coates, "Intervertebral Disk Disease," *Common Neurological Problems*, Jan. 2000; 30(1):77-110.

Davidson et al., "Improved techniques for the induction of mammalian cell hybridization by polyethylene glycol," *Somat. Cell Genet.*, 1976; 2(2):165-176.

Davidson et al., "Polyethylene Glycol-Induced Mammalian Cell Hybridization: Effect of Polyethlyene Glycol Molecular Weight and Concentration," *Somat. Cell Genet.*, 1976; 2:271-280.

Davis and Emmonds, "Benefits of epidural methylprednisolone in a unilateral lumbar disectomy: a matched controlled study," *Journal of Spinal Disorders & Techniques* Dec. 1990; 3(4): 299-307.

Depo-Medrol® Product information from the *Physician's Desk Reference* 1996; pp. 2600-2602.

Donaldson et al., "Polyethylene Glycol Rapidly Restores Physiological Functions in Damaged Sciatic Nerves of Guinea Pigs," *Neurosurgery*, Jan. 2002; 50(1):147-157.

Ducker and Hamit, "Experimental treatments of acute spinal cord injury," *J. Neurosurg.* Jun. 1969; 30(6):693-697.

Duerstock et al. "A comparative study of the quantitative accuracy of three-dimensional reconstructions of spinal cord from serial histological section," *J. of Microscopy* 2003; 210(Pt. 2):138-148.

Duerstock et al., "Advances in three-dimensional reconstruction of the experimental spinal cord injury," *Computer Medical Imaging and Graphics*, 2000; 24:389-406.

Duerstock et al., "Three-dimensional morphometry of spinal cord injury following polyethylene glycol treatment," *J. Exper. Biol.*, 2002; 205:13-24.

Duerstock, "Double labeling serial sections to enhance three-dimensional imaging of injured spinal cord," *J. Neurosci. Methods* Mar. 15, 2004; 134(1):101-107.

Eidelberg et al., "Relationship between residual hindlimb-assisted locomotion and surviving axons after incomplete spinal cord injuries," *Exp. Neurol.*, Aug. 1977:56(2):312-322.

Eidelberg et al., "Locomotor control in macaque monkeys," *Brain*, Dec. 1981; 104(IV):647-663.

Farooqui et al., "Excitatory amino acid receptors, neural membrane phospholipid metabolism and neurological disorders," *Brain Res. Rev.*, 1991; 16:171-191.

Fawcett et al., "Peripheral nerve regeneration," *Annu. Rev. Neurosci.*, 1990; 13:43-60.

Fehlings et al., "The relationships among the severity of spinal cord injury, residual neurological function, axon counts, and counts of retrogradely labeled neurons after experimental spinal cord injury," *Exp. Neurol.*, 1995; 132:220-228.

Follis et al., "Role of poloxamer 188 during recovery from ischemic spinal cord injury: a preliminary study," *Journal of Investigative Surgery*, 1996; 9:149-56.

Frim et al., "Effects of biologically delivered NGF, BDNF and bFGF on striatal excitotoxic lesions," *NeuroReport*, Apr. 1993; 4(4):367-70.

Frim et al., "Implanted NGF-producing fibroblasts induce catalase and modify ATP levels but do not affect glutamate receptor binding or NMDA receptor expression in the rat striatum," *Experimental Neurology*, Aug. 1994; 128(2):172-80.

Frim et al., "Local protective effects of nerve growth factor-secreting fibroblasts against excitotoxic lesions in the rat striatum," *Journal of Neurosurgery*, Feb. 1993; 78(2):267-73.

Frim et al., "NGF reduces striatal excitotoxic neuronal loss without affecting concurrent neuronal stress," *NeuroReport*, Jun. 1993; 4(6):655-8.

Geisler et al., "Recovery of motor function after spinal-cord injury—a randomized, placebo-controlled trial with GM-1 ganglioside," *The New England Journal of Medicine*, Jun. 27, 1991; 324(26):1829-1838.

Griffin et al., "Axonal degeneration and disorders of the axonal cytoskeleton," *The Axon*, (Waxman et al., eds.), Oxford UP: New York NY; 1995. pp. 375-390.

Hall et al., "Central nervous system trauma and stroke, II: Physiological and pharmacological evidence for involvement of oxygen radicals and lipid peroxidation," *Free Rad. Biol. Med.*, 1989; 6(3):303-313.

Hall, "Inhibition of lipid peroxidation in CNS trauma," *J. Neurotrama*, 1991; 8(Suppl. 1):S-31-S-40.

Hall, "The neuroprotective pharmacology of metholprednisolone," *J. Neurosurg*, Jan. 1992; 76(1):13-22.

Hall et al., "U-78517F: A potent inhibitor of lipid peroxidation with activity in experimental brain injury and ischemia," *J. Pharm. Exp. Therap.*, 1991; 258(2):688-694.

Hannig et al., "Poloxamine 1107 sealing of radiopermeabilized erythrocyte membranes," *Int. J. Rad. Biol.*, 1999; 75(3):379-85.

Hansebout et al., "4-Aminopyridine in chronic spinal cord injury: A controlled, double-blind, crossover study in eight patients," *J. Neurotrauma*, 1993; 10(1):1-18.

Hansen et al. "A pathological-anatomical study on disk degeneration in dog with special reference to the so-called enchondrosis intervertebralis," *Acta Orth Scand* 1952; 11:1-129.

Honmou et al., "Traumatic injury to the spinal axons," *The Axon*, (Waxman et al., eds.), Oxford UP: New York, NY; 1995. pp. 480-503.

Horelein, "Comparative disk disease: man and dog," *J. American Animal Hospital Association* 1979; 15:535-545.

Jaeger et al., "Grafting in acute spinal cord injury: Morphological and immunological aspects of transplanted adult rat enteric ganglia," *Neuroscience*, 1993; 52(2):333-346.

Jewell et al., "Pharmacokinetics of RheothRx injection in healthy male volunteers," *Journal of Pharmaceutical Sciences*, Jul. 1997; 86(7):808-12.

Katayama et al., "Massive increases in extracellular potassium and the indiscriminate release of glutamate following concussive injury," *J. Neurosurg.*, Dec. 1990; 73(6):889-900.

Ketchum, "Peripheral Nerve Repair," *Fundamentals of Wound Management*, (Hunt et al., eds.), Appleton-Century-Crofts: New York, NY; 1979. pp. 459-475.

Kiernan, "Hypotheses concerned with axonal regeneration in the mammalian nervous system," *Biol. Rev.*, 1979; 54:155-197.

Kohmura et al., "Hippocampal neurons become more vulnerable to glutamate after subcritical hypoxia: an in vitro study," *J. Cereb. Blood Flow Metab.*, Nov. 1990; 10(6):877-884.

Koob et al. "Intravenous Peg Inhibits Degeneration of Cerebral Cells after Brain Injury," *J Neurotrauma*, Oct. 2005; 22(10):1092-111.

Koob and Borgens, "Polyethylene glycol treatment after traumatic brain injury reduces β-amyloid precursor protein accumulation in degenerating axons," *J. Neurosci. Res.* Jun. 2006; 83(8):1558-1563. Available online on Mar. 22, 2006.

Koob et al., "Behavioral recovery from traumatic brain injury after membrane reconstruction using polyethylene glycol," *J. Biol. Eng.* Jun. 27, 2008; 2:9.

Krause et al. "Rapid Morphological Fusion of Severed Myelinated Axons by Polyethylene Glycol," *Proc Natl. Acad. Sci USA* 1990; 87:1471-1475.

Krause et al., "Rapid Artificial Restoration of Electrical Continuity Across a Crush Lesion of a Giant Axon," *Brain Research* 1991; 561:350-353.

Laverty et al. "A Preliminary Study of Intravenous Surfactants in Paraplegic Dogs: Polymer Therapy in Canine Clinical SCI," *J. of Neurotrauma* 2004; 21:1767-1777.

Lee et al., "The changing landscape of ischaemic brain injury mechanisms," *Nature*, Jun. 24, 1999; 399(6738 Suppl.):A7-A14.

Lee et al., "Evolution of lipid structures during model membrane fusion and the relation of this process to cell membrane fusion," *Biochemistry*, May 27, 1997; 36(21):6251-6259.

(56) References Cited

OTHER PUBLICATIONS

Lee et al. "Surfactant-Induced Sealing of Electropermeabilized Skeletal Muscle Membranes in Vivo," *Proc. Natl. Acad. Sci. USA* 1992; 89:4524-4528.
Lee et al., "Transient and stable ionic permeabilization of isolated skeletal muscle cells after electrical shock," *J. Burn Care & Rehab.*, 1993; 14(5):528-540.
Lentz, "Polymer-Induced membrane fusion: Potential mechanism and relation to cell fusion events," *Chem. Phys. Lipids*, 1994; 73:91-106.
Leskovar et al., "Giant Multinucleated Macrophages Occur within the Acute Spinal Cord Injury," *Cell & Tissue Research*, May 2001; 304(2):311-315.
Leskovar et al., "The Macrophage in Neural Injury: Changes in Cell Numbers Over Time and Levels of Cytokine Production in Mammalian Central and Peripheral Nervous Systems," *J. Exp. Biol.*, Jun. 2000; 203(12):1783-1795.
Liu-Snyder et al., "Neuroprotection from secondary injury by polyethylene glycol requires its internalization," *J. Exp. Biol.* Apr. 2007; 210(Pt 8):1455-1462.
Lucas et al., "Neuronal survival or death after dendrite transection close to the perikaryon: correlation with electrophysiologic, morphologic, and ultrastructural changes," *CNS Trauma*, 1985; 2(4):231-255.
Lucas et al., "Physical injury of neurons: Important roles for sodium and Chloride ions," *The Neuroscientist*, 1997; 3(2):89-111.
Luo et al. "Polyethylene glycol immediately repairs neuronal membranes and inhibits free radical production after acute spinal cord injury" *J. Neurochemistry* 2002;83:471-480.
Luo et al., "Polyethylene glycol improves function and reduces oxidative stress in synaptosomal preparations following spinal cord injury," *J. Neurotrauma* Aug. 2004; 21(8):994-1007.
Malmgren et al., "A sensitive histochemical method for light- and electron-microscopic demonstration of horseradish peroxidase," *J. Histochem. Cytochem.*, Nov. 1997; 25(11):1280-1283.
Marks et al., "Amphiphilic, tri-block copolymers provide potent membrane-targeted neuroprotection," *FASEB J*, Apr. 2001; 15:1107-1109.
Maskarinec et al. "Direct observation of poloxamer 188 insertion into lipid monolayers," *Biophys. J.* 2002; 82:1453-1459.
Massenburg et al., "Poly(ethylene glycol)-induced and rupture of diapalmitoylphosphatidylcholine large, unilamellar extruded vesicles," *Biochem.*, Apr. 1993; 32(6):9172-9180.
Maxwell et al., "Cytochemical evidence for redistribution of membrane pump calcium-ATPase and ecto-Ca-ATPase activity, and calcium influx in myelinated nerve fibers of the optic nerve after stretch injury," *J. Neurocytology*, Dec. 1995; 24(12):925-942.
Maxwell et al., "Freeze-fracture and cytochemical evidence for structural and functional alteration in the axolemma and myelin sheath of adult guinea pig optic nerve fibers after stretch injury," *J. Neurotrauma*, 1999; 16(4):273-284.
Maxwell, "Histopathological changes at central nodes of ranvier after stretch-injury," *Microscopy Research and Technique*, May 1, 1996; 34(1):522-535.
Maxwell et al., "Loss of axonal microtubules and neurofilaments after stretch-injury to guinea pig optic nerve fibers," *J. Neurotrauma*, 1997; 14(9):603-614.
Maxwell et al., "Ultrastructural evidence of axonal shearing as a result of lateral acceleration of the head in non-human primates," *Acta Neuropathol.*, 1993; 86(1):136-144.
Mayer et al., "Effects of poloxamer 188 in a rabbit model of hemorrhagic shock," *Annals of Clinical & Laboratory Science*, 1994; 24(4):302-11.
McNally et al. "Three-Dimensional Imaging of Living and Dying Neurons with Atomic Force Microscopy," *J. Neurocytology* 2004;33:251-258.
Merchant et al., "Poloxamer 188 enhances functional recovery of lethally heat-shocked fibroblasts," *J. Surg. Res.*, Feb. 1, 1998; 74(2):131-140.

Merck Manual of Medical Information—Home Edition, 1997, p. 352-353.
Mezrow et al., "Poloxamer 188 improves neurologic outcome after hypothermic circulatory arrest," *Journal of Thoracic & Cardiovascular Surgery*, Jun. 1992; 103(6):1143-6.
Monyer et al., "21-Aminosteroids attenuate excitotoxic neuronal injury in cortical cell cultures," *Neuron*, Aug. 1990; 5:121-126.
Mori et al., "Basic Neurophysiology of Primate Locomotion," *Folia Primatologica*, 1996; 66:192-203.
Moriarty et al. "An oscillating extracellular voltage gradient reduces the density and influences the orientation of astrocytes in injured mammalian spinal cord," *J. Neurocytol* 2001;30(1):45-57.
Moriarty et al., "The Effect of an Applied Electric Field on Macrophage Accumulation within the subacute spinal injury," *J. Rest. Neurolog. Neurosci.*, 1999; 14(1):53-64.
Moriarty et al., "Two and Three Dimensional Computer Graphic Evaluation of the Subacute Spinal Cord Injury," *J. of Neurological Sciences*, 1998; 155:121-137.
Naito et al., "Analyses of treadmill locomotion in adult spinal dogs," *Neurosci. Res.*, Aug. 1990; 8(4):281-290.
Nakajima et al., "Fusogenic activity of various water-soluble polymers," *J. Biomaterials Sci., Polymer Ed.*, 1994; 6(8):751-9.
Novelli et al., "Glutamate becomes neurotoxic via the N-methyl-D-aspartate receptor when intracellular energy levels are reduced," *Brain Res.*, Jun. 7, 1998; 451(1/2):205-212.
Ochs, "Chapter 1: A brief history of nerve repair and regeneration," *Nerve Repair and Regeneration: Its Clinical and Experimental Basis*, (Jewett et al., eds.), The C.V. Mosby Co.: St. Louis, MO; 1980. pp. 1-8.
O'Lague et al., "Physiological and morphological studies of rat pheochromocytoma cells (PC12) chemically fused and grown in culture," *Proc. Nat. Acad. Sci. USA*, Mar. 1980; 77(3):1701-1705.
O'Keefe et al., "Poloxamer-188 as an adjunct to primary percutaneous transluminal coronary angioplasty for acute myocardinal infarction," *American Journal of Cardiology*, Oct. 1, 1996; 78:747-50.
Padanlam et al., "Effectiveness of Poloxamer 188 in arresting calcein leakage from thermally damaged isolated skeletal muscle cells," *Ann. N.Y. Acad. Sci.*, May 31, 1994; 720:111-123.
Palmer et al., "Surfactant administration reduces testicular ischemia-reperfusion injury," *J. Urol.*, Jun. 1998; 159:2136-2139.
Pointillart et al. "Pharmacological therapy of spinal cord injury during the acute phase," *Spinal Cord* 2000; 38:71-76.
Pontecorvo, "Production of mammalian somatic cell hybrids by means of polyethylene glycol treatment," *Somatic Cell Genetics*, 1975; 1(4):397-400.
Potter PJ, "4-aminopyridine: Six years experience and progress in spinal cord injury," *Clin. Invest. Med.* 1996; 19(4) Suppl. S80 #533.
Potter PJ, "Sustained improvements in neurological function in spinal cord injured patients treated with oral 4-aminopyridine: three cases," *Spinal Cord* 1998; 36:147-155.
Pratt, Kimball et al. "Plasma and Cerebrospinal Fluid Concentration of 4-Aminopyridine Following Intravenous Injetion and Metered Intrthecal Delivery in Canines," *J. Neurotrauma* 1995; 12:23-39.
Principe, "Polyethylene glycols. Studies of absorption, excretion, retention, and identification," *J. Forensic Sci.* 1968; 13:90-113.
Qiao et al. "Effects of 4-aminopyridine on motor evoked potentials in patients with spinal cord injury," *J Neurotrauma* 1997; 14(3):135-49.
"Radiculopathies," [online]. Global Anatomy: Department of Anatomy, University of Wisconsin Medical School, 2002 [retrieved on May 16, 2002]. Retrieved from the Internet: <URL:http://www.anatomy.wisc.edu/SClinic/Radiculo/Radiculopathy.htm>. (8 pgs.).
Rivlin et al., "Effect of Duration of Acute Spinal Cord Compression in a New Acute Cord Injury Model in the Rat," *Surg. Neurol.*, Jul. 1978; 10(1):39-43.
Rivlin et al., "Objective clinical assessment of motor function after experimental spinal cord injury in the rat," *J. Neurosurg.*, Oct. 1977; 47(4):577-581.
Rosenberg et al., "Reduction of NaCl increases survival of mammalian spinal neurons subjected to dendrite transaction injury," *Brain Res.*, 1996; 734:349-353.
Rossignol et al., "Spinal pattern generation," *Curr. Opin. Neurobiol.*, Dec. 1994; 4(6):894-902.

(56) References Cited

OTHER PUBLICATIONS

Salzman et al., "Anesthesia influences the outcome from experimental spinal cord injury," *Brain Res.*, 1990; 521:33-39.

Schoch, "Researcher fuses spinal cords," *The Indianapolis Star*, Nov. 11, 1998; pp. 1 and 6.

Selby,"Correspondence," *Neurosurgery* 1983; 12:5:591.

Selzer, "Mechanisms of functional recovery and regeneration after spinal cord transection in larval sea lamprey," *J. Physiol.*, 1978; 277:395-408.

Shaffer et al. "The absorption and excretion of the solid polyethylene glycols ('Carbowax' Compounds)," *J. Amer. Pharm. Assoc.* 1947; 36:152-157.

Shaffer et al. "Renal excretion and volume distribution of some polyethylene glycols in the dog," *Amer. J. of Phys.* 1948; 152:93-99.

Sharma et al., "Poloxamer 188 decreases susceptibility of artificial lipid membranes to electroporation," *Biophys. J.*, Dec. 1996; 71:3229-3241.

Shi et al. "Acute Repair of Crushed Guinea Pig Spinal Cord by Polyethylene Glycol", *J. Neurphysiol* 1999; 81: 2406-2414.

Shi et al., "Anatomical repair of nerve membranes in crushed mammalian spinal cord with polyethylene glycol," *J. Neurocytol.*, 2000; 29:633-643.

Shi et al. Calcium Antagonists Fail to Protect Mammalian Spinal Neurons After Physical Injury, *Journal of Neurotrauma* 1989; 6:261-275.

Shi et al., "Compression injury of mammalian spinal cord in vitro and the dynamics of action potential conduction failure," *J. Neurophysiol.*, Sep. 1996; 76(3):1572-9.

Shi et al. "Conduction Block in Acute and Chronic Spinal Cord Injury: Different Dose-Response Characteristics for Reversal by 4-Aminopyridine," *Experimental Neurology* 1997; 148:495-501.

Shi et al., "Control of membrane sealing in injured mammalian spinal cords axons," *J. Neurophysiol.*, Oct. 8, 2000; 84(4):1763-9.

Shi et al. "Differential Effects of Low and High Concentrations of 4-Aminopyridine on Axonal Conduction in Normal and Injured Spinal Cord," *Neuroscience* 1997; 77:553-562.

Shi et al. "Functional Reconnection of Severed Mammalian Spinal Cord Axons with Polyethylene Glycol," *Journal of Neurotrauma* 1999; 16:727-738.

Shi et al., "Sucrose-gap recording from isolated spinal cord to examine axonal pathophysiology in response to compression injury," *J. Neurotrauma*, 1995; 12:996.

Shi et al., "m-Calpain dependence of membrane sealing in mammalian spinal cord axons," *Society for Neuroscience Abstracts*, 1997; 23(1):270.

Short et al. "High dose methylprednisolone is the management of acute spinal cord injury—a systematic review from a clinical perspective," *Spinal Cord* 2000; 38:273-286.

Siesjö et al., "Neurocytotoxicity: pharmacological implications," *Fundam. Clin. Pharmacol.*, 1991; 5(9):755-767.

Smucker et al., "Intravenous polyethylene glycol successfully treats severe acceleration-induced brain injury in rats as assessed by magnetic resonance imaging," *Neurosurgery* May 2009; 64(5):984-990.

Smyth et al. "The toxicity of high molecular weight polyethylene glycols; chronic oral and parenteral administration," *J. Amer. Pharm. Assoc.* 1947; 36:157-160.

Somerson et al., "Functional Analysis of an Electromechanical Spinal Cord Injury Device," *Exp. Neurol.*, 1987; 96:82-96.

"Spinal cord and meninges," [online]. Wheeless' Textbook of Orthopaedics. [retrieved on Feb. 20, 2002]. Retrieved from the Internet: <URL:http://www.medmedia.com/011/44.htm>. (2 pgs.). 2002.

"Spinal cord and nerve roots," [online]. Spine-health.com, 2002. [retrieved on Feb. 20, 2002]. Retrieved from the Internet: <URL:http://www.spine-health.com/topics/anat/a04.html>. (2 pgs.). 2002.

Strautman et al., "Intracellular Free calcium concentrations and gradients in severed and intact spinal axons," *J. Gen. Physiol.*, Dec. 1986; 88(6):57a-58a.

Stys et al., "Role of extracellular calcium in anoxic injury of mammalian central white matter," *Proc. Natl. Acad. Sci. USA*, Jun. 1990; 87:4212-4216.

Tator et al., "Review of the secondary injury theory of acute spinal cord trauma with emphasis on vascular mechanims," *J. Neurosurgery*, Jul. 1991; 75(1):15-26.

"Tetronic® 1107 Block Copolymer Surfactant," Technical Bulletin. Copyright 2002. BASF: Mount Olive, New Jersey. Available online [retrieved on Aug. 9, 2009]. Retrieved from the Internet: 2009. <http://www2.basf.us/performancechemical/pdfs/Tetronic_1107.pdf>; 1 pg.

Theriault et al., "Intrinsic organization of the rat cutaneus trunci motor nucleus," *J. Neurophysiol.*, Aug. 1998; 60(2):463-77.

Theriault et al., "Nociceptive cutaneous stimuli evoke localized contractions in a skeletal muscle," *J. Neurophys.*, Aug. 1998; 60(2):446-462.

Thomas et al., "Clinical aspects of PNS regeneration," *Advances in Neurology*, vol. 47: *Functional Recovery in Neurological Disease*, (Waxman, ed.), Raven Press: New York, NY; 1988. pp. 9-29.

Tilcock et al., "The Interaction of Phospholipid Membranes with Poly(Ethylene Glycol) Vesicle Aggregation and Lipid Exchange," *Biochem.*, 1982; 688:645-652.

Uhler et al., "The effects of megadose methylprednisolone and U-78517F on toxicity mediated by glutamate receptors in the rat neostriatum," *Neurosurgery*, Jan. 1994; 34(1):122-7; discussion 127-8.

Valentini et al., "Chapter 42: Strategies for the engineering of peripheral nervous tissue regeneration," *Principles of Tissue Engineering*, (Lanza et al., eds.), R.G. Landes Co., 671-684. 1997.

Wagih et al., "Validation of the American Spinal Injury Association (ASIA) Motor Score and the National Acute Spinal Cord Injury Study (NASCIS) Motor Score," *Spine*, 1996; 21(5):614-619.

Wiswedel et al., "Injury of mitochondrial respiration and membrane potential during iron/ascorbate-induced peroxidation," *Biochim. Biophys. Acta.*, Jun. 15, 1998; 934(1):80-86.

Working et al. "Safety of poly (ethylene glycol) and poly (ethylene glycol) derivatives in Poly (ethylene glycol) chemistry and biological applications," in *Polyethylene glycol): Chemistry and Biological Applications* Harris and Zalipsky (eds.), 1997; Title page, Table of Contents, and pp. 45-57.

Xie et al., "Membrane resealing in cultured rat septal neurons after neurite transection: evidence for enhancement by $Ca^{2+}$-triggered protease activity and cytoskeletal disassembly," *J. Neurosci.*, 1991; 11(10):3257-3267.

Xue et al., "Intracerebral injection of autologous whole blood in rats: time course of inflammation and cell death," *Neuroscience Letters*, Oct. 2000; 283:230-232.

Yawo et al., "Calcium dependence of membrane sealing at the cut end of the cockroach giant axon," *J. Neurosci.*, Jun. 1985; 5(6):1626-1632.

Young, "Secondary injury mechanisms in acute spinal cord injury," *J. Emerg. Med.*, 1993; 11:13-22.

\* cited by examiner

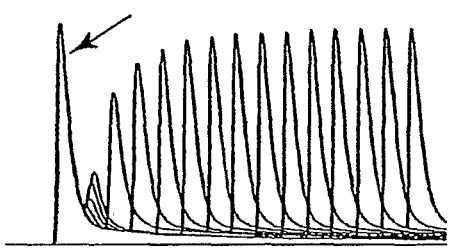
Fig. 5A
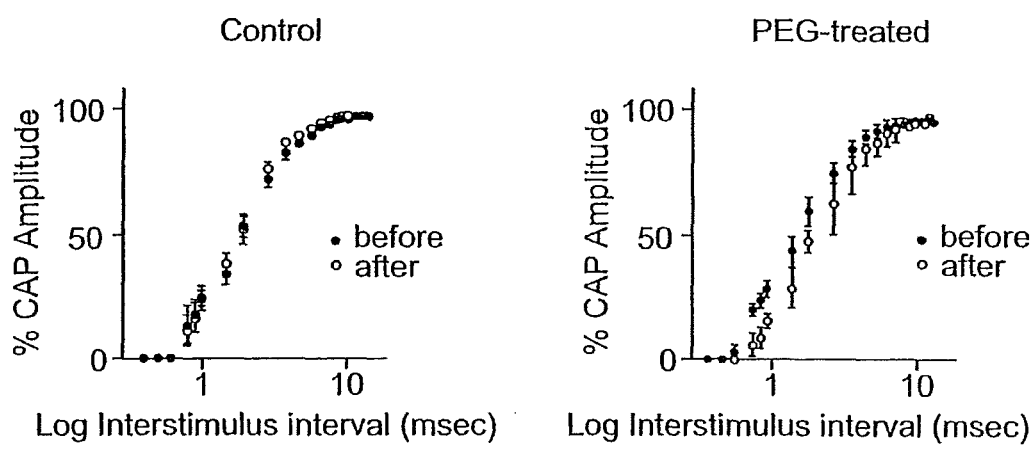
Fig. 5B  Fig. 5C

EXPERIMENTAL                          Control
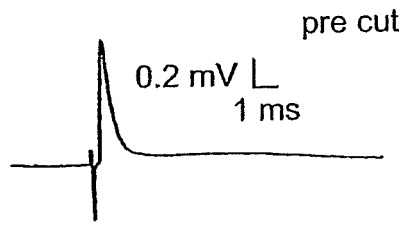
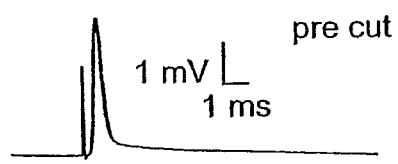
Fig. 9A                          Fig. 9E
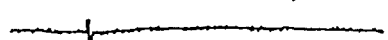
Fig. 9B                          Fig. 9F
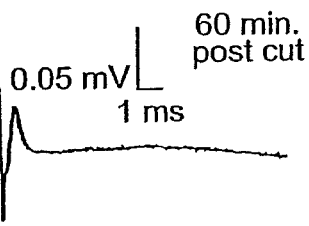
Fig. 9C                          Fig. 9G
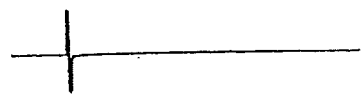
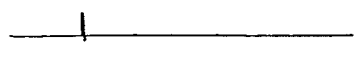
Fig. 9D                          Fig. 9H
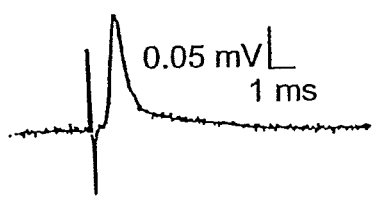
Fig. 9I

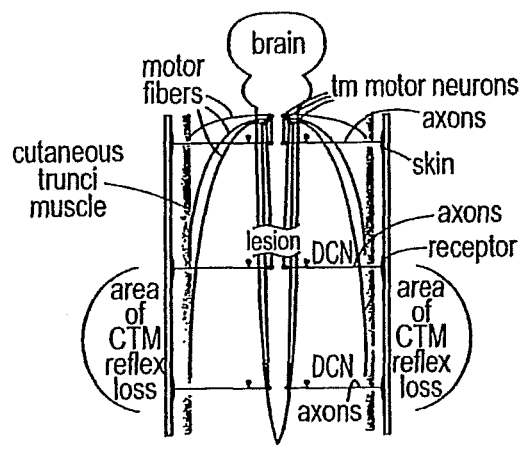
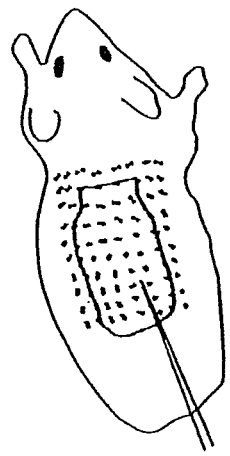
Fig. 12A          Fig. 12B
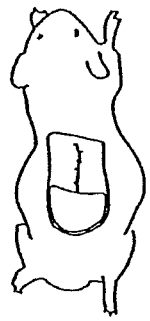
Fig. 12C
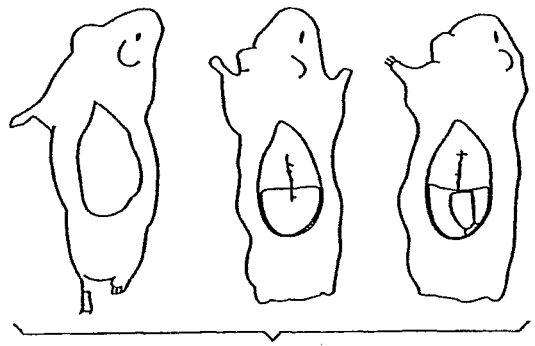
Fig. 12D

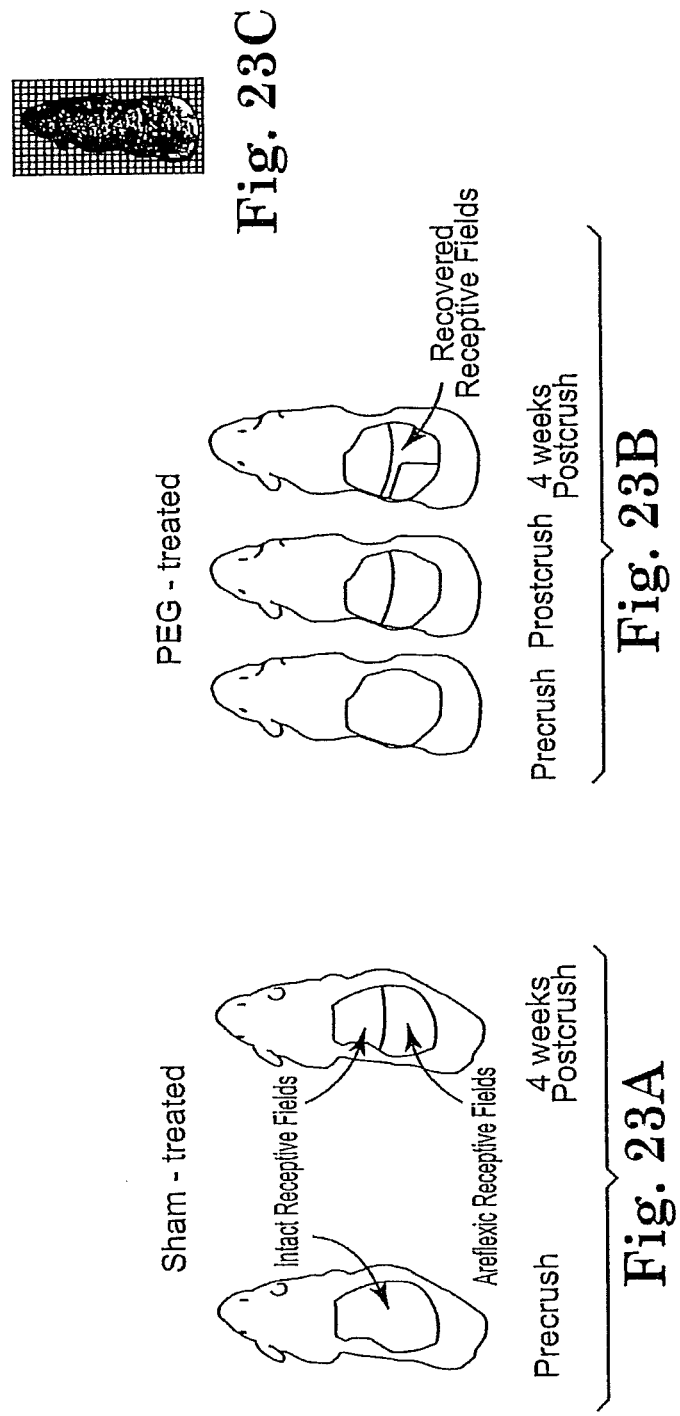

METHODS AND COMPOSITIONS FOR TREATING MAMMALIAN NERVE TISSUE INJURIES

CROSS-REFERENCE TO RELATED APPLICATIONS

This application is a continuation patent application of U.S. Ser. No. 12/508,184, filed Jul. 23, 2009, which is a continuation-in-part application of U.S. Ser. No. 09/438,206, filed Nov. 12, 1999, now U.S. Pat. No. 7,582,680, claiming priority to U.S. Ser. No. 60/108,145, filed Nov. 12, 1998, and a continuation patent application of U.S. Ser. No. 10/132,542, filed on 24 Apr. 2002, now U.S. Pat. No. 7,837,987, which claims the benefit of U.S. Provisional Patent Application No. 60/286,200 filed Apr. 24, 2001, all of which are incorporated by reference in their entirety.

This invention was made with government support under DAMD17-94-J-4242 awarded by the Department of the Army, BES9631560 awarded by the National Science Foundation, CCR9222467 awarded by the National Science Foundation, and NS039288 awarded by the National Institutes of Health. The government has certain rights in the invention.

FIELD OF THE INVENTION

The present invention relates generally to methods for treating injured mammalian nerve tissue including but not limited to a spinal cord. Specifically, the invention relates to methods for treating injured nerve tissue through an in vivo application of a biomembrane fusion agent. Pharmaceutical compositions for treating an injured spinal cord are also described.

BACKGROUND OF THE INVENTION

Mechanical damage to the nervous system of mammals results in sometimes irreversible functional deficits. Most functional deficits associated with trauma to both the Peripheral Nervous System (PNS) or Central Nervous System (CNS) result from damage to the nerve fiber or axon, blocking the flow of nerve impulse traffic along the nerve fiber. This may be due to a physical discontinuity in the cable produced by axotomy. The blockage may also occur where the membrane no longer functions as an ionic fence, and/or becomes focally demyelinated [Honmou, O. and Young, W. (1995) Traumatic injury to the spinal axons (Waxman, S. G., Kocsis, J. D., Stys, P. K., Eds.): The Axon, New York: Oxford UP, pp 480-503; Maxwell, W. L. (1996): Histopathological changes at central nodes of ravier after stretch-injury, Microscopy Research and Technique, 34:522-535; Maxwell, W. L., Watt, C., Graham, D. I., Gennarelli, T. A. (1993): Ultrastructural evidence of axonal shearing as a result of lateral acceleration of the head in non-human primates, Acta Neuropathol, 86:136-144; Maxwell, W. L., Graham, D. I. (1997): Loss of axonal microtubules and neurofilaments after stretch-injury to guinea pig optic nerve fibers, J Neurotrauma, 14:603-614; Blight, A. R. (1993): Remyelination, Revascularization, and Recovery of Function in Experimental Spinal Cord Injury (Seil, F. J., Ed.): Advances in Neurobiology: Neural Injury and Regeneration, Vol. 59, New York, Raven Press, pp. 91-103]. In either case, functional deficits occur because of the break in nerve impulse conduction. Even the severe behavioral deficits associated with spinal cord injury is now understood to be largely due to the initial mechanical damage to white matter [Blight, A. R.: Morphometric analysis of a model of spinal cord injury in guinea pigs, with behavioral evidence of delayed secondary pathology, J. Neurolog. Sci., 103:156-171, 1991]. Delayed but progressive episodes of so-called "secondary injury" [Honmou and Young, W. (1995): Traumatic injury to the spinal axons (Waxman, S. G., Kocsis, J. D., Stys, P. K., Eds.): The Axon, New York: Oxford UP pp 480-503; Young, W. (1993): Secondary injury mechanisms in acute spinal cord injury, J. Emerg. Med, 11:13-22.] subsequently enlarge the lesion leading to the typical clinical picture of a cavitated contused spinal cord, and intractable behavioral loss.

In the mammal, transection of the axon leads to the irreversible loss of the distal nerve process segment by Wallerian degeneration, while the proximal segment may survive. In the PNS, function may be restored by the endogenous regeneration of proximal segments down fasciculation pathways provided by both connective tissue and Schwann cell "tubes" which may persist for variable amounts of time post injury (Risby, M. A. (1995): Regeneration of peripheral nervous system axons (Waxman, S. G., Kocsis, J. D., Stys, P. K., Eds.): The Axon Book, New York, The Oxford University Press, pp 553-578]. The level of the injury is critical to clinical fascicular repair however, as the rate of regeneration (about 1 mm/day) may not be sufficient to avoid loss of target tissues dependent on its innervation (such as motor units in striated muscle). In the CNS, distal segments of nerve fibers do not regenerate, and their loss produces nonfunctional "target" cells, which often require innervation to maintain their integrity. One ultimate strategy to enhance recovery from CNS injury is to induce or facilitate regeneration of white matter by various means.

In the clinic, acute spinal cord transection is rare while compressive/contusive mechanical damage is typical. In the PNS, transection, stretch injury as well as compression injury to nerve trunks are commonplace. However, severe, local, mechanical damage to any type of nerve fiber membrane may still initiate a process leading to axotomy and the irretrievable loss of distal segments. These events usually begin with a breakdown in the ability of the axolemma to separate and maintain critical differences in ions between the extracellular and intracellular compartments—in particular calcium.

The devastating effects of injury to the mammalian spinal cord are not immediate. Severe mechanical injury initiates a delayed destruction of spinal cord tissue producing a loss in nerve impulse conduction associated with a progressive local dissolution of nerve fibers (axons) [Honmou, O. and Young, W. (1995) The Axon (Waxman, S. G., et al., Eds.) pp. 480-529, Oxford University Press, New York; Griffin, J. W. et al. (1995) The Axon (Waxman, S. G., et al., Eds.) pp. 375-390, Oxford University Press, New York]. This loss of sensory and motor communication across the injury site can produce a permanent paralysis and loss of sensation in regions below the level of the spinal injury. Furthermore, it is clear the most damaging effects of progressive "secondary injury" [Young, W. (1993) J. Emerg. Med. 11:13-22] of spinal cord parenchyma relative to the loss of behavioral functioning is the effect it has on white matter. Localized mechanical, biochemical, and anoxic/ischemic injury to white matter may be sufficient to cause the failure of axolemmas to function as a bather or fence to the unregulated exchange of ions [Honmou, O. and Young, W. (1995) The Axon (Waxman, S. G., et al., Eds.) pp. 480-529, Oxford University Press, New York]. This in turn compromises both the structural integrity of this region of the nerve fiber and its ability to conduct impulses along the cable. For example, elevated intracellular $Ca^{2+}$ induces depolymerization of microtubules and microfilaments producing a focal destruction of the cytoskeleton [Griffin, J. W. et al. (1995) The Axon (Waxman, S. G., et al., Eds.)

pp. 375-390, Oxford University Press, New York; Maxwell, W. L., et al. (1995) J. Neurocytology 24:925-942; Maxwell, W. L., et al. J. Neurotrauma 16:273-284].

The unrestricted movement of $Ca^{++}$ down its electrochemical gradient into the cell leads to a destruction of membranes and the cytosol, and is an initial key event in all mechanical injury to nerve fibers as well as other ischemic injuries such as head injury and stroke [Borgens, R. B., Jaffe, L. F., Cohen, M. J. (1980): Large and persistent electrical currents enter the transected spinal cord of the lamprey eel, Proc. Natl. Acad. Sci. U.S.A., 77:1209-1213; Borgens, R. B. (1988): Voltage gradients and ionic currents in injured and regenerating axons, Advances in Neurology, 47: 51-66; Maxwell, W. L. (1996): Histopathological changes at central nodes of ravier after stretch-injury, Microscopy Research and Technique, 34:522-535; Maxwell, W. L., Graham, D. I. (1997): Loss of axonal microtubules and neurofilaments after stretch-injury to guinea pig optic nerve fibers, J. Neurotrauma, 14:603-614; Maxwell, W. L., Watt, C., Graham, D. I., Gennarelli, T. A. (1993): Ultrastructural evidence of axonal shearing as a result of lateral acceleration of the head in non-human primates, Acta Neuropathol, 86:136-144; Honou and Young, 1995, Lee et al., 1999; Stys et. al., 1990]. $Na^+$ enters the localized region of the membrane insult as well, depolarizing the membrane and facilitating the release of intracellular $Ca^{++}$ stores [Carafoli, E., Crompton, M. (1976): Calcium ions and mitochondria (Duncan, C. J., Ed.): Symposium of the Society for Experimental Biology: Calcium and Biological Systems, Vol. 30, New York, Cambridge University Press, pp. 89-115; Borgens, R. B., Jaffe, L. F., Cohen, M. J. (1980): Large and persistent electrical currents enter the transected spinal cord of the lamprey eel, Proc. Natl. Acad. Sci. *U.S.A.*, 77:1209-1213; 1988; Borgens, R. B. (1988): Voltage gradients and ionic currents in injured and regenerating axons, Advances in Neurology, 47: 51-66]. Potassium exodus also pushes the resting potential of the membrane towards the Nernst potential for $K^+$ contributing to the localized region of inexcitability and blockage of nerve impulse conduction down the cable in even intact membranes. Thus, when $K^+$ rushes down its electrochemical gradient out of the cell, the resultant elevated extracellular concentration contributes to localized conduction block [Honmou, O. and Young, W. (1995) The Axon (Waxman, S. G., et al., Eds.) pp. 480-529, Oxford University Press, New York; Shi, R. et al., (1997) Society for Neuroscience Abstracts, 108:16]. However it is the progressive chain reaction of events set in motion by $Ca^{++}$ entry into the cell that initially leads to progressive dissolution of the axon—aided in later stages of the acute event by additional complex molecular processes such as the initiation of lipid peroxidation pathways and formation of "free radical" oxygen metabolites.

There are several classes of molecules that have already been shown to be able to seal cell membranes or to actually fuse membranes together [Nakajima, N., Ikada, Y. (1994): Fusogenic activity of various water-soluble polymers, J. Biomaterials Sci., Polymer Ed., 6:751-9]. These biocompatible polymers can also resolve discontinuities in the plane of the membrane into an unbroken plasmalemma, and/or become inserted into the membrane defect, sealing it and reversing permeabilization.

For over thirty years polyethylene glycol (PEG) has been known to fuse many cells together to form one giant cell. Application of this hydrophilic macromolecule has been exploited to form multicellular conjugates for the purpose of exchanging genetic material, hybridoma formation, or as a model for endogenous vesicle fusion [Davidson, R. L., O'Malley, K. A., Wheeler, T. B. (1976): Induction of mammalian somatic cell hybridization by polyethylene glycol, Somat. Cell Genet., 2:271-280; Lee, J., Lentz, B. R. (1997): Evolution of lipid structures during model membrane fusion and the relation of this process to cell membrane fusion, Biochemistry, 36:6251-6259; Lentz, B. R. (1994): Induced membrane fusion; Potential mechanism and relation to cell fusion events, Chem. and Phys. of Lipids, 73: 91-106]. PEG has also been used to fuse many phaetocychroma cells (PC-12; neuron like cells) together to produce large single units facilitating neurophysiological measurements in vitro as well as fusing the severed ends of single invertebrate giant axons in vitro [O'Lague, P. H., Huttner, S. L. (1980): Physiological and morphological studies of rat phechromocytoma calls (PC12) chemically fused and grown in culture, Proc. Nat. Acad. Sci. USA, 77:1701-1705; Krause, T. L., Bittner, G. D. (1990, 1991): Rapid morphological fusion of severed myelinated axons by polyethylene glycol, PNAS, 87: 1471-1475].

Methods and compositions for treating mammalian spinal cord injuries are needed. The present invention addresses these needs.

SUMMARY OF THE INVENTION

The present invention is directed to methods and compositions for the in vivo repair of injured mammalian nerve tissue. The invention is more particularly directed to the application or administration of an effective amount of a biomembrane fusion agent (see Definitions section below) to the site of an injury (see Definitions section below) to nerve tissue, particularly nerve tissue of the spinal cord or the peripheral nervous system. The biomembrane fusion agent may be directly contacted with the nerve tissue at the site of the injury or may be administered to the patient parenterally. Preferably, the biomembrane fusion agent is delivered to the site of the injury through the blood supply after injection of the biomembrane fusion agent into the patient. The injection may be an intravascular, intramuscular, subcutaneous, or intraperitoneal injection of an effective quantity of the biomembrane fusion agent so that an effective amount is delivered to the site of the nerve tissue injury.

Preferably, the biomembrane fusion agent takes the form of a hydrophilic polymer in the form of a polyalkylene glycol or oxide such as a polyethylene glycol, a polyethylene glycol/polypropylene glycol block copolymer such as ethylene oxide-propylene oxide-ethylene oxide (EPAN), or another hydrophilic biocompatible surfactant such as dextrans. The surfactant is preferably nonionic and may take the form of an amphipathic polymer such as a poloxamine. Most preferably, the biomembrane fusion agent is polyethylene glycol (PEG) $(H(OCH_2CH_2)_nOH)$, where n preferably ranges from 4 to about 570 or more, more preferably about 30 to about 100. PEG is used as a solvent for many compounds used in medicine. For example, PEG is used as a carrier for contrast media used in radiology, and a solvent for hemopoetic factors infused into hemophilic patients. A suitable alternative is a poloxamer (see Definitions section below). Some of these triblock polymers consist of PEG polymers with a propylene glycol core. The sizes of the individual polymeric chains are not critical to the action of the poloxamer, and the poloxamer can also be injected into the blood stream or applied topically in the same manner as PEG. (Poloxamers are also amphipathic polymers to a greater or lesser extent depending on the relative numbers of ethylene glycol and propylene glycol groups.)

In the development of the present invention, the distribution of a biomembrane fusion agent, more particularly, PEG, in animals with spinal cord injuries was traced and it was found that PEG specifically targets the hemorrhagic injury in spinal cord following any means of introducing it to the blood supply (for example, parenterally such as intravenous, subcutaneous, or intraperitoneal injection, transdermally, orally, through buccal administration or via another route of administration). Furthermore, PEG appears to more uniformly bathe the injury site when delivered by the blood supply than when it is applied to the injury directly. In testing the application or administration of PEG to spinal cord injured guinea pigs, it has been observed that the recovery of functions (both in nerve impulse conduction through the spinal cord injury and behavioral recovery) has been identical to that previously determined in response to topical (direct) application of PEG to the site of nerve tissue injury.

This is a dramatic and unexpected finding. A single dose of a biomembrane fusion agent such as PEG in aqueous solution administered beneath the back skin (subcutaneous injection) will reverse many functional deficits in severe or traumatic spinal cord injuries in guinea pigs when the dose is administered up to six (6) to eight (8) hours post injury. The PEG migrates to and selectively attaches to the site of a mammalian nerve tissue injury and functions there as a biomembrane fusion agent.

Tests show that the application or administration of a biomembrane fusion agent such as PEG to severe spinal cord crush/contusion injuries in situ produces functional recovery of an identified spinal cord mediated behavior in test mammals as well as a rapid recovery of recorded nerve impulses ascending the spinal cord through the original lesion. These physiological and behavioral recoveries following severe spinal cord injury in the test mammals are not temporary but rather stable, even improving with the passage of time. Moreover, the application of a biomembrane fusion agent such as PEG can be delayed for at least 8 hours after spinal cord injury without a loss in its effectiveness.

Accordingly, the present invention contemplates a method of treating injured mammalian, preferably human, nerve tissue that includes administering an effective amount of a biomembrane fusion agent exemplarily including a hydrophilic polymer such as a polyalkylene glycol (or oxide), or block copolymers and mixtures thereof, or a biocompatible surfactant such as a nonionic amphipathic polymer (e.g., a poloxamer or a poloxamine), or mixtures thereof. Preferably, the treatment includes an injection of the biomembrane fusion agent into a patient parenterally, including intravascularly, intramuscularly, subcutaneously, intraperitoneally, or through any other path which results in a delivery of the biomembrane fusion agent to the site of the injury via the vascular system.

The present invention also contemplates the administration of an effective amount of a biomembrane fusion agent in the form of a hydrophilic polymer such as a polyalkylene glycol or in the form of a biocompatible surfactant such as a nonionic amphipathic polymer to the site of a nerve tissue injury by contacting the nerve tissue with an effective amount of the biomembrane fusion agent directly applied in a bath to the nerve tissue. Where the biomembrane fusion agent is a polyalkylene glycol, it can preferably and particularly take the form of $C_1$ to $C_{10}$ polyalkylene glycol such as polymethylene glycol, polyethylene glycol, polypropylene glycol, polybutylene glycol, polypentylene glycol, polyhexylene glycol, polyheptylene glycol, polyoctylene glycol, polynonylene glycol, and polydecylene glycol, including branched and structural isomers thereof. The biomembrane fusion agent may more generally take the form of any mixture of acceptable individual agents, such as mixtures of two or more polyalkylene glycols, including branched and structural isomers thereof, mixtures of polyalkylene glycols with block copolymers of polyalkylene glycols, and mixtures of block copolymers of polyalkylene glycols. The use of polyethylene glycol, polypropylene glycol and polyethylene glycol polypropylene glycol block copolymers (e.g., poloxamer 188) are particularly preferred for use in the present invention, with polyethylene glycol being most preferred. In some applications, administration is facilitated by using a biomembrane fusion agent having a reduced viscosity, e.g., reduced relative to room-temperature viscosity by heating. Polyethylene glycol polypropylene glycol block copolymers (e.g., poloxamer) appear to have an acceptably low viscosity. However, it is clear that a suitably low viscosity may be attained by selecting a low-molecular-weight molecule as the biomembrane fusion agent and injecting the agent after heating the agent to a permissibly elevated temperature.

In one form of the invention, a method of treating an injured mammalian spinal cord also includes directly or indirectly (by any route of administration including through the vascular system) administering an effective amount of a potassium channel blocker to the site of nerve tissue damage, together with an effective amount of a selected biomembrane fusion agent. The potassium channel blocker can be, for example, an amino-substituted pyridine, such as 4-aminopyridine.

Yet other aspects of the invention provide compositions for treating an injured mammalian nervous system, such as an injured mammalian spinal cord, that include effective amounts of a biomembrane fusion agent and optionally a potassium channel blocker as described above. It has been unexpectedly found that such compositions synergistically treat a damaged spinal cord.

Where the biomembrane fusion agent takes the form of polyethylene glycol, it is administered in an effective amount and preferably within the dosage range of about 15 to 50 mg of PEG per body weight of the patient in kilograms where the PEG has a weight of about 1500 to 4000 Daltons. The fusion agent is preferably administered in combination with a pharmaceutically acceptable carrier, additive or excipient, more preferably in a sterile injectable saline such as lactated Ringer's solution or any other IV "fluids" commonly administered after trauma as a treatment for shock and/or blood loss. Any polyalkylene copolymer having a safe clinical use as an injectable treatment in other contexts is suitable for use in a method for treating injured nerve tissue in accordance with the present invention.

Where the fusion agent is poloxamer, a polyethylene-polypropylene-polyethylene block copolymer, or a poloxamine, it is administered preferably in an isotonic sterile saline such as a lactated Ringer's solution, USP sterile isotonic saline solution, Kreb's solutions, or other IV "fluids" solution at fusion agent dosages of 50-150 mg/kg of the patient's body weight, for instance, about 100 mg/kg of body weight. The aqueous solution is prepared in such a way as the injection is approximately 1 cc. Poloxamers are preferably accompanied by a potent antioxidant. For instance, 0.4 g of a natural antioxidant, Vitamin C, may be added to the stock solution of 350 mg/Kg P188. Any nonionic surfactant or amphipathic polymer having a safe clinical use as an injectable treatment in other contexts is suitable for use in a method for treating injured nerve tissue in accordance with the present invention.

The methodology of the present invention will permit a physician or medical practitioner (e.g., neurosurgeon) to physically and functionally reconnect transected nerve cell processes (axons), as well as immediately rescue crushed nerve processes that would otherwise progress on to axotomy and the irreversible loss of the distal axonal segment. This result is surprising. The methodology of the present invention is unexpected and dramatic for at least four more significant reasons:

1) A biomembrane fusion agent as disclosed herein can be delivered by tuberculin syringe and a fine (26 gauge) needle inserted just under the sheath of peripheral nerves near the site of crush or stretch and/or by IV injection. This operation has been performed with PEG and poloxamer in adult guinea pigs with focal crush injuries to the sciatic nerve of the leg. Observations revealed very rapid recoveries (minutes to 1 hour) of nerve impulse conduction through the injury and recoveries of muscle function in the lower leg (originally extinguished by the crush of the relevant nerve).

2) Administration of a biomembrane fusion agent through the blood supply of a patient with injured nerve tissue relieves the attending neurosurgeon of the absolute requirement to surgically expose the site of the nerve tissue injury, for instance, to remove the tough covering of the spinal cord (the dura), before a topical application of the fusion agent is made.

3) Introduction of biomembrane fusion agents through the blood supply enormously facilitates the time in which these agents could be delivered clinically. The fusion agents can be delivered as a component of IV fluids that are standardly begun even at the accident site minutes to hours after injury.

4) Introduction of a biomembrane fusion agent such as PEG and/or poloxamer through the vasculature (blood supply) also enables the use of this therapy in cases of severe head injury, as well as cerebral hemorrhage (stroke). These traumas would not have been accessible to the topical application and removal of fusion agent solutions, but are perfectly accessible to the treatment by IV injection through the normal IV fluids continuously delivered to trauma patients. Head injury and stroke are hemorrhagic events identical to spinal cord injury in that cells in these regions of the brain begin to undergo dissolution and death after they become permeabalized by even a temporary restriction of blood supply. The breaches in the membranes of the nerve cells can be molecularly sealed and the cells rescued by fusion agent application just as in spinal cord trauma.

An injection of a biomembrane fusion agent pursuant to the present invention should be made as soon as possible after a severe injury to the central nervous system. Since the biomembrane fusion agent is delivered via the blood stream, this methodology can be used to treat any form of traumatic damage to the peripheral nervous system (crush or injury where nerve fibers are not completely severed), any form of damage to the spinal cord where the cord itself is not severed into two pieces, any type of traumatic damage to the brain such as blunt force trauma or concussion, and stroke or cerebral aneurysms.

It is therefore an object of the invention to provide methods and compositions for treating a mammalian nerve tissue damage to at least partially restore nerve function.

These and other objects and advantages of the present invention will be apparent from the descriptions herein.

BRIEF DESCRIPTION OF THE DRAWINGS

FIGS. 1A through 14C are directed to experimental procedures demonstrating the effect of a direct application of a biomembrane fusion agent such as polyethylene glycol to exposed damaged nerve tissue. FIGS. 15 through 23C are directed to experimental procedures demonstrating the effect of an intravascularly delivered biomembrane fusion agent, such as polyethylene glycol, on damaged nerve tissue.

FIGS. 1A through 14C are more specifically directed to experimental procedures performed to study and determine the effects of topically applied PEG to in vitro and in vivo spinal cord injury in guinea pigs.

FIGS. 1A-1B depict experimental apparatuses used in the study. FIG. 1A depicts a top view of the double sucrose recording chamber. In FIG. 1A, from left to right, the first large compartment contains 120 mM KCl, the central large compartment contains the physiological test solutions, such as oxygenated Krebs' solution, and the third compartment also contains 120 mM KCl. The small chambers on either side of the central compartment contain 230, mM sucrose. Seals fashioned from coverslips are secured in place with high vacuum silicone grease at the locations shown to inhibit the exchange of the various media from one compartment to the next. AgAgCl electrodes for recording and stimulation are in series with socket connectors at the locations shown. In the top portion of FIG. 1B, a side view of the apparatus used to produce a standardized crush to the isolated spinal cord at its midpoint within the central compartment is shown. The position of the spinal cord injury within the central chamber is shown in the lower portion of FIG. 1B. The apparatuses are further described below with reference to Example 1.

FIG. 2 depicts electrophysiological recordings of control and PEG-treated guinea pig spinal cords at 10 seconds and 5 minutes after crushing as more fully described in Example 1. Top panel: electrophysiological recordings show the compound action potentials (CAPs) before the standardized experimental crush and the immediate loss of conduction after experimental injury. Bottom panel: electrophysiological recordings show a typical response to acute standardized injury of the isolated spinal cord strip after PEG treatment. SA, stimulus artifact.

FIG. 3 depicts a graph showing the recovery of the CAP as a percentage of the precut amplitude as a function of time post-crush. Average CAPs and their standard error (SE) are displayed for 10 spinal cord strip for each group.

FIG. 4A depicts a series of 10 superimposed electrophysiological recordings showing CAPs in response to 10 separate increasing stimulus intensities (0.015-2.0 mA, 100 µs duration squarewave stimuli) prior to the experimental crush and 1 hour after the crush in a control preparation. FIG. 4B is graph showing the preinjury amplitude vs. post injury amplitudes for 4 spinal cord strips in a modestly injured control group. FIG. 4C shows a graph of preinjury amplitude vs. post-injury amplitudes showing the hypothetical skewing of data where (a) more large caliber— fibers (with a lower stimulus threshold) are responsible for the CAP or (c) more small caliber fibers are recruited to produce the recovered CAP following injury relative to unity (b). FIG. 4D shows the actual distribution of these data points in the PEG-treated group.

FIGS. 5A-5C depict graphical representations of refractory period changes in control and PEG-treated spinal cords after double pulse stimuli. In FIG. 5A, twenty individual records of CAP responses to twin pulse stimuli are superimposed. The first of these twenty stimuli produced the single large CAP marked with the arrow. Since this first CAP is always, produced by a stimulus of the same intensity, each of these superimposed individual electrical records was identical. From left to right, the CAP produced by the second stimulus is shown. Note the typical dampened amplitude of the second CAP when triggered during the relative refractory period followed by the typical plateau in amplitude produced when the second stimulus is applied subsequent to the relative refractory period. In FIGS. 5B and 5C, the response to the secondary stimulus (as a % of the first CAP amplitude) vs. the interstimulus interval is plotted for 4 untreated and PEG-treated spinal cord strips, respectively. Filled circles show data points prior to the standardized crush injury while open circles show data points obtained 1 hour after the injury.

In FIG. 6A, untreated spinal cord strips were treated with 100 μM 4-AP at 1 hour post-injury. In FIG. 613, 100 μM 4-AP was administered 1 hour post-PEG application.

FIG. 7 depicts a proposed mechanism of the synergistic effect of PEG and 4-AP as more fully described in Example 2. The membrane lesion obtained by mechanical compression is depicted by holes. Small arrowheads represent potassium channels.

FIG. 8 depicts the laboratory device used to stabilize and hold the two segments of the spinal cord together during fusion.

FIGS. 9A-9I depict electrophysiological recordings in adult guinea pig spinal cords at 37° C. FIG. 9A shows a normal compound action potential (CAP) recorded from a strip of ventral white matter prior to cutting the spinal cord. Two minutes after this record was taken, the strip was completely severed transversely, eliminating CAP conduction to the recording site as seen in FIG. 9B. Although the CAP began to recover within 15 minutes of PEG application, FIG. 9C shows the weak recovering compound action potential 60 minutes post transection. FIG. 9D is typical of all fused cords tested, where a second transection through the fusion plane eliminated the recovered CAP. FIGS. 9E-H show the results of control experiments. FIG. 9E shows a typical CAP. In FIG. 9F, this CAP was subsequently eliminated following transection when the two segments of white matter were tightly abutted and treated identically to the fusion procedures except that PEG was not applied. In FIG. 9G, another typical CAP is shown. After transection, the spinal cord strips used to obtain FIG. 9G data were loosely abutted following complete transection and PEG was applied. Note the lack of any recovered CAP in FIG. 9H. FIG. I shows another recovered CAP produced by PEG fusion at the same level of amplification as shown in FIG. 9C. All traces represent a computer average of 20 individual records. The scale bar in FIG. 9A is for FIGS. 9A, 913, and 9D. The scale bar in FIG. 9E is for FIGS. 9E-H.

In FIG. 11 C, the arrows point to three of many terminal clubs of unfused fibers within the FE injected segment of the cord mingling with fused fibers traced across the original plane of transection. The arrows in FIG. 11 D point to two FIR-labeled fused axons that could be traced across to the opposite cord segment. The asterisk (*) marks one nearby unfused axon ending in a terminal club near the transection plane. In FIG. 11 E, a 1 micron plastic embedded section is shown, displaying a region of axon reattachment. FIG. 11 F is a higher magnification view of a plastic section adjacent to one shown in FIG. 11 E, and shows that the site of continuity is produced by a collection of abnormal, unmyelinated axon segments which are in continuity with myelinated axons in both halves of the white matter strip. The scale bars are: FIG. 11A=50 μm, FIG. 11C=25 μm, FIG. 11D=20 μm, FIG. 11E=10 μm, and FIG. 11F=5 μm.

FIG. 12A is a diagram of the sensory and motor components of the cutaneous trunci muscle (CTM) reflex of the guinea pig as more fully discussed in Example 5. FIGS. 12B-12D depict drawings of captured and superimposed video images of a guinea pig during a period of CTM stimulation with a monofilament probe. Two video frames were superimposed to show the position of the dots prior to stimulation (black dots) and ⅕sth second after stimulation [red dots; see also Blight et al., (1990) J. Comp. Neurology 296: 614-633; and Borgens, R. B. and Shi, R. (1999) J. Faseb (in press)]. FIG. 12C shows the receptive field prior to spinal cord injury. One circumscribed region is a superimposed image 4 days post injury which shows the region of CTM loss. Within this region, tactile stimulation no longer produced contraction of the skin. In this sham-treated animal, CTM functioning remained unchanged until sacrifice 1 Month post-injury. FIG. 12D shows behavioral recovery following PEG application: From left to right, the first drawing shows the normal CTM receptive field prior to spinal cord injury. The second drawing shows the undamaged receptive field and the region of CTM loss is shown prior to the application of PEG. The third drawing shows the same guinea pig 4 days following the application of PEG. The region of CTM behavioral recovery, which was observed within the first 6 hours post PEG application and which increased in size with time to restore about 29% of the area of CTM behavioral loss by 4 days post injury, is outlined.

In FIG. 13C, SSEPs are shown before and after PEG application. From top to bottom: a typical SSEP prior to spinal cord injury; an SSEP showing immediate loss of the SSEP following injury; SSEP of a median nerve control; SSEP 1 hour post PEG; SSEP 1 day post PEG; and SSEP 4 days post-PEG. FIG. 13D depicts a graph of the mean and standard error of both amplitude and latency of the early arriving (PI) SSEPs in 10 PEG-treated animals as a function of time after crush.

FIGS. 14A-14C depict SSEP electrical recordings in control guinea pigs and guinea pigs treated with PEG at various times postcrush. FIG. 14A shows a typical SSEP prior to compression of the spinal cord and its elimination following injury as in FIGS. 1313-13D. FIG. 14B depicts SSEP electrical recordings of control, sham-treated animals, after various indicated time periods. SA=stimulus artifact; P1=first arriving SSEP (latency=about 18 ms); P 2=late arriving potentials (latency=about 34 ms). FIG. 14C depicts an electrical recording showing SSEPs after delayed treatment with PEG.

FIG. 15 depicts a surgical exposure performed on the sciatic nerve of a test mammal and shows the branches (which are cut see methods) of the sciatic nerve and the gastrocnemius muscle. Note the position of the two transducers, one measuring the force of muscle contraction, the other the displacement of the hind paw. The relative position of the hook electrodes stimulating the sciatic nerve proximal to its insertion on the gastrocnemius is shown as is the placement of bipolar disc electrodes on the muscle to record the spread of APs in response to stimulation. All records are acquired simultaneously on three channels of recording equipment, a fourth channel being used to display an event marker triggered by the stimulation pulse. For illustration purposes only, the drawing is not made to scale.

FIG. 16 is a graph depicting PEG-mediated recovery of CAPs in the isolated sciatic nerve of FIG. 15. The top electrical record shows a CAP stimulated and recorded within the double sucrose gap chamber. Note its complete elimination after transection (second trace) and its partial recovery following abutment of the proximal and distal segments and PEG application (third trace).

FIG. 19 is a series of graphs showing recovery of functions in the gastrocnemius muscle in response to PEG treatment. This set of records was obtained 5 minutes after PEG treatment to the nerve injury in the same animal whose records are shown in FIGS. 18A and 18B. Note the rapid and robust recovery of AP and muscle contractile force as emphasized by the substantial reduction in amplifier gain required to record them. Compare recording scales to pre and post injury records shown in FIGS. 18A and 18B. This recovery was stable for the next hour of monitoring.

In FIGS. 21A-21D, the distribution of FI-PEG in crushed spinal cord is shown using three types of application. The application of PEG was made within ½ hour of the constant displacement crush injury, and evaluated by fluorescent microscopy of 50 µm thick frozen cross sections about 24 hours later. In FIG. 21A, a typical control section is shown in darkfield—the image digitally enhanced to reveal the very faintly labeled spinal cord. Such uninjured control sections were obtained by harvesting a segment of the spinal cord at least 3-4 vertebral segments from the injury site. Note the characteristic labeling of PEG in uninjured spinal cord at the level of detection. The arrows point to weakly labeled regions of vasculature in the gray matter and at the pia1 surface. FIG. 21B shows strong labeling of PEG at the epicenter of the crush produced by a 2-minute topical application of PEG to the lesion as in previous reports. Arrows point to relatively unlabeled central regions of this injury. In FIGS. 21C and 21D, heavy FI-PEG labeling is shown associated with subcutaneous and intravenous injection respectively. In FIG. 21C, the arrow points to a cyst forming around the swollen central canal. Note the extensive labeling of only the injury site by all methods. The scale bar=500 µm FIGS. 22A and 22B shows a typical SSEP recording in response to tibial nerve stimulation. Note the early and late arriving evoked potentials (P1 and P2) in the intact spinal cord, and their immediate elimination by the spinal cord injury. Though not shown for every record, the median nerve control procedure was performed any time an SSEP was not recorded, demonstrating the failure to record CAPs was due to the injury. In FIG. 22A, a typical set of records is shown for one control animal to the 1 month time point when the study was concluded. Note the complete lack of SSEP conduction and the robust Median nerve induced SSEP, In FIG. 22B, a typical set of electrical records for a PEG-treated animal is shown. Note the elimination of the tibial nerve derived SSEP by the spinal cord injury, and the positive median nerve control procedure performed at the same recording time. Before the end of the first day post-injury, SSEP conduction was restored by this subcutaneous PEG injection made 6 hours after the injury. Recovered evoked potentials continued to improve in amplitude and latency during the next month of observation, and in no case were recovered SSEPs lost after their recovery. The insert displays the amplitude and time base for all records except median nerve stimulations, which were recorded at ½ this sensitivity, but using the same time base.

FIGS. 23A-23C are tracings of captured and superimposed video images of a guinea pig during a period of CTM stimulation with a monofilament probe, showing behavioral recovery following subcutaneous PEG administration. These tracings are derived from stop motion videotape analysis of cutaneous trunchi muscle (CTM) stimulation regimens in which the entire CTM receptive field is first determined in the uninjured guinea pig (circumscribed). Probing inside this region of back skin with a monofilament probe produces back skin contractions, while probing outside the region does not. This line is drawn on the shaved back of the sedate animal with a marker while the investigator probes the region. The entire procedure is videotaped from above, and the various regions of both intact receptive fields and areflexia are reconstructed from these video images. Note that in all animals, the midthoracic spinal cord injury eliminates CTM responsiveness below the level of the injury on both sides (circumscribed). In control animals (FIG. 23A), this region of areflexia remained unchanged for the duration of the experiment. In PEG-treated animals (FIG. 23B), a variable region of the lost receptive CTM fields recovered within a short time of treatment. That region shows a region of CTM recovery for this one animal comprising about 55% of the original area of CTM loss. The inset (FIG. 23C) shows the 4-week video image which was used to reconstruct the regions of intact and nonfunctional receptive fields. The dot matrix allows precise alignment and superimposing of receptive fields, as well as a deeper analysis of the vector of skin movement, the velocity of skin contraction and latency when required (data not shown).

In FIG. 24A, an overlay drawing of superimposed video images of a guinea pig is shown. The upper dot of each pair of juxtaposed dots is a permanent marker tattooed on the shaved backskin, and the lower dot of each pair reveals the position of the markers at the peak of skin contraction—captured by stop frame video analysis. The exact place of tactile stimulation producing these CTM contractions is shown by the position of the monofilament probe MP used to stimulate the skin. During the period of testing, a boundary line BL was drawn onto the back of the animal with a marker revealing the total CTM receptive field. Stimulation within the circumscribed area produced skin contractions—outside it did not. The actual video image source of the drawing is shown in FIG. 24C. The box in FIG. 24A is magnified in FIG. 24B, showing that the direction of skin contraction is generally towards the probe MP (arrow), and shows the distance of that contraction (hatched lines). That distance (2 mm) divided by the duration in time required to produce it (0.12 seconds) equals the velocity of skin contraction (16.7 ram/sec).

FIG. 26A is a drawing or tracing showing a normal and complete receptive field RF on a control guinea pig as shown in FIGS. 24A-24C and described in below with reference to Example 9. The region of areflexia RA is outlined on the next image produced in FIG. 26A, 24 hours post injury to the spinal cord. Note that about ½ of the total CTM receptive field is lost due to severe spinal cord compression. One month later, this region remains unchanged. The video image used to produce the last drawing is shown on the far right. FIG. 26B shows, from left to right a similar set of images to those of FIG. 26A. The normal receptive field RF and the region of areflexia RF post spinal cord injury are marked. The region of CTM recovery RCR in response to PEG application is shown in the last drawing—demonstrating a recovered region of CTM sensitivity comprising about 42% of the original region of areflexia.

FIG. 27A was made pursuant to the methods used in generating FIGS. 24A and 24B. Note however the modest region of CTM recovery RCR-revealed by receptive field testing as described in the methods of Example 9 and in FIGS. 24A-24C. In the magnified section shown in FIG. 24B, note that position of the probe MP within the region of recovery, and the movement of the skin marker dots MD towards the probe MP. Probing outside the region RCR did not produce CTM reflex movements, but did elicit contractions when probing in the region MG (above the level of the injury).

FIG. 28A shows, from top to bottom, averaged traces of evoked potentials obtained from the same animal—from the preinjury electrical record to records obtained 1 month post injury. Note the complete lack of SSEPs in response to spinal cord injury. This was characteristic in 100% of the control population at all time points tested. A median nerve control stimulation was also carried out at these times, however only the 1 month record is shown in the last trace, the arrow pointing to a strong early arriving evoked potential (refer to FIGS. 25A-25C. In FIG. 28B, a recovery of SSEP conduction in a PEG treated animal is shown. Note the characteristic double SSEP peaks in the uninjured animal. Note the complete loss of these peaks following injury and the positive median nerve control procedure carried out at this same time point. One day post injury to 1 month post injury records show the recovery of SSEP conduction. The dotted line marked the approximate peak magnitude of the early arriving SSEP, note the latency to peak contraction is reduced with time. Such recovering SSEPs were characteristic of 100% of the PEG treated animals contrasted to the complete lack of such conduction in all control animals.

FIG. 31A shows the sedated dog and the placement of bipolar stimulating pin electrodes, inserted subcutaneously, in the hind limb at the distal popliteal area approximately 0.5-1 cm apart. These electrodes stimulated the tibial nerve of the hind limb (red wires). A similar procedure was used to stimulate the median nerve of the forelimb (wires). Trains of square wave stimulations (0.5-3.0 mA amplitude, 200/min) were applied to evoke compound nerve impulses from these nerves. To record evoked potentials, scalp needle electrodes were inserted subcutaneously over the somatosensory cortex contralateral to the side stimulated, while reference electrodes were inserted on the opposite side between the mastoid and the pinna of the ear. The placement of recording electrodes was facilitated by stimulation of the median nerve at the outset, a neural circuit above, and unaffected by, the spinal cord injury (inset, circuit 2). This procedure also provided a positive control recording to validate the frequent inability to record evoked potentials stimulated at the hind limb—but whose ascending potentials are blocked by the spinal cord lesion (inset, circuit 1).

In FIG. 32A, a 6-week progression of recovery of conduction through the lesion is shown for a PEG-treated dog. Each trace is the averaged waveforms of 3-4 trains of 200 stimulations as described in FIGS. 30A-30E. There is complete absence of an SSEP in this paraplegic animal prior to surgery, and approximately 4 days later. The third trace is a median nerve control procedure. There is no evidence of recovered conduction at 1 week post injury. By 6 weeks post-surgery, two distinct evoked cortical potentials had returned, a typical early arriving peak of approximately 26 msec latency (P 1), and a later arriving peak (P 2), of approximately 45 msec latency.

In FIG. 32B, a low amplitude, long duration, but reproducible evoked potential recovered within 15 min of a slow injection of PEG is shown. This atypical SSEP appeared to segregate into an early arriving peak of about 15-20 msec latency, and a more condensed and later arriving peak (P 2) of about 32-35 msec latency. SA=stimulus artifact. The time base and sensitivity scale is for both FIG. 32A and FIG. 32B.

DEFINITIONS

Figure 1A:
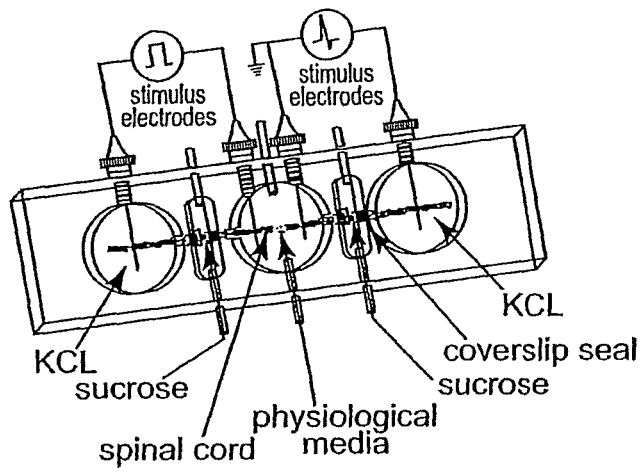

The term "nerve tissue" as used herein refers to any vertebrate nerve tissue, particularly including cells of the central nervous system (CNS) and peripheral nervous system. More particularly, nerve tissue includes spinal cord neuronal structures, peripheral nervous system nerves, and nerve cells of the brain.

The word "injury" is used herein to generally denote a breakdown of the membrane of a nerve cell, such that there is a collapse in the ability of the nerve membrane to separate the salty gel on their insides (cytoplasm) from the salty fluid bathing them (extracellular fluid). The types of salts in these two fluid compartments is very different and the exchange of ions and water caused by injury leads to the inability of the nerve to produce and propagate nerve impulses—and further to the death of the cell. The injury is generally a structural, physical or mechanical impairment and may be caused by physical impact, as in the case of a crushing, compression, or stretching of nerve fibers. Alternatively, the cell membrane may be destroyed by or degraded by a chemical imbalance or physiological malfunction such as anoxia (e.g., stroke), aneurysm or reperfusion. In any event, an "injury" as that term is used herein more specifically contemplates a nerve membrane defect, interruption, breach, or rupture (in the phospholipid bilayer) which can be treated and sealed by the administration of a biomembrane fusion agent as described herein.

The term "biomembrane fusion agent" is used herein to designate any and all molecules which are not only compatible with vertebrate, and more specifically mammalian, nerve cells but also have an affinity for nerve cell membranes so as to attach to injured nerve cells at the site of an injury. A biomembrane fusion agent thus serves in part as a kind of biological cement or filling material which bridges over ruptures in neuronal structures. This sealing is extremely rapid (minutes) and facilitates the repair of the damaged neuronal structures by natural physiological processes which are complete at much later times (1-7 hours). The sealing of neuronal membranes as described herein naturally arrests or inhibits the progressive destruction of nervous tissue after an injury to the nerve cell. Exemplary biomembrane fusion agents include hydrophilic polymers such as polyalkylene glycols (polyalkylene oxides) and polyalkylene glycol block copolymers such as polyethylene glycol/polypropylene glycol block copolymers (e.g., poloxamer 188) and ethylene oxide-propylene oxide-ethylene oxide (SPAN), and further include biocompatible surfactants, particularly nonionic surfactants and more particularly amphipathic polymers such as poloxamines. Poloxamers may also be considered to be amphipathic polymers. Poloxamers are hydrophilic to the extent that there is a greater number or greater weight percentage of ethylene glycol groups as opposed to propylene glycol groups. A biomembrane fusion agent at that term is used herein may comprise a collection, mixture, or combination of individual biomembrane fusion agents each of which is effective in its own right to seal ruptures in nerve membranes.

The term "effective amount" when used herein with reference to a biomembrane fusion agent denotes a quantity of the agent which, when administered to a patient or subject, is sufficient to result in a measurable improvement in electrical and/or behavioral function of a nerve which has been so damaged or injured that normal functioning is not possible. As discussed below, the efficacy of the treatment may be determined in a variety of ways, including methods which detect restoration of nerve function. With respect to the use of the term "effective amount" with other agents, for example, potassium channel blockers, that term is used to describe an amount of an agent effective within the context of that agent's use in the present invention.

The term "hydrophilic polymer" means any macromolecule (molecular weights of 200 daltons and greater) which exhibits an affinity for or attraction to water molecules and which comprises multiple instances of an identical subunit ("monomer") connected to each other in chained and/or branched structures.

A "surfactant" is a molecule exhibiting both an affinity for or attraction to polar molecules such as water and an affinity for or attraction to non-polar molecules such as lipids, fats, oils, and greases. A "nonionic surfactant" is electrically neutral, i.e., carries no positive or negative charge. However, a nonionic surfactant may have localized quantum variations in charge leading, for example, to a polar substructure evidencing an affinity for other polar molecular structures such as water molecules. In the context of the present disclosure, surfactants include amphipathic polymers.

An "amphipathic polymer" as that term is used herein relates to polymers which have localized quantum variations in charge giving rise to polar substructures and non-polar substructures. The polar substructures evidence an affinity for or attraction to other polar molecular structures such as water molecules (hydrophilic), while the nonpolar substructures exhibit an affinity or attraction for nonpolar molecules such as lipids, oils, greases, fats, etc. (lipophilic).

Poloxamers, also called non-ionic detergents, and/or triblock polymers, comprise a polyethylene glycol chain(s) (block 1), then a polypropylene glycol chain (block 2), followed by a polyethylene glycol chain(s) (block 3). These compounds can be synthesized in numerous conformations and molecular weights. The weights of the various "blocks" can even vary between themselves—leading to a complicated nomenclature. What all of the poloxamers have in common is a hydrophobic head group (block 2), surrounded by hydrophilic (PEG) chains. The hydrophobic "head" is believed to insert itself into the "hole" in a membrane (where the hydrophobic interior of the bilamminer membrane is exposed) while the hydrophilic PEG arms interdigitate and link with or attach to the nearby, more normal, membrane.

The term "poloxamine" denotes polyalkoxylated symmetrical block polymers of ethylene diamine conforming to the general type $[(PEG)_X-(PPG)_Y]_2-NCH_2CH_2N-[(PPG)_Y-(PEG)_X$.

The word "biocompatible" means that a substance can be placed into intimate contact with biological structures, including cells and cellular membranes, without detriment to the continued physiological functioning of the contacted cells and membranes.

The term "polyalkylene glycol" refers to a molecule having the chemical formula $H(O[CH_2]_m)_nOH$ where m and n are nonzero integers. The integer m has the following values for exemplary polyalkylene glycols: polymethylene glycol (m=1), polyethylene glycol (m=2), polypropylene glycol (m=3), polybutylene glycol (m=4), polypentylene glycol (m=5), polyhexylene glycol (m=6), polyheptylene glycol (M=7), polyoctylene glycol (m=8), polynonylene glycol (m=9), and polydecylene glycol (m=10), including branched and structural isomers thereof. Pursuant to the present disclosure, polyalkylene glycols have a molecular weight between about 200 and about 25,000 daltons, and preferably between about 400 daltons and about 3500 daltons.

The word "carrier" is used herein to denote a liquid matrix, medium or solvent in which molecules of a biomembrane fusion agent are dispersed or distributed. A pharmaceutically acceptable carrier is one which is biocompatible to vertebrate and more particularly mammalian tissues. Generally acceptable carriers include water, saline solutions, among numerous others.

By definition a "potassium channel blocker" or "$K^+$ channel blocker" is any agent that specifically and sterically inserts itself into (or otherwise deactivates) any of the several and growing classes of K+ channels. This includes both fast and slowly activating channels and both "voltage gated or non-gated" channels. Almost all channels for K+ are "gated" by the voltage across the cell membrane. When these channels are open, K+ tends to move from the cytoplasm into the extracellular fluid because it is about 100 times more concentrated inside than outside the cell. This K+ exodus (which among other things helps extinguish the nerve impulse, bringing the membrane potential back to a resting state) can thus be "blocked". In regions of demyelination or membrane potential polarization, K+ channel blockade can both increase excitability, as well a extend the distance along a nerve fiber in which a nerve impulse can travel before it is extinguished. In spinal cord injury, this may only be a few millimeters of nerve fiber damage, with absolutely normal membrane on either side. There are many known K+ channel blockers including reversible blockers (TEA) and some proteins (synthesized from snake venoms) that irreversibly block these channels. Potassium channel blockers include substituted pyridines and, more particularly, amino-substituted pyridines. The application of K+ channel blockers to spinal cord repair as described herein involves the fast potassium channel, type I, blocker 4-AP (4-aminopyridine) and its analog 3, 4 di-aminopyridine. Too high a dosage, or the use of the other blockers (more non specific and poorly reversible) may lead to convulsions and even death.

The delivery of a biomembrane fusion agent via a vascular system of a patient entails the administration of a biomembrane fusion agent via a pathway including one or more veins and/or arteries of the patient. Instead of direct application in which the agent is injected into the patient at the site of exposed nerve tissue, the vascular-system-mediated delivery of a biomembrane fusion agent contemplates an administration and subsequent conveyance of the agent to the site of an injured nerve via the vascular system of the patient. The administration of the biomembrane fusion agent is preferably by injection, for example, via a hypodermic needle or catheterization, either directly into a vein or artery or indirectly by subcutaneous injection into muscle tissue or intraperitoneally. Other methods may also be effective, for example, by ingestion, transmembrane delivery (including transdermal delivery), by suppository, through inhalants, buccally, or by implantation.

DESCRIPTION OF THE PREFERRED EMBODIMENTS

For the purposes of promoting an understanding of the principles of the invention, reference will now be made to preferred embodiments and specific language will be used to describe the same. It will nevertheless be understood that no limitation of the scope of the invention is thereby intended, such alterations and further modifications of the invention, and such further applications of the principles of the invention as illustrated herein, being contemplated as would normally occur to one skilled in the art to which the invention relates.

The present invention provides methods and compositions for treating injured nerve tissue of a vertebrate. The methods and compositions are designed to at least partially restore nerve function in the vertebrate. In one aspect of the invention, methods are provided for treating an injured or damaged vertebrate spinal cord that include contacting the spinal cord with an effective amount of a biomembrane fusion agent. The compositions include a biomembrane fusion agent, preferably a polyalkylene glycol such as polyethylene glycol (chemical formula: $H(OCH_2CH_2)_nOH$) and/or a nonionic surfactant such as an amphipathic polymer (e.g., a poloxamer or a poloxamine), and/or mixtures or copolymers thereof. In alternative embodiments, the method may include treating the nervous system with a potassium channel blocker, preferably a substituted pyridine, such as an amino-substituted pyridine, either before, during or after contacting the spinal cord with the biomembrane fusion agent. Other aspects of the invention provide compositions for treating an injured nervous system of a vertebrate. The preferred compositions include a biomembrane fusion agent and a potassium channel blocker.

As indicated above, in a first aspect of the invention, a method of treating an injured spinal cord of a vertebrate is provided. The method is preferably performed in vivo, although it may also be used in vitro, for example, in the study of spinal cord components or functionality.

The preferred biomembrane fusion agent is a polyalkylene glycol. A wide variety of polyalkylene glycols may be used, including those, for example, where the alkylene group is methylene, ethylene, propylene, butylene, pentylene, hexylene, heptylene, octylene, nonylene, and decylene, including branched and structural isomers thereof. Preferably, the polyalkylene glycol will be water-soluble and is selected from the group consisting of polyethylene glycol, polypropylene glycol and block copolymers of polyethylene glycol and polypropylene glycol. A more preferred polyalkylene glycol is polyethylene glycol. Although a wide range of molecular weight polyalkylene glycols may be used (between about 200 daltons and about 25,000 daltons) depending on the ability of the polyalkylene glycol to pass through various biological barriers such as the digestive tract, polyalkylene glycols and polyalkylene glycol block copolymers of molecular weight of about 400 to about 3500 daltons are preferred. Such biomembrane fusion agents may be synthesized by methods known to the art or may be purchased commercially.

The biomembrane fusion agent may also be a polyalkylene glycol/protein conjugate as known in the art, wherein the protein preferably aids in scavenging free radicals. For example, the biomembrane fusion agent, such as polyethylene glycol or other alkylene oxide, may be conjugated to catalase to form PEG-catalase, or to superoxide dismutase to form PEG-SOD. Such conjugates are available commercially from Sigma, St. Louis, Mo. The biomembrane fusion agent, may also be conjugated to a biodegradable surgical glue, such as a commercial fibrin glue, to facilitate and stabilize reattachment and fusion of severed nervous tissue.

Alternatively, the biomembrane fusion agent may be a biocompatible surfactant, preferably a nonionic surfactant and more preferably an amphipathic polymer such as a poloxamer or a poloxamine.

The biomembrane fusion agent may be provided in a pharmaceutically acceptable carrier. Such carriers include, for example, water, preferably sterile and including distilled water, and any other pharmaceutically acceptable carrier known to the art that will not have an adverse effect on the treatment. Sterile distilled water is a preferred carrier in work to date.

The biomembrane fusion agent is administered to the patient as soon after injury as possible and prior to irreversible dissolution of axonal membranes and the myelin sheath. Although this time period may vary depending on the nature and extent of the injury, the fusion agent is typically administered immediately after the injury occurs, and preferably not later than about 24 hours post-injury, but is typically administered between about 1 hour to about 8 hours post-injury. Though early treatment is preferred, administration of the biomembrane fusion agent may still be beneficial for up to 2 weeks after the initial nerve injury (called the "primary injury"). This is because nerve injury is a continuous, slow, progressive event, especially in spinal cord where it is called "secondary injury" (Tator and Fehlings 1991, J. Neurosurgery 75:15-26).

The biomembrane fusion agent may be delivered to the site of injury by any suitable method. Preferably, the biomembrane fusion agent is administered through the vascular system of the subject or patient. The fusion agent may be injected directly into the vascular system or indirectly by injection intramuscularly, subcutaneously or intraperitoneally. It has been discovered that an indirect administration of a biomembrane fusion agent such as polyethylene glycol via the vascular system of the patient unexpectedly results in a selective adherence of the fusion agent (e.g., PEG, poloxamer or other agent) to the injured nerve tissue. There is little or no adherence to undamaged nerve tissue. Without being limited by way of theory, it is believed that by adhering to damaged nerve tissue, the biomembrane fusion agent promotes the natural healing processes of the damaged nerve cells.

Where the biomembrane fusion agent is a polyalkylene glycol such as PEG, the fusion solution comprises fusion agent in an amount of typically about 15 to about 50% by weight and preferably is administered in doses of about 15-50 mg PEG per body weight in kilograms of the patient where the PEG has a weight of 1500-4000 Daltons. Where the biomembrane fusion agent is an amphipathic polymer such as a poloxamer or a poloxamine, the fusion solution typically contains fusion agent in an amount of about 15 to about 50% by weight and is administered in dosages of about 15-150 mg poloxamer or poloxamine per body weight in kilograms of the patient.

Where the agent is applied directly to damaged nerve tissue which has been exposed, for example, via surgical procedures, the agent may be applied with any suitable liquid dispensing device. Although the percentage by weight of the fusion agent in the direct-application composition may vary, the composition typically includes fusion agent in an amount of at least about 40% by weight, more preferably about 40% to about 50% by weight, and most preferably about 50% to about 55% by weight.

In the case of a direct-contact application, the injured site is exposed to the fusion agent for a time period effective for treating the injury. This time may vary depending on the size of the lesion, the extent and nature of the injury, the biomembrane fusion agent used, and the concentration of the biomembrane fusion agent. The lesion is typically exposed to the agent for at least about one minute and more preferably at least about 2 minutes. In preferred embodiments, the fusion agent is removed from the injured tissue being treated prior to the occurrence of deleterious tissue changes. In a further preferred embodiment, the injured tissue is exposed to the fusion agent for no more than about 5 minutes. After the injured region of the nervous system is treated with the fusion agent, it may be removed by aspiration and the treated site washed with a biowashing solution, such as isotonic Kreb's solution as described in the examples. Excess fusion agent and/or Kreb's solution can then be removed by aspiration.

In another form of the invention, the method may further include administering to the patient or subject an effective amount of a potassium channel blocker. In the case of a direct-contact application of a biomembrane fusion agent, the injured site is contacted with an effective amount of a potassium channel blocker in addition to the biomembrane fusion agent. A variety of potassium channel blockers may be used, including substituted pyridines. Preferred potassium channel blockers include those that improve action potential conduction in injured tissue, including 3,4-diaminopyridine, 4-methylaminopyridine and amidine. In a preferred form of the invention, the pyridine is substituted with an amino group, more preferably at the 4-position of the ring. Moreover, it has unexpectedly been discovered that treatment of an injured mammalian spinal cord with a potassium channel blocker, such as 4-aminopyridine, after treatment with a fusion agent, such as polyethylene glycol, can result in synergistic repair of the spinal cord. For example, compound action potentials (CAPs) increase in conduction when both agents are used by a percentage greater than the sum of the percent increase in conduction of the CAPs when injured spinal cords are treated alone with either the fusion agent or the potassium channel blocker.

Although the injured nervous system may be contacted with the potassium channel blocker prior to or at the same time as treating with the fusion agent, the system is preferably contacted with the blocker after the treatment with the fusion agent. The potassium channel blocker may be applied in a fashion similar to the fusion agent. The amount of the potassium channel blocker effective in treating or repairing the injured nervous system, such as injured mammalian spinal cord, will also similarly depend on the factors mentioned above. When the potassium channel blocker is 4-aminopyridine, it is typically applied at a concentration of about 10-100 ng/ml cerebrospinal fluid and further preferably about 50-100 ng/ml cerebrospinal fluid. After treatment with 4-aminopyridine, it can similarly be removed by aspiration and the lesion site washed with the biowashing agent.

In yet other forms of the invention, the method may include treating the injury with a polyalkylene glycol, as well as with other conventional management compounds and/or compositions. For example, in addition to treatment with a polyalkylene glycol, the injury may be treated with a steroid, such as methylprednisolone.

A wide variety of injuries may be treated in the present invention. In various forms of the invention, the injury may arise from a compression or other contusion of the spinal cord, crushing of the spinal cord or severing of the spinal cord, or anoxia (e.g., stroke), aneurysm or reperfusion.

The efficacy of the treatment may be determined in a variety of ways, including method's which detect restoration of nerve function. For example, restoration or increase in conduction of action potentials, such as CAPs, through the injured site may be used as an indicator that nerve function has at least partially been restored as described in the examples. Nerve function is considered to have been at least partially restored if there is an increase in the conduction of action potentials after treatment. Preferably, the treatment will be conducted sufficiently to achieve at least about 10% increase in conduction of CAPs. Moreover, restoration of anatomical continuity may also be observed by examination with high-resolution light microscopy and/or by diffusion of intracellular fluorescent dyes through the repaired nervous tissue, such as repaired axons, or by direct observation of repaired axonal membranes. Additionally, in human applications, the efficacy of preferred treatments may be observed by the restoration of more than one spinal root level as determined by the American Spinal Injury Association (ASIA) motor score and/or the National Animal Spinal Cord Injury Study (NASCIS) score as know in the art and as described in Wagih et al., (1996) Spine 21:614-619. Furthermore, in veterinary applications, behavioral analysis of the cutaneous trunci muscle (CTM) reflex, as more fully discussed in the examples, may also be used to determine the efficacy of the treatment, and whether nerve function has at least partially been restored. Using this analysis, nerve function is considered to have been at least partially restored if there is an increased reflex behavior after treatment, but treatments are desirably preferred so as to achieve at least about a 10% increase in the area of CTM behavioral recovery.

In yet other aspects of the invention, compositions for treating an injured nervous system of a vertebrate are provided. The compositions are designed to at least partially restore nerve function as described below. In one form, a composition includes a biomembrane fusion agent and a potassium channel blocker. Although a wide variety of biomembrane fusion agents and potassium channel blockers that are mentioned above may be included in the composition, a preferred biomembrane fusion agent is a polyalkylene glycol and a preferred potassium channel blocker is a substituted pyridine. In more preferred forms of the invention, the polyalkylene glycol is polyethylene glycol and the potassium channel blocker is an amino-substituted pyridine, such as 4-aminopyridine. The composition may be in a pharmaceutically acceptable carrier as described above.

Although the methods and compositions of the invention are useful in treating a wide variety of vertebrates, they may be advantageously used to treat mammals and preferably humans. Moreover, although the methods and compositions are advantageously and surprisingly useful in treating the spinal cord, they may also be used in treating the peripheral nervous system and/or central nervous system, or other areas in which damaged axons are present.

Reference will now be made to specific examples illustrating the compositions and methods described above. It is to be understood that the examples are provided to illustrate preferred embodiments and that no limitation to the scope of the invention is intended thereby.

EXAMPLE 1

Acute In Vitro Response of Crushed Spinal Cord to PEG

This example demonstrates that compound action potentials are restored in a compressed spinal cord in vitro after it is treated with PEG.

In Vitro Isolation of the Spinal Cord

Adult female guinea pigs of 350-500 gram body weight were used for these studies. The spinal cord was isolated from deeply anesthetized animals [(60 mg/kg ketamine hydrochloride, 0.6 mg/kg acepromazine maleate, and 10 mg/kg xylazine, intramuscularly (i.m.)]. Following anesthesia, the animal was perfused transcardially with cold (1 50 C) Krebs' solution (NaCl, 124 mM; KCl, 2 mM; $KH_2PO_4$, 1.2 mM; $MgSO_4$, 1.3 mM; $CaCl_2$, 11.2 mM; dextrose, 10 mM; $NaHCO_3$, 26 mM; sodium ascorbate, 10 mM; equilibrated with 95% $O_2$, and 5% $CO_2$). The vertebral column was rapidly removed using bone forceps and scissors by previously described techniques [Shi, R. and Blight, A. R. (1996) J. of Neurophysiblogy, 76(3):1572-1579; Shi, R. and Blight, A. R. (1997) Neuroscience 77(2):553562]. The spinal cord was divided into four longitudinal strips, first by midline sagittal division, then by separating the dorsal and ventral halves with a scalpel blade against a plastic block. Only the ventral white matter was used for this study. These 35-38 mm long strips of spinal cord white matter will usually be referred to below as "cords" or "spinal cords" for ease of description. Spinal cords were maintained in continuously oxygenated Krebs' solution for an hour before mounting them within the recording chamber. This was to ensure their recovery from dissection before experiments were begun.

Double Sucrose Gap Recording Technique

Figure 1B:
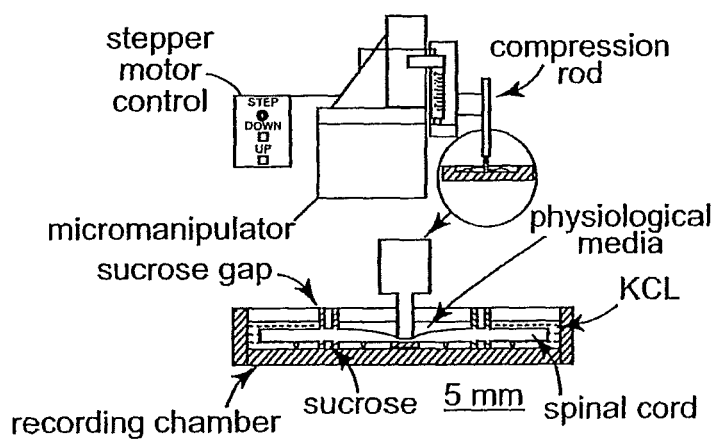

The double sucrose gap recording chamber is shown in FIGS. 1A and 1B and has already been described in previous publications [Shi, R. and Blight, A. R. (1996) J. of Neurophysiology, 76(3):1572-1579; Shi, R. and Blight, A. R. (1997) Neuroscience 77(2):553-562]. Briefly, the strip of isolated spinal cord white matter was supported in the three-compartment chamber. The central compartment was continuously superfused with oxygenated Krebs' solution (about 2 ml/min) with a peristaltic pump. The compartments at both ends were filled with isotonic (1120 mM) potassium chloride, and the gap channels with 230 mM sucrose. The white matter strip was sealed on either side of the sucrose gap channels with shaped fragments of glass coverslips that also blocked the flow of fluid in the narrow gap between the coverslip and the tissue surface. Note that the central chamber is at ground potential for recording. The sucrose solution was run continuously through the gap at a rate of 1 ml/min. Axons within the spinal cord strip were stimulated and compound action potentials (CAPS) were recorded at the opposite end of the white matter strip by silver-silver chloride electrodes positioned within the side chambers and the central bath as shown in FIG. 1B. Specifically, action potentials were stimulated at the left side of the spinal cord strip as shown in the figure, conducted through the spinal cord in the central compartment (also including the injury site), and recorded at the right side of the spinal cord strip as shown. Stimuli were delivered through stimulus isolation units in the form of 0.1 msec constant current unipolar pulses. A conventional bridge amplifier with capacity compensation (Neurodata Instruments) was used to amplify the signal. This data was digitized and stored on video tape with a Neurodata Instruments Neurocorder for subsequent analysis. During the experiment, the oxygenated Krebs' solution continuously perfused the isolated spinal cord tract, while temperature was maintained at 37° C.

Every electrophysiological test was digitized in real time and captured to the computer for subsequent quantitative evaluation. All records were also recorded on VHS magnetic tape as a means of back up documentation. All solutions used in the PEG repair process were made on the day of their use.

The Compression Injury

A standardized compression injury was produced with a stepper-motor controlled rod which compressed the spinal cord while suspended inside the recording chamber (FIG. 1B). Briefly, the isolated white matter strip was compressed against a flat, raised plastic, plexiglass stage at the center of the recording chamber with the flattened tip of a plexiglass rod. The tip was advanced downward to contact the tissue at a standardized rate of about 25 pm/s. The downward movement of the rod was controlled with a stepper motor to produce a finely graded crush just sufficient to eliminate all CAP propagation (which was monitored continuously during the procedure). The end of the rod with the flattened tip provided a compression surface of 2.5 mm along the length of the tissue, and a transverse width of 7 mm, such that it was always wider than the spinal cord strip, even under full compression. Positioning of the compression rod was accomplished with a micromanipulator. CAPs were simultaneously recorded during the injury process. Compression was stopped when CAPs were completely eliminated. The state of complete CAP failure was maintained for an additional 15 seconds before the rod was rapidly withdrawn from the cord's surface to relieve pressure. The recovery of the CAP was then documented. The basic recovery profile following such standardized compression in normal Krebs' solution has been previously characterized and published [Shi, R. and Blight, A. R. (1996) J. of Neurophysiology, 76(3):1572-1579]

PEG Repair Procedure

The PEG repair procedure included the following steps:

1) Typical physiological functioning of the isolated white matter strip removed to the recording chamber required about ½ to 1 hour of incubation time while immersed in oxygenated Krebs' solution to stabilize. In initial experiments, once the CAP propagation had stabilized, the Krebs' solution was replaced with $Ca^{2+}$-free Krebs' ($Ca^{2+}$ replaced with an equimolar amount of $Mg^{2+}$).

2) The spinal cord strip was then crushed by the techniques described above, while simultaneous stimulation and recording continued.

3) A solution of PEG in distilled water (50% by weight) was applied by a pressure injection through a micropipette. A vital dye was added to the PEG solution to monitor its continuous application to the lesion site in a stream about 0.5 mm wide for about 1-2 minutes. The PEG was applied to one side of the lesion, washed over it, and immediately removed by constant aspiration on the other side using a second pipette.

4) Immediately following the PEG application, the bathing media in the central chamber was replaced with a continuous stream of oxygenated normal Krebs' solution. The physiological properties of the PEG-treated spinal cord were monitored continuously for 1 hour. Usually, a weak recovering CAP was evident within 6-15 minutes of the PEG application.

The above-described technique should be considered as a basic one, from which testing of several variations described below was performed. For example, tests were made of the response of "recovering" axons to the additional application of the fast potassium channel blocker, 4 aminopyridine (4-AP). In this trial, 5 separate cords were treated with an application of PEG as described above and compared to 5 control cords. One hour after compression, 100 pM 4-AP (in Krebs' solution) was applied for 15 minutes and then washed free with normal Krebs' solution as described above.

In a final series of experiments, a determination of whether it was necessary to carry out the methods of the present invention in $Ca^{2+}$-free media was made. In these experiments, the cord was compressed while R was immersed in normal Krebs' solution.

Statistical Treatment

Before and after the application of 4-AP, Student t tests were used 20 to compare recovering action potential, amplitude between the control and PEG-treated group. Comparisons of action potential amplitude were also made between the two PEG-treated groups.

Results

PEG-Mediated Repair of Crushed Spinal Cord Strips

Figure 2:
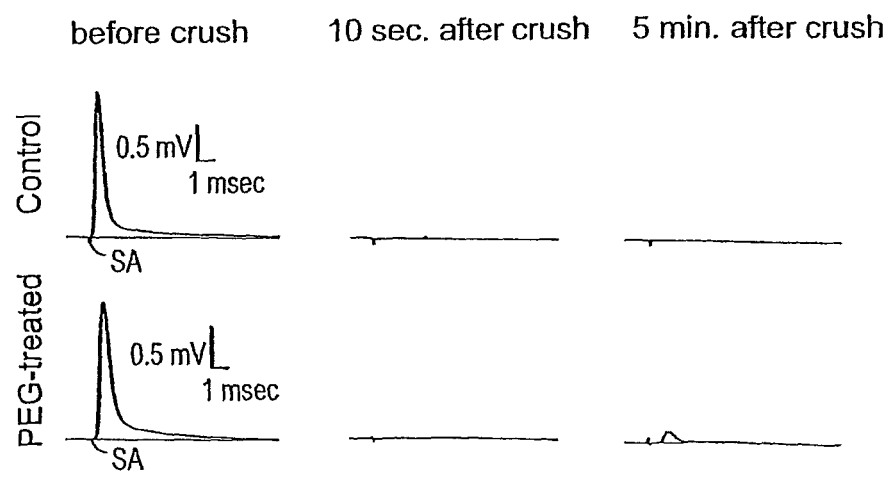

Approximately ½ hour following the equilibration of the spinal cord strip in the recording chamber, the Krebs' solution in the central compartment was replaced with a $Ca^{2+}$-free Krebs' and the spinal cord was crushed by previously described techniques. In every spinal cord tested in this group of twenty (ten control and ten experimental), this procedure resulted in the immediate and total loss of CAP propagation from the point of stimulation to the point of recording. FIG. 2 shows an individual record of one typical control experiment and a PEG-treated experimental spinal cord strip. Note the immediate and complete loss of the CAP in both preparations, and the initial recovery of the CAP in the PEG-treated spinal cord by 5 minutes post treatment (FIG. 2, lower panel). Note that at the earliest time point (about 5 minutes post injury) seen in FIG. 2, recovery of a CAP is never observed in the absence of PEG treatment and rarely occurs by 10 minutes post injury (latter data not shown). The earliest recorded recoveries of a CAP occurred within 1-2 minutes following PEG treatment. In control preparations, 3 cords never regained conduction during the 1 hour of continuous observation. In contrast, not one PEG-treated spinal cord providing the data summarized in FIG. 3 failed to recover CAP conduction following PEG treatment. In four more control spinal cords, the recovery of the CAP was not observed for approximately twenty minutes.

Figure 3:
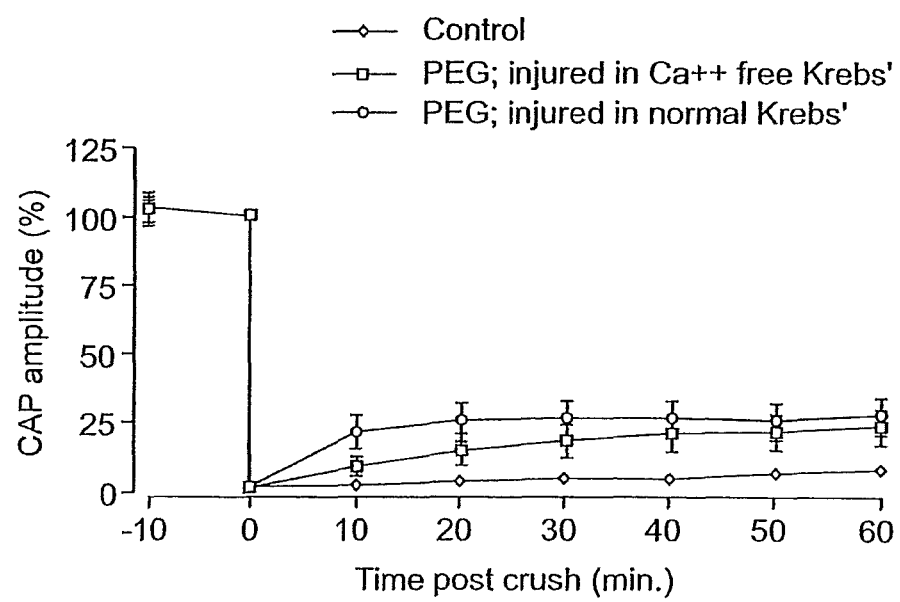

FIG. 3 provides a summary graph of the 10 control and the 10 experimental spinal cords treated and monitored identically, except for the experimental application of PEG to the lesion site. Note that the control group shows a barely detectable CAP (3.6%) even by 1 hour post injury, while average recovered CAPs in PEG-treated cords increase approximately −19%, ranging to as much as 69% of the pre-crush amplitude. PEG treatment always (1) provided a striking increase in the amplitude of recorded CAPs, averaging 19% of the original pretransection amplitude and (2) facilitated the CAP recovery in 100% of the cases tested. At every time point tested, including the 10 minute post injury period, recovered CAP amplitudes were statistically significantly greater than control preparations ($P<0.05$, Student's t test, two-tailed). CAP recovery was facilitated when the injury was not carried out in $Ca^{2+}$-free Krebs' solution. The amplitude of the recovered CAP in normal Krebs' at the first time point (10 minutes post injury) was statistically elevated over the recovered CAP observed when the injury was performed in $Ca^{2+}$-free media ($P<0.05$; unpaired Student t test). Every subsequent time point was still higher in this data set with no reverse trends, but without statistical significance. Thus, it is seen in FIG. 3 that the injury need not be carried out in $Ca^{2+}$-free media to produce functional repair as claimed by Bittner for invertebrate axons [Krause, T. L. and Bittner, G. D. (1990) PNAS 87:1471-1475].

Electrophysiological Properties of the Repaired Spinal Cords

The PEG-repaired spinal cords showed typical conduction properties (as observed in recovering untreated cords) however some differences in their electrophysiological properties were revealed by further evaluation.

Figure 4A:
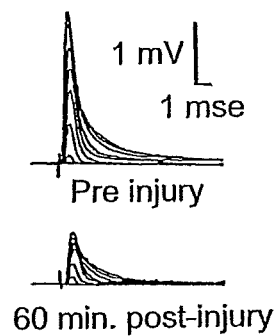
FIGS. 4A-4D depict analyses of the CAP amplitude as a function of increased strength of stimulus in control and PEG-treated spinal cords.
Figure 4B:
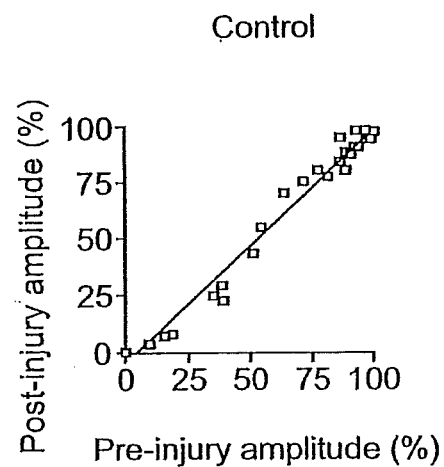

FIG. 4A shows the effect of injury on the normal recovery of CAP amplitudes. Typically, the recovered CAP was dampened in amplitude across all threshold intensities of excitation. It was also evaluated if this reduced magnitude of the CAP occurred across all caliber spectra of injured axons within the spinal cord strip, or was manifest in only large or small diameter axons. FIG. 4B shows the actual amplitudes of control compound potentials at 1 hour post injury, plotted against the preinjury amplitude at the same stimulus intensity. A less severe injury was required in these spinal cords to allow an adequate range of recovered CAP amplitudes, for this graded evaluation. In the severely injured cords, the maximal recovered CAPs were insufficient to adequately make these comparisons. These data points are shown relative to the maximum amplitude achieved prior to and after injury. A least squares linear regression was not significantly different from 1:1 linearity, suggesting that there was no difference between the susceptibility to damage of axons of different stimulus thresholds.

Figure 4C:
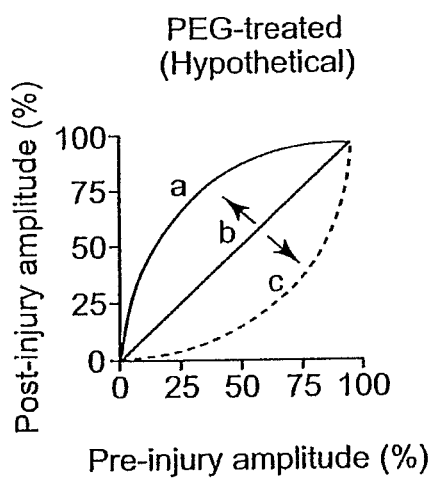
Figure 4D:
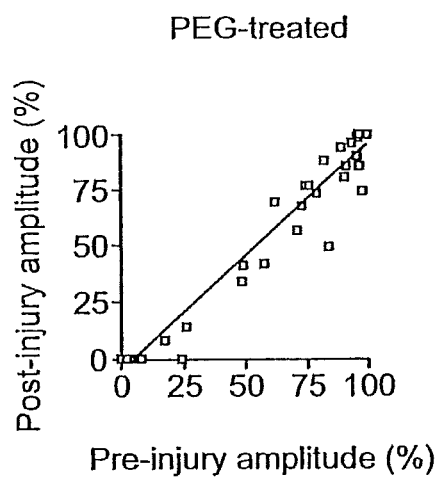

In FIG. 4C, two hypothetical lines are plotted, representing outcomes following PEG treatment. Note that if larger axons of a lowered stimulus threshold were more susceptible to PEG, the data would be shifted as in line (a). In the opposite situation, the hatched line (c) shows a shift in the opposite direction should small caliber axons with a higher stimulus threshold be repaired. In FIG. 4D, the actual data taken from the PEG treated population is plotted in the same manner as in FIG. 4B. Note that the least square linear regression line is not significantly different from 1:1 linearity, which is again not different from that shown in FIG. 4B. The near unity slope of the relation of amplitude response before and after injury indicated no consistent selectivity of PEG-mediated improvement of conduction in fibers of lower or higher threshold. In this test, the typical and severe standardized injury was used, since PEG-repaired cords showed substantial CAPs sufficient for a graded plot of their amplitudes.

Although PEG appeared to be able to repair axons of a wide range of calibers similar to the natural recovery process observed in control cords, the electrophysiological properties of PEG-mediated recoveries was not the same as controls. FIG. 5A shows the classical relationship between the timing of paired stimuli and the amplitude of the two elicited CAPs. Paired stimuli in which the interstimulus interval was between 0.6 to 15.0 ms demonstrated typical dampening of the CAP amplitude soon after the absolute refractory period. When the interval between the paired stimuli was longer than this, a plateau was reached where the first and second CAPs were of an identical magnitude, marking the extent of the relative refractory period.

FIG. 5B shows control data derived from 4 separate experiments. The abscissa shows the magnitude of the second CAP of the pair as a percent of the magnitude of the first elicited CAP. The ordinate shows the log of the interstimulus interval ranging from 0.6-15 ms. This sigmoidal plot is typical, beginning with stimuli that do not elicit a second AP during the absolute refractory period, and ending at the termination of the relative refractory period.

Furthermore, FIG. 5B shows that this relationship was not disturbed by the injury, as pre- and postinjury data points were not significantly different along this sigmoidal curve. This did not hold true, however, for PEG-treated spinal cords. The early and robust recovery of CAPs produced by PEG demonstrated a typical period of absolute refractory as before the injury and experimental treatment. Furthermore, the relative refractory period also appeared to terminate when a similar stimulus interval to control preparations was achieved. During the refractory period of PEG-treated cords, the amplitude of the second CAP was slightly reduced when compared to that before the crush and PEG treatment (FIG. 5C). However, this latter relationship was not statistically significant.

EXAMPLE 2

Potassium Channel Blockade as an Adjunct to PEG-Mediated Recovery of Conduction

This example shows that treatment of injured spinal cords in vitro with both a potassium channel blocker and a biomembrane fusion agent allows synergistic recovery of CAPs.

It is a common feature of injured cells to loose intracellular potassium to the extracellular milieu through compromised membrane. In axons, this may be sufficient to suppress action potential conduction. Thus, it was attempted to determine if blockage of fast potassium channels with 4-AP would affect the properties of conduction immediately following PEG repair.

Spinal cords were crushed, isolated and treated with PEG as described in Example 1. Analysis was also performed in the double sucrose recording chamber as described in Example 1.

Figure 6A:
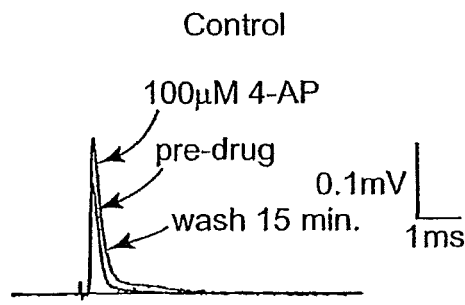
FIGS. 6A-6B depict electrophysiological recordings showing CAPs of control, and PEG/4-AP treated spinal cords.

FIG. 6A shows the enhancement of the CAP in crushed (but untreated with PEG) spinal cord by 4-AP. In this individual record, the initial recovered CAP at 1 hour post injury is shown, and the enhanced CAP following 100 pM 4-AP treatment is superimposed upon it. Following documentation of the 4-AP enhanced CAP, the blocker was washed out, and the media in the central compartment was replaced with normal Krebs' solution. The CAP fell to pretreatment levels by 15 minutes and was indistinguishable from the original record. This final waveform is superimposed on the other two CAPs in FIG. 6A but cannot be discriminated from the pretreatment electrical record. In this single test, 4AP reversibly enhanced the recovered CAP by about 40%.

Figure 6B:
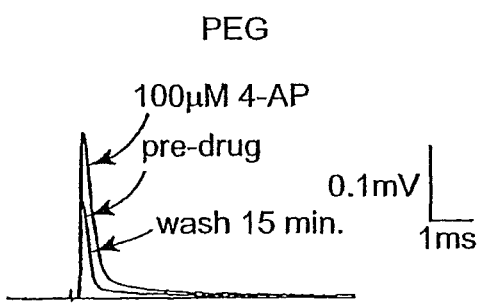

FIG. 6B shows an identical test performed on a PEG-treated spinal cord, in which 4-AP was administered at 1 hour post PEG application. In this individual test, the second CAP was reversibly enhanced by about 70%.

Following the near doubling of the CAP, 4-AP was washed out as described, and the CAP fell to pretreatment levels as in controls (FIG. 6A).

Figure 6C:
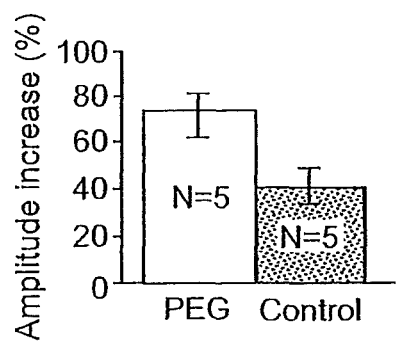
FIG. 6C is a bar graph of group data showing percent amplitude increase for 5 control and 5 PEG-treated spinal cords.

FIG. 6C shows the group data, including 5 spinal cords in each group. The percent enhancement of the PEG-mediated recovery for the group data mirrors that discussed above for the individual experiments (about 70% enhancement in the experimental group; about 40% in the control group). This experimental enhancement was statistically significantly greater than that observed in the controls. ($p<0.05$, unpaired Student's t test)

Figure 7:
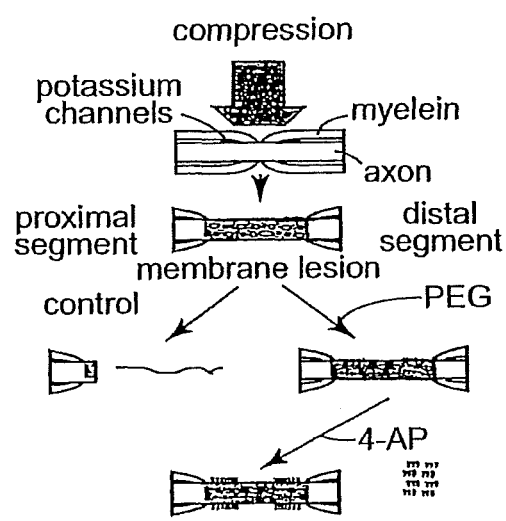

Although not being limited by theory, FIG. 7 depicts a proposed mechanism of the synergistic effect of PEG and 4-AP. A severe mechanical compression of a myelinated axon is diagrammed at the top. Note that the myelin sheath envelops high densities of fast W channels clustered at the paranodal region. Severe crush leads to an exposure of the potassium channels of the paranodal region by a withdrawal or collapse of the myelin lamella at this site [Shi, R. and Blight, A. R. (1996): Neuroscience, 77:553-562]. Exposure of the voltage gated potassium channels after injury would elevate $K^+$ conductance further impeding conduction across this damaged portion of the membrane (gray region showing "holes" in the compromised membrane). In control preparations, partial to complete conduction block results from this localized disturbance of the axolemma, which may progress to complete separation of the axon and loss of the distal axonal segment by Wallerian degeneration (left side of FIG. 7). In PEG-treated axons (right side of FIG. 7), the membrane repair leads to preservation of injured axons as well as improvements in their conduction capabilities (gray regions; membrane holes now sealed). However, elevated $K^+$ conductance through $K^+$ channels that are still exposed at the site of repair in PEG-treated nerve fibers might still suppress conduction to some extent. Blockade of these channels with 4 AP (FIG. 7, small arrow heads; lower right) would be expected to reduce any outward $K^+$ conductance and thus enhance conduction.

Summary of Results

Within a few minutes after the application of the water-soluble polymer PEG, an immediate recovery of CAP propagation through the lesion occurred. The recovered CAP amplitude slowly increased with time to a peak of about 20% of the initial CAP amplitude. Moreover, this level of recovery a) was always statistically significantly higher than control amplitudes, b) was observed at every time point tested, and c) occurred in 100% of the experimentally treated spinal cords. It is clear that a topical application of PEG can immediately repair severe compression injury to the mammalian spinal cord leading to significant increases in functional recovery as defined by the enhanced capacity to propagate nerve impulses through the lesion. This report is the first to demonstrate PEG-mediated repair of crushed mammalian nervous tissue.

We have shown that a physiological, balanced media and the aforementioned PEG solution, is all that is required to produce functionally significant repair in mammalian spinal cords (see below). Moreover, in other experiments, where completely transected guinea pig spinal cords were fused with PEG, it has been revealed there was no specific PEG molecular weight critical to the process, having tested PEG solutions using 400, 1400, 1800, 2000, and 3700 daltons (unpublished observations).

In this physiological study, similarities and differences between the natural mechanisms of axonal repair and those mediated by PEG have been determined. First, a least squares linear regression analysis of preand postinjury CAP amplitudes suggests that PEG-mediated repair can occur across all levels of stimulus thresholds, reflecting axon diameters, as does the natural recovery process in untreated spinal cord strips. In other words, all spinal axons regardless of their caliber are equally susceptible to PEG mediated repair [see Shi, R. and Blight, A. R. (1996) Neuroscience 77:553-562 for a similar analysis of axonal recovery from compression injury]. The differences between natural repair and that produced by PEG application are more striking. First, this injury is very severe; 30% of control spinal cords never recovered any capacity to conduct CAPs during the 1 hour period of evaluation following injury. On the other hand, there was no instance where PEG did not initiate a measurable physiological recovery. On a more subtle level, there appears to be a slightly reduced CAP amplitude during the period of relative refractory in only PEG-mediated CAPs relative to control cords. One explanation for this observation may be that in control cords a severely compromised and dysfunctional population of axons may become completely nonfunctional, revealing more normal conduction properties in that population that survive the injury. PEG may rescue a portion of such severely compromised axons, recruiting them into the CAP, and perhaps accounting for its slightly different conduction properties.

The above-described in vitro evaluation of the anatomy of axonal repair following mechanical compression has revealed that a 2 minute application of PEG produced sealing of membrane lesions at the site of a standardized compression. Sealing was indicated by the exclusion of horseradish peroxidase uptake by injured fibers in the PEG-treated group compared to sham-treated spinal cords (J. Neurocytology, 2001, in press). Such immediate repair of membrane breaches sufficient to inhibit the uptake of large molecular weight dyes should also arrest or reduce permeabilization, allowing the nonspecific flux of ions across it. Although not being limited by theory, it is believed that this "sealing" behavior of PEG both restores excitability and reverses anatomical dissolution of the nerve fiber.

This procedure may advantageously applied to treat severe, acute neurotrauma. In addition to immediate improvements in conduction, repair of crushed axons in peripheral nerves leading to a rescue of their distal segments would provide the added benefit of reducing atrophy or degeneration of target cells or so called "end organs." Moreover, PEG-mediated fusion of even transected axons could become a component of microsurgical grafting techniques since the conventional resection of peripheral nerve trunks prior to fascicular grafting exposes the severed tips of proximal and distal axonal segments, making them available for fusion.

EXAMPLE 3

Effect of PEG on Restoration of CAPs in Severed Spinal Cord Axons

This example demonstrates that severed spinal cord axons may be fused with PEG, thus allowing restored conduction of CAPs through the lesion site.

In Vitro Isolation of Spinal Cord

The spinal cord of adult female guineas pigs was isolated according to the protocol of Example 1. After the cord was isolated, it was halved by midline sagittal division. The ventral white matter was separated from gray matter with a scalpel blade against a soft plastic block. Cords were maintained in continuously oxygenated Krebs' solution for at least an hour before mounting in the recording chamber. This was to ensure the recovery from dissection before each experiment was begun.

Double Sucrose Gap Recording Technique

The technique was followed according to the protocol in Example 1. The central bath was connected to instrument ground. The entire chamber was mounted on a Peltier temperature control system, which also maintained the entire preparation at 37⁰ C. Thermistors, in the chamber next to the spinal cord, constantly recorded and displayed the temperature. After mounting the spinal cord in the sucrose gap chamber, recorded CAPs and compound membrane (Gap) potentials usually stabilized with an hour [Shi, R. and Blight, A. R. (1996) J. of Neurophysiology, 76(3):1572-1579; Shi, R. and Blight, A. R. (1997) Neuroscience 77(2):553-562]; Shi, R. and Borgens, R. B. (1999) J. Neurophysiblogy, 81:2406-2414.

PEG Fusion Procedure

The basic methodology used to fuse spinal axons was as follows:

1). Restoration of typical physiological functioning of the isolated white matter strip removed to the recording chamber required about ½ to 1 hour of incubation time while immersed in oxygenated Krebs' at 37° C. Once both the Gap potential and CAP propagation were normal, the spinal cord strip was transected.

Figure 8:
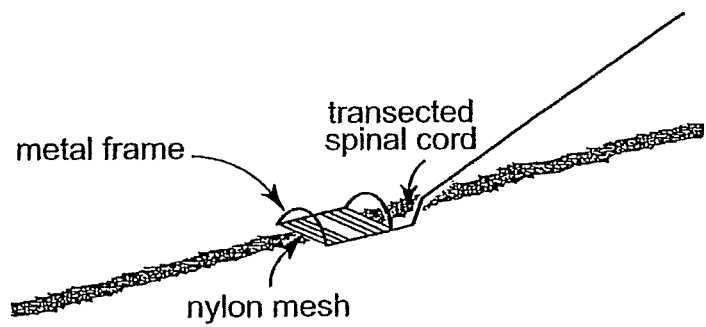
Figure 10A:
FIGS. 10A-10D show fluorographs of adjacent transected surfaces of a transected strip of guinea pig spinal cord white matter facing each other across a gap. About 1.5 μl of FIR was injected into segment A, and revealed using excitation/barrier wavelengths of 545/590 nm, respectively, in darkfield. The adjacent segment in B, illuminated with the same excitation and barrier filter combination, was injected with FE. Note the absence of FIR filled axons in B. Images C and D are identical views to A and B, only illuminated with excitation/barrier wavelengths of 495/515 nm sufficient to reveal only the FE labeled axons seen in D. Note that in these control preparations, as in all unfused regions of spinal cords, dye labeled axons are never visualized in the segment of spinal cord not originally injected. The dashed lines show the approximate boundaries of a projection of dye labeled axons from their site of injection (out of the photographic field) to the plane of transection. Scale bar for A, B, C, and D=500 μm.
Figure 10B:
Figure 10C:
Figure 10D:
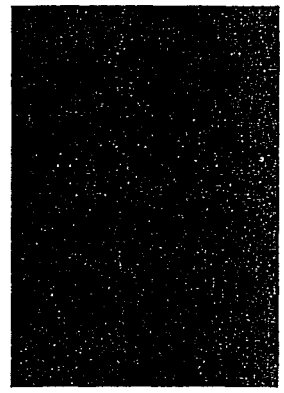

2). The spinal cord strip was completely severed with a laboratory fabricated cutter (a shard of a razor blade attached to an applicator stick), and the two ends of the spinal cord were observed to be separated by a gap of about 0.5-1 mm with a stereomicroscope. The spinal cord was transected within the middle of the central compartment of the recording chamber. Stimulation and recording were continued during this operation. Following transection, the two ends of the cord segments were "pushed together," i.e., abutted tightly using a watchmaker forceps and a laboratory fabricated device that applied gentle pressure on one segment of the spinal cord strip pressing and holding it against the other. The device was mounted on a micropositioner, and contacted the spinal cord parenchyma with a strip of nylon mesh stretched across two metal bands (FIG. 8). The metal frame of the device never contacted the spinal cord tissues during use. Only the nylon mesh was in contact with the tissue. Several methods to accomplish stabilization during the fusion process were tested, the most effective involved first lightly placing the mesh onto the intact cord. Once this was accomplished, the spinal cord strip was completely transected, with a gap appearing between the two segments which were then repositioned as discussed above.

3). Various solutions of PEG (1400, 1800, 2000, and 3500 daltons, 50% by weight in distilled water) were applied by pressure injection through a micropipette in preliminary experiments (data not shown), while the data reported here exclusively utilized PEG of having a molecular weight of about 1800 daltons. A vital dye was added to the PEG solution to monitor its application to the lesion site as a continuous stream about 0.5 mm wide and continuing for about 1-2 minutes. The PEG was applied to one side of the lesion, washed transversely across it, and was removed by constant aspiration on the other side using a second suction pipette.

4). During the PEG application; a continuous stream of oxygenated Krebs' solution was maintained. The electrophysiological properties of the spinal cord following PEG treatment was monitored continuously for approximately 1 hour.

Results

Typical CAPS were recorded in response to stimulation, and were completely eliminated following transection of the cord between the stimulation and recording electrodes in every spinal cord strip tested (FIGS. 9A and 9B). The recovery of CAPs was often observed within 5-15 minutes following PEG application and continued for up to 60-80 minutes, at which time physiological recordings were discontinued (FIGS. 9C and 9I). Since the conduction of CAPs across the plane of transection does not occur in severed spinal cords, a fusion was defined as successful if a restored CAP was detected demonstrating properties of latency and stimulus threshold. In preliminary experiments, it was discovered that the success of an attempted fusion depended on the alignment and the care taken during abutment of the spinal cord segments prior to PEG application. The ends of the strips cannot be too tightly forced together or this produces more injury to the spinal cord. They cannot be too loosely abutted or fusion of the axolemmas will not take place (see below). All 20 of the attempted fusions reported here were successful. Recovered CAPS were on the order of 5% of the peak magnitude of the original pre-transection CAPs. Note that the computer managed data acquisition techniques used in to obtain physiological recordings shown in FIGS. 9A-9I have been previously reported [Shi, R. and Blight, A. R. (1996) J. of Neurophysiblogy, 76(3):15721579; Shi, R. and Blight, A. R. (1997) Neuroscience 77(2):553-562]

Table 1 below provides the quantitative data derived from an evaluation of 20 successful fusions using 1800 dalton PEG. In preliminary experiments, identical, functional fusions were achieved in a few cases using 1400, 2000, and 3500 dalton PEG (data not shown).

across the original transection. Moreover, the restored anatomical continuity is shown to be correlated with the restored ability to conduct CAPs.

Tract Tracing with Intracellular Fluorescent Probes

Intracellular injections of two fluorescently decorated dextrans were used to evaluate the integrity of formerly transected nerve fibers by procedures previously described [Borgens, R. B. and Bohnert, D. M. (1997) Exp. Neurol. 145:376-389]. Briefly, injections of about. 1-1.5 µl of one tracer, tetramethylrhodamine dextran or Fluororuby (FIR, 8000 dalton, Molecular Probes Inc.), was made to one segment of the fused cord, approximately 4-6 mm from the original plane of transection. This label was observed with excitation/barrier wavelengths of 545/590 nm respectively, in darkfield. Likewise, a second and similar injection of another tracer, FITC conjugated dextran or Fluoroemerald (FE, 8000 dalton, Molecular Probes, Inc.) was made to the opposite segment and observed with excitation/barrier wavelengths of 495/515 nm, respectively. Approximately 12-14 hours later the cords were immersion fixed in 5% glutaraldehyde/0.01% paraformaldehyde. This time period allowed the intracellular markers to diffuse throughout axons. During this incubation period, a continuous flow of oxygenated Krebs' solution was maintained through the central compartment of the recording chamber, which helped to eliminate any extracellular diffusion of the dye. Longitudinal horizontal sections (about 15-30 µm) of the spinal cord strips were made on either a freezing microtome or the tissue was imbedded in paraffin for sectioning by conventional histological technique. Each of these dyes was viewed independently using the appropriate barrier and filter combinations in fluorescent darkfield. These operations were performed on 8 PEG-treated, and fused spinal cord strips. Additional control procedures were performed on 5

TABLE 1

Characteristics of 20 successful fusion of mammalian spinal cord axons utilizing 1800 dalton PEG.

| | AP amplitude | | | | | Peak latency (ms) | | | | | ½ Height Duration (ms) | | | | |
|---|---|---|---|---|---|---|---|---|---|---|---|---|---|---|---|
| Exp#[1] | Pre[2] | post[3] | (%)[4] | SEM[5] | range[6] | pre | post | (%) | SEM | range | pre | post | (%) | SEM | range |
| 20 | 2.44 | 0.44 | 4.61 | 2.83 | 0.2-58.0 | 0.93 | 1.05 | 114.5 | 8.71 | 26-227 | 0.63 | 0.53 | 85.5 | 6.45 | 36-156 |

[1]Total number of fusions carried out at 370 C.
[2]Data obtained before transection.
[3]Data obtained after PEG-mediated fusion.
[4]Mean percent recovery after fusion
[5]Mean standard error after fusion.
[6]Range of data.

A series of control procedures were performed to insure that restored CAP conduction was indeed a function of restored axonal integrity and not produced as an artifact by some alternate means of conduction. For example, CAPs were not conducted across the plane of transection if: (1) subthreshold stimulation was applied to PEG fused cords (20 cases), (2) the original fusion site was again transected with the cutting device (6 cases, FIG. 9 D), (3) spinal cord segments were closely abutted in the stream of Krebs's solution, but PEG was not applied (5 cases, FIGS. 9E and 9F), and (4) PEG was applied to poorly abutted segments (5 cases, FIGS. 9G and 9H).

EXAMPLE 4

Effect of PEG on Anatomical Continuity of Severed Axons

This example illustrates that PEG fuses and repairs severed axons such that intracellular fluorescent dyes may diffuse spinal cord strips to insure that dye did not travel into the opposite segment of the cord from where it was injected. This involved injecting the two dyes into cord segments as previously described; however, these segments were tightly abutted but not fused with PEG.

In another 5 PEG-treated spinal cord strips, high resolution light microscopy was used to evaluate the plane of fusion. These fixed strips of spinal cord were cut to a length of about 5 mm containing the fusion plane, embedded in plastic by conventional methods, sectioned at 0.5-1 micron on an ultramicrotome, and stained with 1% toluidine blue. Microscopic images were captured directly to a Dual Pentium PRO PC from an Olympus Van Ox Universal microscope fitted with an Optronics DEI-750 3 CCD video camera system.

Results

The anatomical continuity of axons that had been fused at the plane of transection was correlated with the restored ability to conduct CAPs in 13 spinal cords. This was determined by the intracellular diffusion of the two different fluorescent dyes across the lesion site in 8 cords and in 5 additional cords by conventional microscopy of plastic imbedded sections. Axons filled with the different dyes were examined independently of each other by fluorescence microscopy with different excitation and barrier filter combinations in darkfield. FIGS. 10A-10D are typical of all 5 control preparations (cord segments tightly abutted but without PEG application) in which the potential of the dye to diffuse from one segment to the other by an extracellular pathway was examined. In all controls, a dye injected into axons of one segment was never observed within axons of the opposite cord segment. This was in part due to the small dye volume injected (about 1.5 µl) coupled to a continuous flow of media through the central compartment of the recording chamber maintained during the entire procedure. This eliminated the spread of dye by an extracellular diffusion path.

Figure 11A:
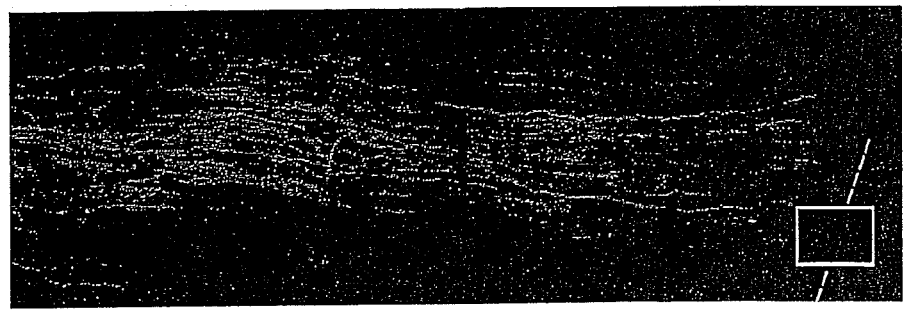
FIGS. 11A-11F depict fluorographs of PEG-fused regions of four separate spinal cords strips that were initially transected, treated with PEG and injected with fluorescent dyes as more fully described in Example 4. The approximate plane of fusion is marked with a dashed line. An PR-labeled projection is shown in FIG. 11A at low magnification. The rectangle in FIG. 11A circumscribes the region shown in FIG. 11 B at higher magnification. The arrows in FIG. 11 B depict sites where one axon segment appeared to be fused to two others.
Figure 11B:
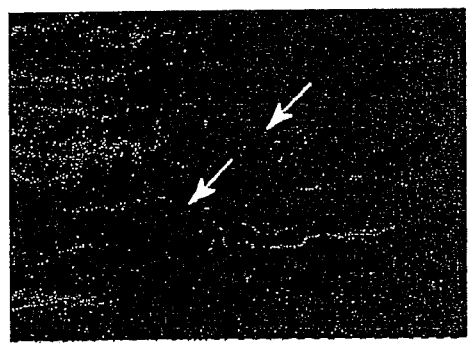
Figure 11C:
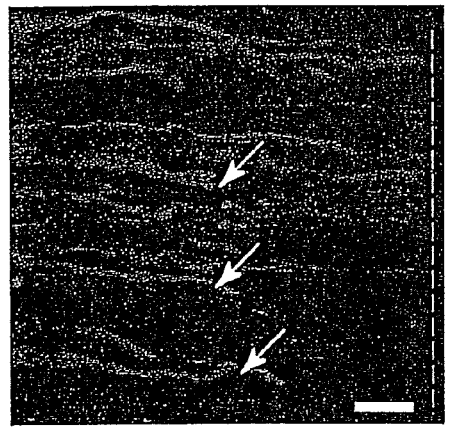
Figure 11D:
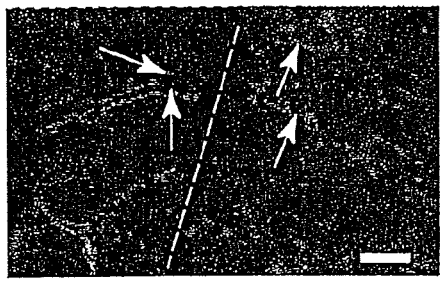

In both control and experimentally fused cords, unfused axons retracted back from the transection plane for a variable distance (50 µm-0.5 mm), their terminal clubs or endbulbs clearly visible (FIG. 11C). The plane of transection was identifiable in PEG-fused cords as a transverse series of gaps and holes interspersed with well-fused regions of spinal cord parenchyma (FIGS. 11A, and 11D-11F). It is believed that such gaps result from partial separation of the fused segments during handling prior to fixation as well as incomplete perfusion of the cord with PEG. Since PEG probably fuses some non-neuronal cells as well as neuronal processes, the original transection plane in well fused expanses of spinal cord was nearly undetectable with fluorescent microscopy sufficient for visualizing the two intracellular dyes. However, blue-violet fluorescent illumination induced some spinal cord auto fluorescence which could reveal the fusion plane in these regions as a very fine "seam".

Figure 11E:
Figure 11F:

In all 8 cords in which tract tracing was performed, a recovered CAP was documented. In 6 of these, fibers filled from either end of the cord traversed the fusion plane into the adjacent segment. In 2 of these 6 strips, only fibers filled with FR crossed the lesion, the FE labeled segments being poorly filled. It was common to observe the terminal ends of unfused axons within a few micrometers of fused axons adjacent to them which filled along their lengths across the original transection (FIG. 11 C). In one case, axons were observed to have fused to two or more others, producing a tangle of nerve fibers within the transection gap (FIGS. 11A and 11 B). This tangle of fibers could also be traced to the opposite spinal cord segment. Additionally, note that the approximate site of dye injection in FIG. 11A is to the left of the image and out of the field of view. In three of the five cords evaluated by high resolution light microscopy, unmyelinated expanses of myelinated axons fused at the original plane of transection (FIGS. 11E and 11F). In these regions membrane and myelin debris could also be seen in the gap surrounding the reattached fibers. Furthermore, in FIG. 11E, the two, re-apposed ends of the white matter strip show continuity over a length of apposition in the middle of the frame. The plane of transection (dashed line) is clear from the slight gaps that remain between the ends of the strip at the top and bottom of the figure, which continue across the whole width of the tissue in the rest of the section (visible at lower magnification).

SUMMARY OF THE RESULTS

Our data show that a water soluble polymer, PEG, can be used to rapidly reconnect the severed halves of spinal axons within completely severed strips of isolated spinal cord white matter. This fusion has been documented by both anatomical and physiological means. In the former, fluorescent intracellular markers were injected into each spinal cord segment. In 6 cases of 8, axonal continuity across the plane of fusion was demonstrated. By searching the fusion plane in plastic embedded sections, unambiguous evidence of axonal fusion in three of five additional spinal cord strips was detected.

In all five control spinal cords, the intracellular label was never observed in the opposite cord segment from where it was injected. This was largely due to the elimination of an extracellular diffusion pathway from the site of injection to the opposite cord segment by the flowing medium in the central compartment and the separation of compartments by the sucrose gap "boundaries". Furthermore, the presence of numerous terminal clubs of transected but unfused axons adjacent to well-labeled axons crossing the transection plane provided additional anatomical evidence that true fusion of severed proximal and distal axon segments had taken place.

The immediate restoration of CAP propagation across the transection plane in completely severed spinal cords following PEG treatment could only have occurred coincident with the functional reconnection of proximal and distal segments of axons. In control spinal cords, CAP conduction did not reappear following tight abutment of the severed segments when PEG was not applied. Furthermore, CAP conduction did not reappear in segments that were poorly abutted by design and also treated with PEG. Thus, PEG itself does not provide some sort of substrate permitting CAP conduction. It is to be concluded that a topical application of PEG indeed functionally reunites severed mammalian nerve processes. This observation compliments and extends the demonstration that topically applied PEG can repair guinea pig spinal cords severely crushed by a standardized procedure leading to an immediate recovery of action potential propagation through the lesion [Shi, R. and Borgens, R. B. (1999) J. Neurophysiol. 81:2406-2414].

EXAMPLE 5

In Vivo Effect of PEG on Restoration of the CTM Reflex in Guinea Pigs with Crushed Spinal Cords This example illustrates that in vivo treatment of crushed guinea pig spinal cords restores the CTM reflex.
Surgery and Anesthesia A total of 51 adult (300 gm) guinea pigs were used in two separate experiments. Guinea pigs were anesthetized with an intramuscular injection of 100 mg/kg ketamine HCL, and 20 mg/kg xylazine, and the spinal cord was exposed by dorsal laminectomy [Borgens, R. B., et al. (1986) J. Comp. Neurol. 250:157-167; Borgens, R. B., et al. (1990) J. Comp. Neurol. 296:634-653]. Subsequently, a constant displacement 15 second compression of the spinal cord was performed using a modified forceps possessing a détente [Blight, A. R. (1991) J. Neurolog. Sci. 103:156-171]. In this experiment, the lesioning procedure had previously been calibrated to produce an immediate and total loss of CAP conduction through the injury and behavioral functioning of the cutaneous trunci muscle reflex (see below). For some SSEP measurements, or to sedate animals for behavioral testing and videotaping, guinea pigs were injected with 0.1 cc Na$^+$ Pentobarbital, 50 mg/ml. Surgery and functional testing were carried out under protocols approved by the Purdue University Animal Care and Use Committee, in accordance with Federal, State, and University guidelines governing animal use in research.

PEG Application

An aqueous solution of PEG (either 400 or 1800 daltons, 50% by weight in distilled water) was applied with a pipette to the exposed injury for two minutes in experimental animals, and then removed by aspiration. As in prior in vitro experiments [Shi, R. et al. (1999) J. of Neurotrauma 16:7277 38; Shi, R. and Borgens, R. B. (1999) J. Neurophysiology 81:2406-2414], no difference in the response to these two solutions was detected, so these data are pooled in this report. The site of PEG application was immediately lavaged with isotonic Krebs' solution (124 mM NaCl, 2 mM KCI, 1.24 mM $KH_2PO_4$, 1.3 mM $MgSO_4$, 1.2 mM $CaCl_2$, 10 mM dextrose, 26 mM $NaHC0_3$, and 10 mM sodium ascorbate), and any excess PEG and/or Krebs' solution removed by aspiration. Although PEG was not applied to the injury in shamtreated animals, the site was lavaged with Krebs' solution which was subsequently removed by aspiration. The wounds were closed, and animals kept warm until awaking with heat lamps. Guinea pigs were housed individually and fed ad libidum.

In the first experiment, it was attempted to repeat the remarkable complete reversal of functional loss within minutes of severe spinal injury as observed in in vitro trials [Shi, R. et al. (1999) J. of Neurotrauma 16:727738; Shir, R. and Borgens, R. B. (1999) J. Neurophysiology 81:2406-2414]. Thus, PEG was applied within about 15 minutes of spinal cord compression (experimental n=14, control n=11). In the second experiment, PEG application was delayed for about 8 hours (experimental n=11, control n=11). The former groups were evaluated for about 4 days, and the latter, for about 1 month, after PEG application. In both experiments, documentation of CTM behavior was combined with physiological recording.

An additional 4 PEG-treated animals were followed for 1 day post injury at which time their spinal cord was again exposed at the site of the original injury and crushed again at this location using the same technique as reported above.

Behavioral Analysis of the Cutaneus Trunci Muscle (CTM) Reflex

The CTM behavior is observed as a corrugated rippling of backskin in response to light tactile stimulation (FIG. 12B). The behavior is dependent on afferent sensory projections organized as a long tract of axons in each ventral funiculus of the spinal cord, just lateral to the spinothalamic tract [Blight, A. R., et al. (1990) J. Comp. Neurol. 296:614633; Thierault, E. and Diamond, J. (1988) J. Neurophys. 60:446-463; Thierault, E. and Diamond, J. (1988) J. Neurophys. 60:463-477].

Specifically, FIG. 12A shows a diagram of the sensory and motor components of the CTM reflex of the guinea pig. Sensory receptors in backskin project afferent axons into each thoracic segment on both sides via the dorsal cutaneous nerves (den). These enter the spinal cord and synapse on second and third order neurons which project their axons (red) to the thoracocervical junction. These tracts of ascending nerve fibers are located on each side of the spinal cord within the ventral funniculus, lateral to the spinothalahmic tract. These ascending axons synapse on bilaterally located pools of CTM motor neurons located between T-1 and C-6. Motor fibers exit the spinal cord on each side as a component of the brachial plexus and innervate the cutaneous trunci muscle of the skin. Note that a spinal cord lesion extending across both sides of the cord compromises ascending tracts, producing a region of backskin areflexia on both sides below the level of the injury. In this region of skin, tactile stimulation no longer elicits skin rippling.

The reflex is bilaterally organized as segmental receptive fields, displays little supraspinal control, and is usually permanently lost following severe spinal injury producing a bilateral region of areflexia below the level of the lesion [Borgens, R. B., et at, J. Comp. NeuraL 296:634-653; Blight, A. R., et al. (1990) J. Comp. Neurol. 296:614-633; Thierault, E. and Diamond, J. (1988) J. Neurophys. 60:446-463; Thierault, E. and Diamond, J. (1988) J. Neurophys. 60:463-477] (FIGS. 12 A and 12C). In such cases, recovery of the CTM reflex in response to tactile or electrical stimulation within the region of areflexia is usually not observed for the life of the animal. The anatomy, physiology, and character of the CTM behavior—both normal and in response to lesioning—has been reported in both rat and guinea pig [Blight, A. R., et al. (1990) J. Comp. Neurol. —296:614-633; Thierault, E. and Diamond, J. (1988) J. Neurophys. 60: 446463; Thierault, E. and Diamond, J. (1988) J. Neurophys. 60:463-477].

To visualize and quantify the CTM behavior, a matrix of dots was marked onto the backskin of the animal. When the shaved backskin of sedated guinea pigs was touched with a monofilament probe, the backskin in uninjured or intact receptive fields contracted in response to the tactile stimulation (FIG. 12B). The boundary between responsive and unresponsive backskin was marked onto the backskin with a marker while the entire study period was videotaped from a platform-mounted camera above. Probing outside this area does not evoke skin contraction.

Animals were arranged on a background grid to facilitate the registration of successive video images. Video images were acquired to an Intel® Dual Pentium® Pro computer. Superimposing of images, the coloring of receptive field boundaries made on the backskin of the animals during CTM testing, and the general management of video images was performed using Adobe® Photoshop® software. Final Plates were constructed with Microsoft® Powerpoint software and printed on an Epson Stylus Color 800 printer. Quantitative planimetry of the unit area of receptive fields—or regions of behavioral loss and recovery—was carried out using IP Lab Spectrum™ software.

Statistics

The Mann Whitney, two-tailed test was used to compare the means of the data derived from experimental and shamtreated groups. To compare the proportions between groups, Fishers exact test was used. All tests were performed using INSTAT software.

Results

The standardized injury produced a similar loss of CTM functioning in experiments testing the response to the immediate application of PEG and experiments testing the response to the delayed application of PEG. The percent loss of CTM receptive fields (FIG. 12C) was not statistically different between either of the two experiments or between sham-treated and PEG-treated guinea pigs in either experiment (P>0.4, Student's t test, two-tailed). Only one animal died during the course of this study.

Behavioral Loss and Recovery of the CTM Reflex

In both experiments, 19 of the 22 sham-treated animals did not recover CTM functioning, as seen in Tables 2 and 3.

TABLE 2

Percent recovery of the CTM[1] reflex in adult guinea pigs after immediate treatment with PEG.

| | Day 1 | | | | Day 2 | | | | |
|---|---|---|---|---|---|---|---|---|---|
| | Animal No. | $\bar{X}\square SEM^2$ | Range[3] | Stat[4] | Animal No. | $\bar{X}\square SEM^2$ | Range[3] | Stat[5] | Stat[6] |
| Control | 0/11 | 0 | 0 | 0.0005 | 2/11 | 0.18 □ 1.9 | −15-11 | 0.015 | 0.006 |
| PEG-Treated | 10/14 | 6.2 □ 1.4 | 0-15.2 | | 10/14 | 13.8 □ 3.8 | 0-42.1 | | |

[1]The increase in the area of backskin regaining sensitivity to tactile stimulation is given as a percent of the total region of CTM behavioral loss. All unit areas in CM2 were calculated by planimetry from captured video images.
[2]F = Mean % Recovery of the CTM Reflex and Standard Error of the Mean
[3]The range of the control data set at 4 days includes the percent increase in the area of CTM loss which is given as a negative number.
[4]P value: proportion of recovered and unrecovered animals evaluated with Fishers' exact test, two-tailed.
[5]P value: means compared with Mann Whitney, two tailed test.

TABLE 3

Percent recovery of the CTM1 reflex in adult guinea pigs after delayed treatment with PEG.

| | Day 1 | | Day 3 | | 2 Weeks | | 1 Month | |
|---|---|---|---|---|---|---|---|---|
| | Animal Number | $\bar{X}\square SEM^2$ | Animal Number | $\bar{X}\square SEM$ | Animal Number | $\bar{X}\square SEM$ | Animal Number | $\bar{X}\square SEM$ |
| Control | 0/11 | 0 | 1/11 | 2.8 □ 2.8 | 1/11 | 2.8 □ 2.8 | 1/11 | 2.8 □ 2.8 |
| PEG-Treated | 9/11 | 11.8 □ 2.9 | 9/11 | 11.9 □ 2.9 | 10/11 | 15.3 □ 3.3 | 10/11 | 19.5 □ 3.02 |
| Statistic | 0.0002[4] | NA[6] | 0.002[4] | 0.009[5] | 0.0003[4] | 0.003[3] | 0.0003[4] | 0.0008[5] |

[1]The increase in the area of backskin regaining sensitivity to tactile stimulation is given as a percent of the total region of CTM behavioral loss. All unit areas in CM2 were calculated by planimetry from captured video images.
[2]X = Mean % Recovery of the CTM Reflex and Standard Error of the Mean
[3]The range of the control data set at 4 days includes the percent increase in the area of CTM loss which is given as a negative number.
[4]P value: proportion of recovered and unrecovered animals evaluated with Fishers' exact test, two-tailed.
[5]P value: means compared with Mann Whitney, two tailed test.
[6]Statistical comparison of means not applicable to this data set.

During the first experiment, CTM functioning actually worsened by day 4 in two control animals (the region of CTM loss increased by 2% and 15% respectively; Table 1). In contrast, CTM functioning recovered in 10 of 14 PEG-treated animals in the first experiment (about 80%; FIG. 12D, Table 2), and in greater than about 90% of experimental animals in the second experiment. In all PEG-treated animals, the restored region of CTM competent backskin was observed within the first day following treatment and continued to increase in size with time (Tables 2 and 3). For example, the average unit area of backskin recovering CTM sensitivity nearly doubled from about 12% (day 1) to about 20% by 1 month post application in the second experiment (Table 3). Both the increased proportion of animals recovering CTM function, and the average increase in the areas of recovered CTM competent backskin in response to PEG, was statistically significant (Tables 2 and 3).

EXAMPLE 6

In Vivo Effect of PEG on Conduction of Somatosensory Evoked Potentials Through Crushed Guinea Pig Spinal Cord This example demonstrates that in vivo application of PEG to an injured spinal cord allows for conductance of evoked CAPS, known as somatosensory evoked potentials (SSEPs), through the region that was injured.
Physiological Recording of SSEPs A pair of subdermal electrodes stimulated nerve impulses from the tibial nerve of the hindleg (stimuli trains in sets of 200 at 3 Hz; stimulus amplitude less than or about equal to 3 mA square wave, 200 Ps duration). Evoked volleys of CAPs were conducted into the spinal cord, projected to, and recorded from, the sensory cortex of the brain. Recording of the nerve impulses at the brain employed a pair of subdermal electrodes located above the level of the contralateral cortex with reference electrodes located in the ipsilateral pinna of the ear. Stimulation, recording, signal averaging, and the computer management of this physiological data utilized a Nihon Kohden Neuropak 4 stimulator/recorder and PowerMac G3 computer.

Figure 13A:
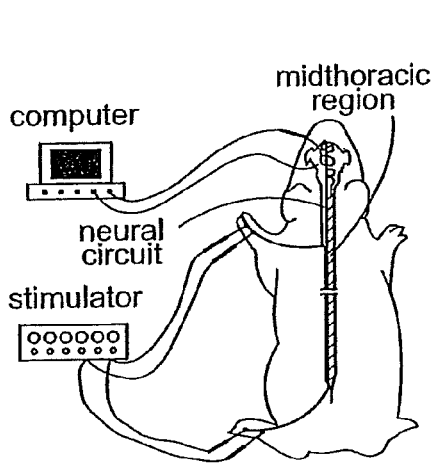
FIG. 13A depicts an experimental setup used in the examples. Nerve impulse pathways were interrupted by crushing the spinal cord in the midthoracic region (red circuit). A control procedure demonstrated that a failure to detect SSEPs was due to a failure of ascending nerve impulse conduction through the lesion by stimulation of a neural circuit unaffected by the injury.
Figure 13B:
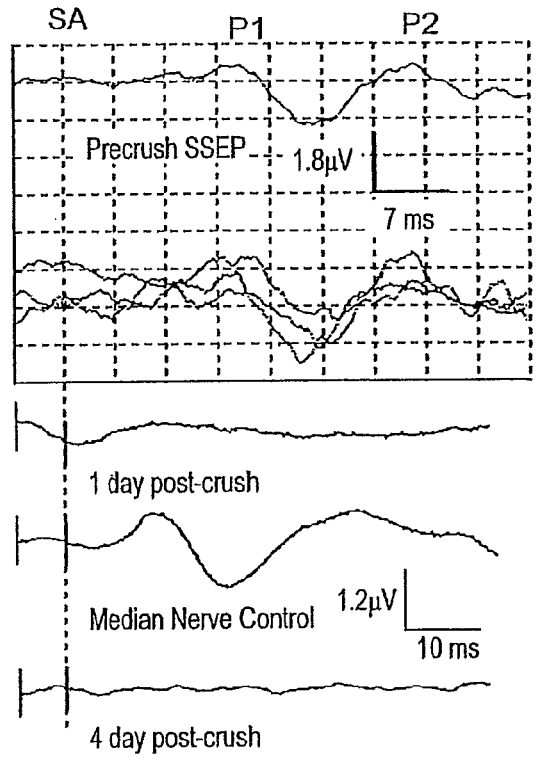
FIGS. 13B-13D depict SSEP electrical recordings. The top panel of FIG. 13B shows a complete somatosensory evoked potential (SSEP) electrical recording in an uninjured guinea pig. The lower panel of FIG. 13B shows the three individual traces used to produce the averaged signal seen in the top panel. SA=stimulus artifact; P1=first arriving SSEP (latency=about 18 ms); P 2=late arriving potentials (latency=about 34 ms). The arrow in the lower panel of FIG. 13B points to a typical SSEP in response to median nerve stimulation, showing interruption in conduction was due to the lesion. Below the median nerve control response, an SSEP in response to tibial nerve stimulation 4 days post-injury is depicted.
Figure 13C:
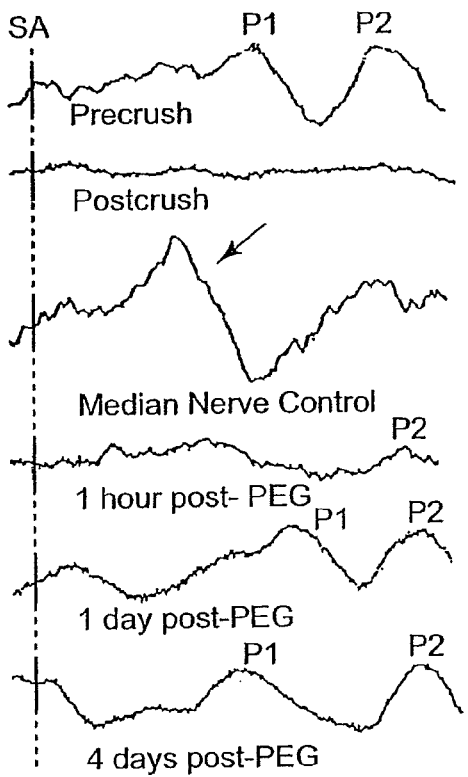

Measurements of SSEPs were carried out in every animal prior to spinal cord injury (FIGS. 13A-13D). In all animals (at any test period), the failure to record an SSEP following stimulation of the tibial nerve was further confirmed to be due to a lack of conduction through the spinal cord lesion by a control test carried out on the same animal. In this procedure, the medial nerve of the forelimb was stimulated, initiating evoked potentials in a neural circuit unaffected by the crush injury (FIGS. 13A-13C). To perform this test, recording electrodes were left in place while stimulating electrodes were relocated to stimulate the median nerve using identical parameters of stimulation.
Statistics The Mann Whitney, two-tailed test was used to compare the means of the data derived from experimental and sham-treated groups. To compare the proportions between groups, Fishers exact test was used. All tests were performed using INSTAT software.

Results
Physiological Measurements of Conduction Through the Spinal Cord Injury

Figure 13D:
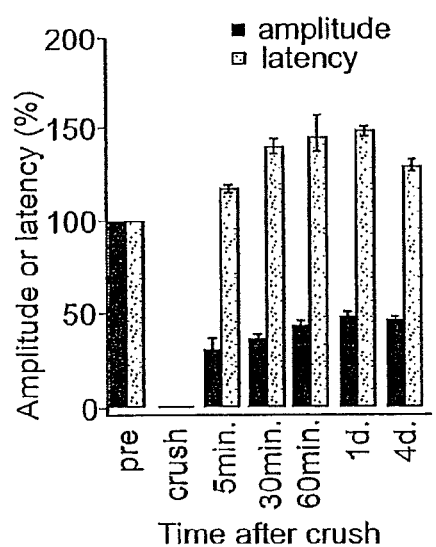
Figure 14A:
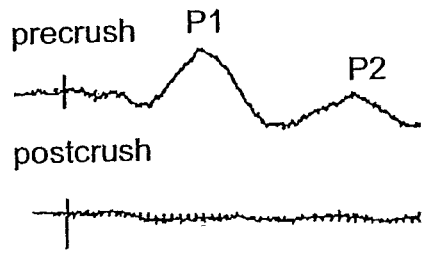
Figure 14B:
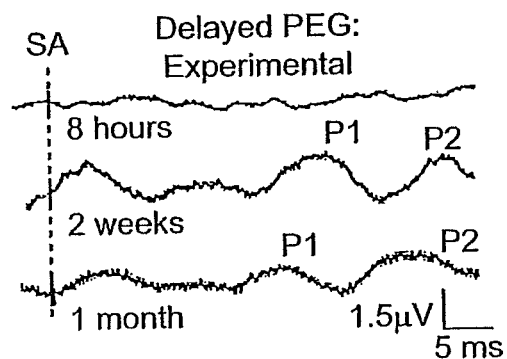
Figure 14C:
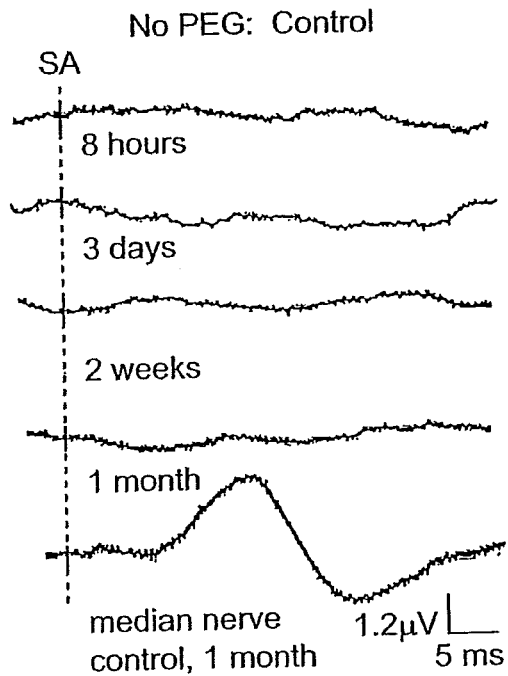
Figure 15:
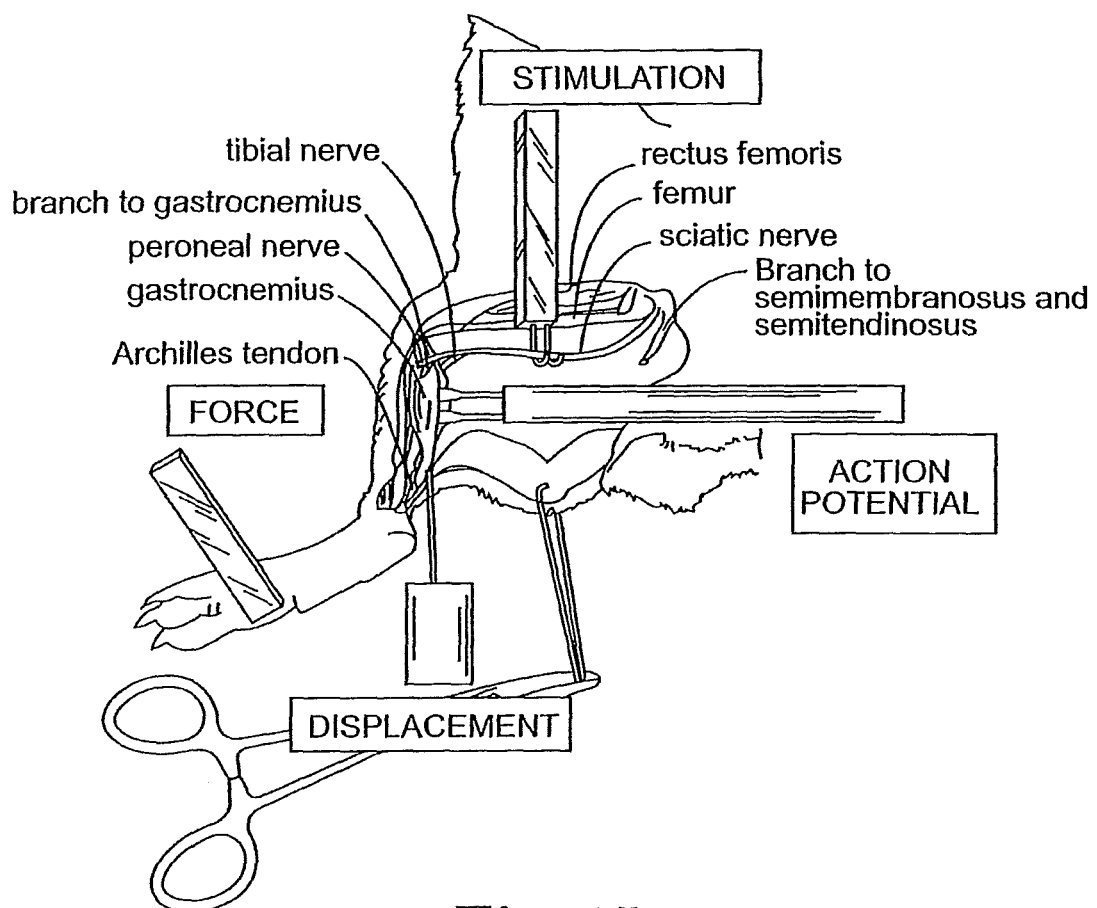

Physiological measurements of SSEP conduction were performed in every animal prior to spinal cord injury and within 5-15 minutes after surgery (FIGS. 13B and 13C; FIGS. 14A-14C) to provide a basis for later comparison. In the uninjured animal, SSEPs were typically observed to segregate into two peaks; early arriving (latency, about 20-30 ms) and a later arriving SSEP (about 35-45 ms; FIGS. 13B and 13C; FIGS. 14A and 14B). In the first experiment depicted in FIG. 13C, subsequent records were taken at approximately 30 minutes, 1 hour, 24 hours, and 4 days after PEG treatment. In the second experiment, subsequent measurements were made approximately 6-8 hours, 18-24 hours (data not shown), 3 days, 2 weeks, and 1 month following the delayed application of PEG. In all animals, the failure to record an SSEP following stimulation of the tibial nerve was further confirmed to be due to a lack of conduction through the injury by a control procedure carried out on the same animal, where the medial nerve of the forelimb was stimulated. In all cases, this produced a characteristic SSEP for this spinal circuit unaffected by the injury (FIGS. 13 A-13C; FIG. 14B). In this investigation, sham-treated animals never regained the ability to conduct SSEPs through the injury site.

In the first experiment depicted in FIGS. 13B and 13C, a detectable SSEP was recorded within a few minutes after PEG application. Quantitative evaluation of 10 of these animal's electrical records showed that SSEP amplitudes continued to improve—averaging about 40% of their preinjury level, and displaying more typical latencies with time (FIGS. 13C and 13D). Remarkably, within minutes of the spinal injury, the total loss of physiological functioning was reversed in 23 of 25 PEG-treated animals. In the two animals that did not immediately respond to PEG application, SSEP recovery was later observed at the 2 weeks time-point (FIG. 14C, Table 3). In the four animals whose recovered SSEPs were tested by reinjury, the second compression of the spinal cord at the original injury site completely eliminated recovered SSEPs, confirming these were conducted through the lesion. In 9 of 11 experimental animals, the delayed application of PEG (about 8 hours post injury) produced a detectable SSEP within 18 hours (FIG. 14C).

All 34 PEG-treated animals recovered SSEP conduction contrasted to the complete failure of all control guinea pigs to conduct evoked potentials through the lesion. Only 3 of 22 sham-treated animals recovered CTM function in both experiments, while 20 of 25 PEG-treated animals recovered variable amounts of CTM functioning which continued to improve with time (Table 2, 3).

Summary of the Results

This report is the first to show that an immediate and brief application of a hydrophilic fusogen, polyethylene glycol, to the site of a severe compression injury to the adult guinea pig spinal cord in vivo results in an immediate recovery of nerve impulse conduction and a progressive recovery of behavioral functioning of the CTM reflex—a quantitative index of white matter integrity [Borgens, R. B., et al. (1990) J. Comp. Neurol. 296:634-653; Blight, A. R., et al. (1990) J. Comp. Neurol. 296:614-633; Borgens, R. B., et al. (1987) Science 238:366-369]. Furthermore, an 8 hour delay in this application still resulted in a similar recovery of these functions. In sharp contrast, sham-treated animals never recovered the ability to conduct nerve impulses, and the minor occurrence of spontaneous recovery of CTM function was rare compared to the PEG-treated group.

This report provides clear evidence of a behavioral recovery dependent on an identified neural circuit within the damaged mammalian central nervous system in response to this experimental treatment [Borgens, R. B. and Shi, R. (1999) J. Faseb (in press)]. This suggests molecular repair and fusion of nerve membranes as a novel treatment of severe trauma to both peripheral nervous system as well as central nervous system tissue.

EXAMPLE 7

Polyethylene Glycol Rapidly Restores Physiological Functions in Damaged Sciatic Nerves of the Guinea Pig This example demonstrates the ability of a PEG application to fuse severed axons of the isolated sciatic nerve permitting an immediate recovery of CAP conduction using recording techniques described above. A brief application of PEG proved able to reconnect the proximal and distal sciatic segments. In an attempt to reverse functional loss subsequent to a severe crush injury of the sciatic nerve in an in vivo sciatic injury model, it was shown that PEG application can produce a statistically significant enhancement of muscle functioning subsequent to mechanical damage to its motor efferent compared to sham-treated animals which displayed a variable level of endogenous repair.

Materials and Methods
Removal of Sciatic Nerve for In Vitro Study

The sciatic nerves of adult female guinea pigs of 350-500 gram body weight were used for these experiments. The animals were deeply anesthetized with 60-mg/kg ketamine hydrochloride and 10-mg/kg xylazine given intramuscularly prior to dissection of the sciatic nerve. Once adequate anesthesia was obtained, the sciatic nerve was dissected from its exit from the sciatic notch of the hind leg to beyond its branching into the tibial and peroneal nerves. Following exposure of the sciatic nerve it was gently blunt probed free from underlying fascia, and an about 38 mm length was removed to an oxygenated vial of Krebs' solution after severing it at the nerve's proximal and distal extremes. All animal use was in compliance with State, Federal, and University guidelines under protocols approved by the Purdue University Animal Care and Use Committee.

In Vitro Sciatic Fusion and Electrophysiological Recordings

The isolated sciatic nerves were placed in a three compartment, double sucrose gap recording chamber. A full description of this chamber, including diagrams and details of its construction and use, has been previously reported [Shi, R., Borgens, R. B., Blight, A. R. (1999): Functional reconnection of severed mammalian spinal cord axons with polyethylene glycol, J. Neurotrauma, 16:727-738; Shi, R., Borgens, R. B. (1999): Acute repair of crushed guinea pig spinal cord by polyethylene glycol, J. Neurophysiology, 81:2406-2414]. Briefly: about a 38 mm long segments of sciatic nerve was placed in the chamber crossing all of its three large interconnected compartments. The ends of the nerve were immersed in isotonic KCL (120 mM), while the central region was immersed in Krebs' solution (NaCl, 124 mM; KCL, 2 mM; $KH_2PO_4$, 124 mM; $MgSO_4$, 1.3 mM; $CaCl_2$, 26 mM; sodium ascorbate, 10 mM; dextrose, 10 mM; $NaHCO_3$, 26 mM; equilibrated with 95% $O_2$-5% $CO_2$). Thus the ends were maintained at approximately intracellular potential while the middle of the sciatic nerve was maintained at approximately extracellular potential. Each of these three large compartments were separated by a small compartment of flowing sucrose (230 mM) helping to maintain electrical isolation of the ends of the nerve and to reduce mixing of the media. CAPs were evoked at one end by bipolar electrodes and recorded at the other end of the strip of spinal cord continuously during each experiment. Recordings were begun after the nerve had equilibrated within the chamber, and during and after a complete transection of the sciatic nerve within the middle compartment.

Typical physiological functioning of the nerve required about ½ to 1 hour of incubation time while immersed in oxygenated Krebs' at 37° C. Once CAP propagation stabilized, the sciatic nerve was completely severed with a laboratory fabricated cutter (a shard of a razor blade attached to an applicator stick), and the two ends of the nerve were observed to be separated by a gap of about 1 mm with a stereomicroscope. Stimulation and recording was continued during transection which completely eliminated the conduction of CAPs from one end to the other. Following transection, the two ends of the cord segments were pushed together, i.e., abutted tightly using a laboratory fabricated device that applied gentle pressure on one segment of the sciatic nerve pressing and holding it against the other [as in Shi, R., Borgens, R. B., Blight, A. R. (1999): Functional reconnection of severed mammalian spinal cord axons with polyethylene glycol, J. Neurotrauma, 16:727-738]. The device was mounted on a micropositioner, and contacted the spinal cord parenchyma with a strip of nylon mesh stretched across two metal bands [Shi, R., Borgens, R. B., Blight, A. R. (1999): Functional reconnection of severed mammalian spinal cord axons with polyethylene glycol, J. Neurotrauma, 16:727-738]. A solution of PEG (1800, 50% by weight in distilled water) was applied by pressure injection through a micropipette to the abutted segments as a continuous stream about 0.5 mm wide and continuing for about 2 minutes. The PEG was applied to one side of the transection, washed across it, and was removed by aspiration on the other side using a second suction pipette. During the PEG application, a continuous stream of oxygenated Krebs' solution was maintained. The electrophysiological properties of the fused sciatic nerve was monitored continuously for approximately 1 hour.

The storage of real time digitized physiological data, management of this data, and the signal averaging of elicited CAP wave forms was accomplished using a custom designed Labview computer program on a Power Macintosh G-3 computer.

In Situ Isolation of Sciatic Nerve

For in situ experiments, the sciatic nerve of the hind leg was surgically exposed past its distal branches as described above. The skin was incised and dissected away from the gastrocnemius muscle. The entire dorso-lateral aspect of the gastrocnemius muscle and its distal insertion (Achilles' tendon) were exposed. All branches of the sciatic nerve except that to the gastrocnemius muscle were incised with iris scissors. Care was taken to irrigate the entire exposed wound frequently during dissection and physiological recording with lactated Ringer's solution to avoid desiccation. Once the sciatic nerve and gastrocnemius muscle were exposed, the animal was secured to a Plexiglas platform with the pelvis and lower limbs elevated approximately 3 cm above the station. The elevation of the limbs enabled free passive and active ankle motion.

Electrophysiological Recording In Situ

Hook shaped AgAgCl stimulation electrodes were fabricated from 26 gauge silver wire and with a micropositioner, gently supported the proximal sciatic nerve just as it exited the sciatic notch. Petroleum jelly was applied to the contact area to cover it and help insulate the point of electrical stimulus from the rest of the body. A paddle shaped transducer (LAB # FT-100. CB Science Inc., Dover, N.H.) was positioned with a micropositioner so that the paddle was firm against the distal metacarpals of the same foot. This transducer was calibrated to measure the force of contraction of the gastrocnemius in dynes. One end of a sliding displacement transducer (LAB #DT-475. CB Science Inc.) was attached to the table and the slide bar sutured to the Achilles' tendon with 3-0 silk sutures. With this arrangement, the displacement of the muscle in mms was measured during contraction. Finally, a pair of AgAgCl disc electrodes were fabricated from 20 gauge wire by heating the end of the bare silver wire to a molten state and pressing the tip to ice. These "disc electrodes" were then chlorodized by conventional techniques. The pair with electrode spacing of about 2-3 mm was placed on the belly of the gastrocnemius muscle to measure compound muscle action potentials (APs in mVs) subsequent to electrical stimulation of the sciatic nerve (FIG. 1).

Following the application of all the electrodes and transducers, the sciatic nerve was stimulated with square wave pulses ($\leq 6$ Hz, 1 ms duration) from the integral stimulator of the LAB™ computer managed integrated system for physiological measurement and recording (PowerLab/4S; ETH-400 bridge amplifier, CB Science Inc. Dell optiplex GX1p computer and CHAR™ software, AD Instruments). The least suprathreshold voltage required producing maximal force and displacement response of the muscle was determined, and 1.25 times that stimulus voltage was used for the remainder of each individual experiment Nerve Injury and PEG Application In Situ Following the exposure of the nerve and muscle and the arrangement of the stimulation and recording electrodes, baseline values of the force, displacement, and muscle action potentials were established. Then, the sciatic nerve was crushed for 90 seconds with modified Dumont 5 forceps. The forceps had been filed so that the tip width was 1.5 mm, and they were bent so that the tips were parallel to each other. Preliminary experiments were used to determine the duration of a standard displacement crush to completely eliminate all three functional measures for a minimum of ½ hour, allowing only minimal recovery of any one functional test within 1-1½ hour post injury (data not shown). Prior to, and immediately following the crush injury, a baseline record of all functional responses to sciatic stimulation was obtained for all animals. Subsequently, 0.05-0.1 cc of a PEG or control solution was injected beneath the epineurium at the region of crush injury with a 29 gauge needle on an insulin syringe. A vital dye was included in each solution to enable direct observation of its removal. Each solution was left in place for 2 minutes. The epineurium was then opened longitudinally with a razor, and the solution was irrigated away with lactated Ringer's. Electrophysiological recording was performed at 5-minute intervals for 90 minutes after administration of each solution. The animals were then euthanized by intracardiac injection of 50 mg pentobarbital.

Those animals treated within 10 minutes of injury were divided into the following groups: (1) the PEG treated group, N=8; (2) a Krebs' solution control group, N=6; and (3) a distilled water control group, N=6. A 50% by weight solution of 1800 MW PEG in distilled water was used in the treated group. Krebs solution consisted of NaCl 124 mM, $KCl_2$ mM, $KH_2PO4$ 1.2 mM, $MgSO_4$ 1.3 mM, $CaCl_2$ 1.2 mM, dextrose 10 mM, $NaHCO_3$ 26 mM, and sodium ascorbate 10 mM. The data obtained from both control groups (described below) were pooled since there was no statistical (or behavioral) difference between them.

Nerve Injury and Delayed PEG Application

Delayed application of PEG or a Krebs' control solution was performed 4 hours after crush injury. Six guinea pigs were treated with PEG (50% solution of 1800 MW PEG), and six animals were treated with the Krebs' control solution. The animals were anesthetized as described previously. Then, a 1 cm segment of the sciatic nerve was exposed at the mid-hamstrings level, and a 90 second crush was performed with the modified Dumont 5 forceps. The wound was irrigated with lactated Ringer's and closed with 3-0 silk sutures. The animals were kept under a warming lamp. Three and a half hours later, the animal was re-anesthetized. The entire sciatic nerve and gastrocnemius muscle were exposed, and the stimulating and recording electrodes and transducers were arranged as described above. Four hours after the crush injury, the solution of either PEG or Krebs' was administered beneath the epineurium at the injury site and was removed after 2 minutes by the techniques described above. Electrophysiological recording was performed at 5-minute intervals for 60 minutes following administration of each solution. The animals were then euthanized by intracardiac injection of 50 mg pentobarbital.

Statistics

Population means were compared with Mann-Whitney two tailed test, while proportions were compared with Fishers exact test, two tailed.

Results

Fusion of Severed Sciatic Nerve In Vitro

Figure 16:
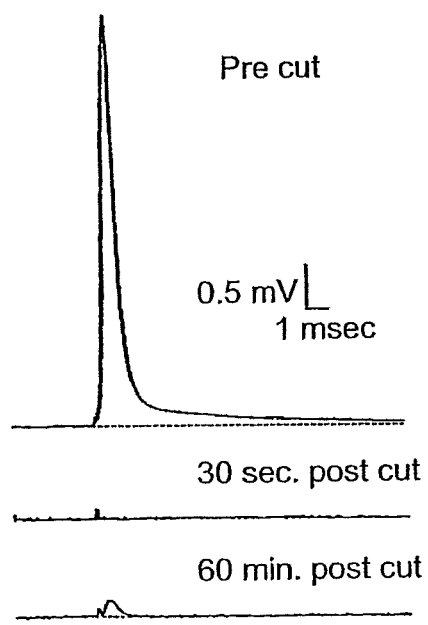

Our investigation began with determining if any axons within the two segments of a severed sciatic nerve were able to be immediately reunited by PEG application. Four sciatic nerve (lengths about 38 mm) were tested in this way in the double sucrose gap chamber. Each was allowed to "recover" from the isolation procedure for varying times up to one hour until the normal capacity to conduct compound action potentials from the point of stimulation to the recording site on the other end of the chambers had stabilized. The average CAP magnitudes prior to the injury were 5, 3.5, 1.5, and 4.8 mV respectively. Stimulation and recording of CAPs was continued during the process of transection, simultaneous with the total elimination of CAP conduction. Within 15 minutes of the mechanical abutting of the proximal and distal segments and 2-minute application of PEG, CAP conduction was variably restored in all four sciatic nerves tested, with an average recovery of 3.45% of the pretransection amplitude. FIG. 16 shows electrical records one such sciatic nerve tested. In summary, all four attempts to fuse completely severed sciatic nerves were successful, restoring a variable level of nerve impulse conduction through the lesion.

Spontaneous and PEG Mediated Recovery of Crushed Sciatic Nerve In Situ

Figure 17A:
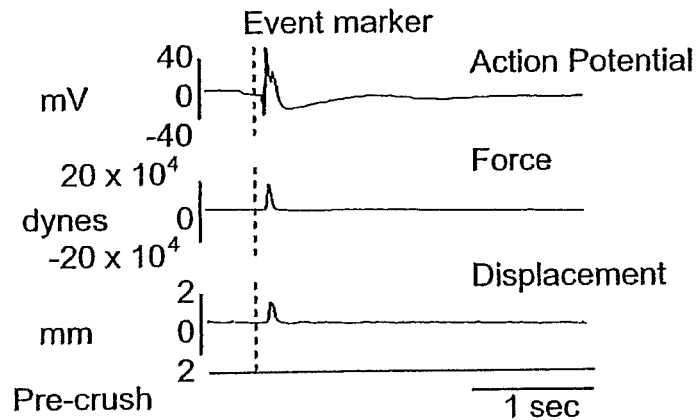
FIGS. 17A-17C are series of graphs showing physiological measurements of gastrocnemius activity in response to stimulation of the sciatic nerve in a sham-treated animal pursuant to the experimental setup of FIG. 15. Electrical recordings of three measures of response to stimulation are shown in each of the three blocks: the event marker is shown as a dashed line. The time base shown in the top block of recordings is the same for all three sets of graphs. The scale units on the x axis are the same for all recordings unless noted. For example, the sensitivity of AP recording is increased by a factor of 2 and 10 in the lower recordings of AP and force, respectively. It is to be noted that the three measurable responses to sciatic stimulation are completely eliminated immediately subsequent to a crush injury of the nerve proximal its insertion on the muscle. It is to be noted as well that this lack of response is stable for the next hour—even at an increased sensitivity of recording.
Figure 17B:
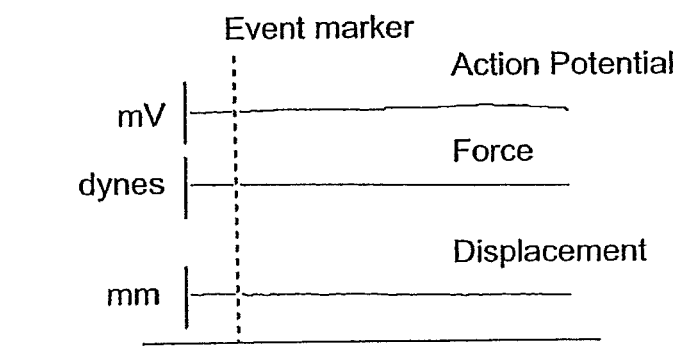
Figure 17C:
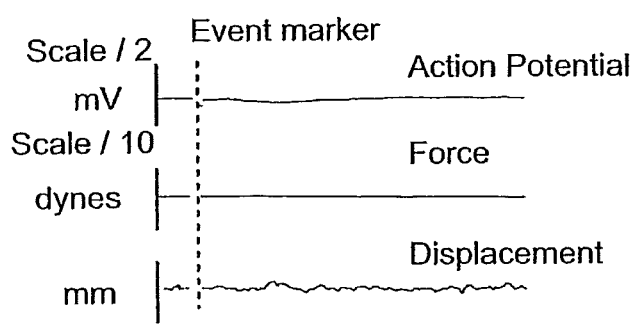

Immediately after the crush procedure, the gastrocnemius muscle did not show any response to stimulation of the sciatic nerve in all animals. FIGS. 17A-17C, 18A, 18B, and 19 show recordings of all three functional tests prior to injury to the nerve, and the complete loss of these as revealed by physiological recordings begun immediately after the injury. FIGS. 17A-17C also shows the lack of response to stimulation 1 hour later in a control animal. This was typical of sham-treated animals. Only three of the 12 animals in this group recovered any one of the functional tests by 1 hour post-treatment.

Figure 18A:
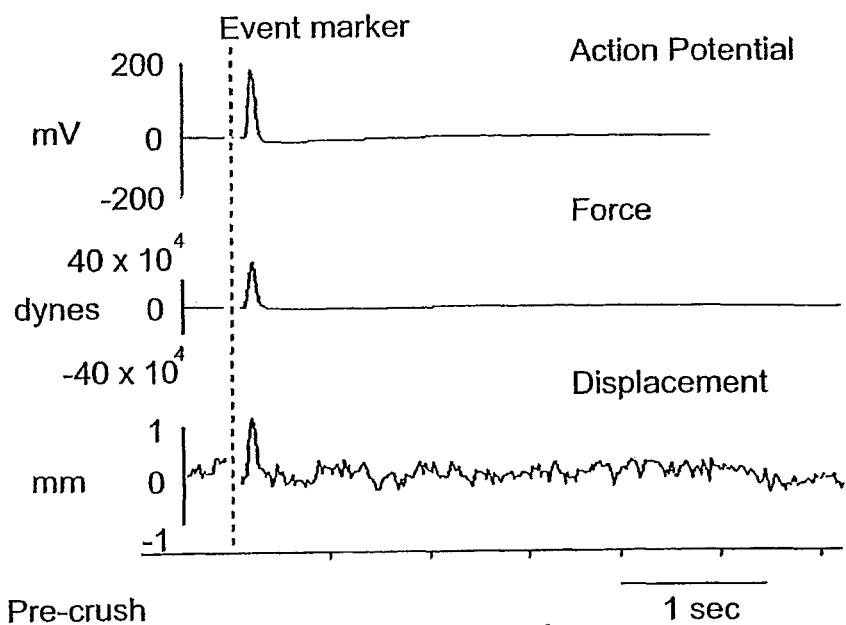
FIGS. 18A and 18B are graphs showing physiological responses of the gastrocnemius muscle to stimulation prior to PEG treatment of a sciatic nerve injury made in the experimental procedure shown in FIG. 15. The conventions are the same as detailed in FIG. 17A-17C. Note the 10 and 100 fold increase in sensitivity of recording in AP and Force immediately following crush injury to the sciatic nerve and the inability to measure any response at this time or sensitivity.
Figure 18B:
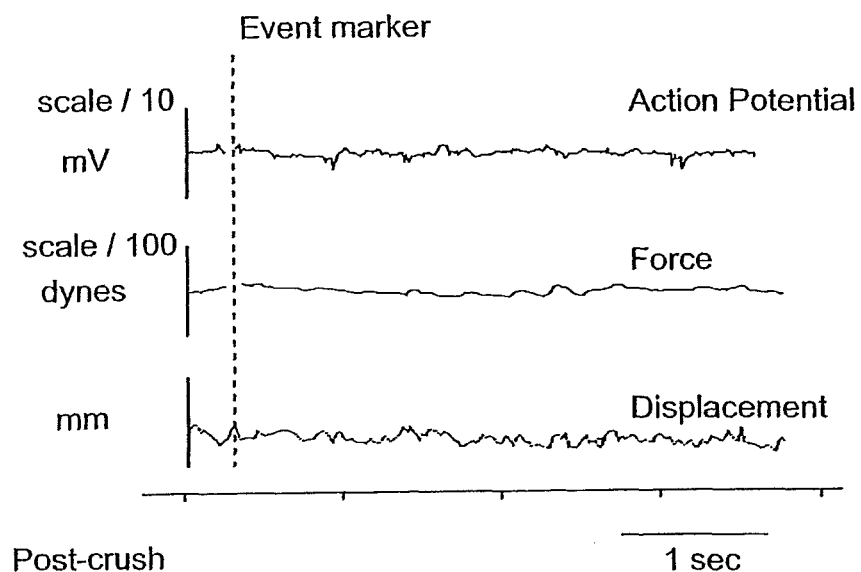
Figure 19:
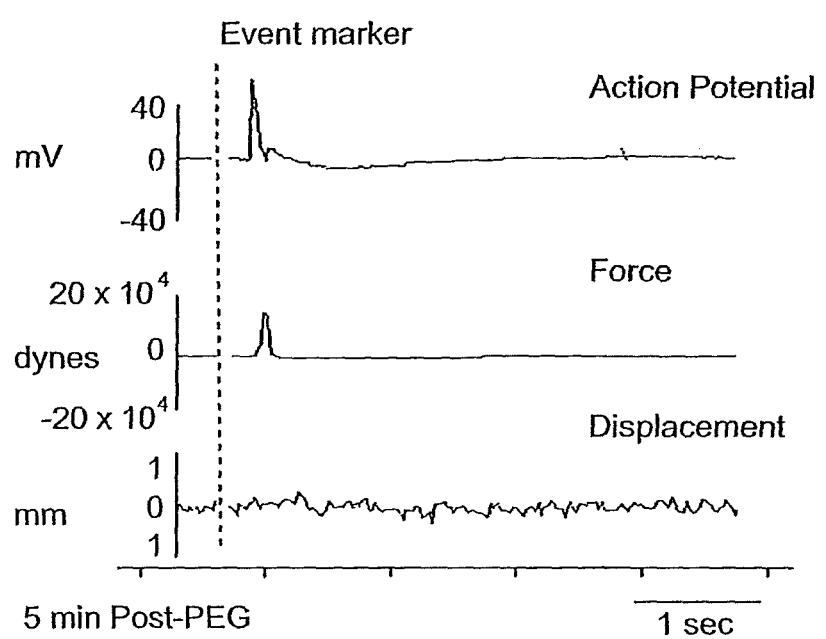
Figure 20A:
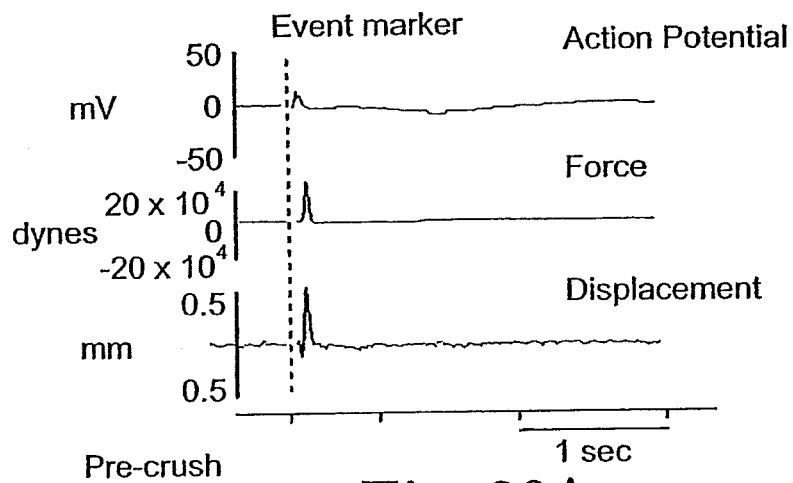
FIGS. 20A-20C are graphs showing long term recovery of functions in a PEG-treated animal. The conventions are the same as in previous figures. These records show the loss and recovery of all three functional measures subsequent to PEG treatment by one hour post injury. Note that a miniscule AP at the limit of detection may have been recorded by an increase in amplification of 10 fold in the post-crush record. This may have signaled a slightly less severe injury than produced in other cases allowing a more complete response to PEG. This was the only case where all three functions had measurably recovered subsequent to nerve injury in any animal.
Figure 20B:
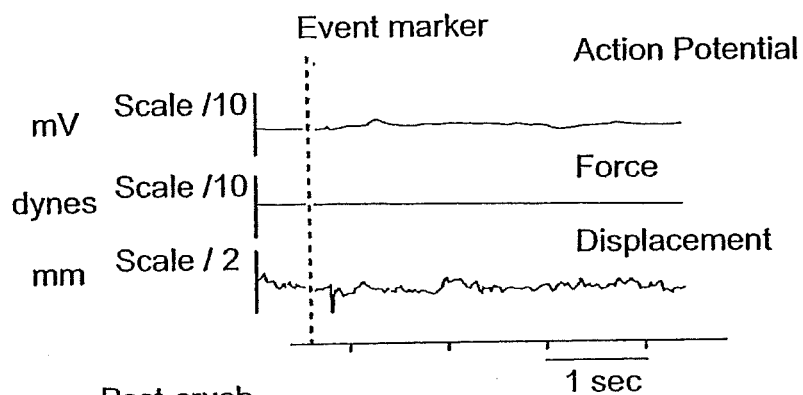
Figure 20C:
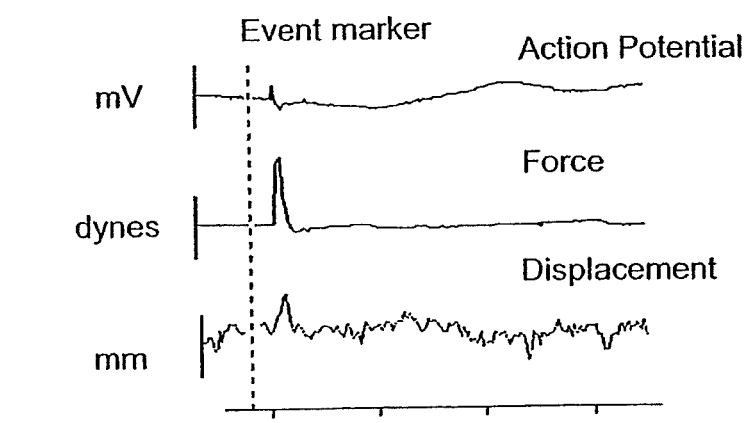

In contrast, 7 of 8 PEG-treated animals recovered at least one of these functions within the first 35 minutes post injury. Four of these animals recovered at least one measure by 5 minutes post treatment, another at 10 minutes, and two more by 30 minutes. This difference in proportion between controls and PEG-treated animals was statistically significant (P=0.019, Fishers exact test). In the PEG-treated group, 1 of the 8 recovered all three functional measures by 1 hour post treatment, 3 of the 8 recovered two of them, and the balance (4 of 8) recovered one measure of functional recovery as mentioned above. FIGS. 18A and 18B show recordings of the three tests prior to injury and their elimination by the crush injury to the sciatic similar to FIGS. 17A-17C but in an animal prior to treatment with PEG. FIG. 19 documents the recovery of two of the three functional measures (muscle action potential and force of muscle contraction) within the first 5 minutes after PEG application in this animal. The response was robust necessitating a reduction in the sensitivity of recording. FIGS. 20A-20C show the only animal (which was PEG-treated) to recover all three indices of functional recovery, though there was some indication that the muscle AP was not completely eliminated following injury when the sensitivity of the recording was increased 10 fold in this one case. Overall the most sensitive and consistent indicator of recovery in all animals was the measurement of muscle contraction force—while the least sensitive was the recording of a measurable displacement of the hind foot. The latter test was dropped from the regimen when delayed PEG applications were evaluated (described below). Table 4 provides a summary of these data.

TABLE 4

Responses to Immediate Application of PEG

| | Animal#[1] | Pre injury[2] | Post injury[3] | 5 min[4] | 15 min[4] | 30 min[4] | 60 min[4] | Statistic[5] |
|---|---|---|---|---|---|---|---|---|
| Control | 12 | 12/12 | 0/12 | 1/12 | — | 1/12 | 1/12 | P = 0.019 |
| PEG-treated | 8 | 8/8 | 0/8 | 4/8 | 1/8 | 2/12[6] | — | |

[1]Animal Number
[2]Number possessing measurable functional responses to sciatic stimulation over total tested (see methods)
[3]Number possessing measurable functional responses to sciatic stimulation subsequent to sciatic injury over total tested
[4]Elapsed time to recovery after application; number over total tested
[5]Statistical comparison of totals; Fisher Exact test, two tailed
[6]One of these preparations recovered at about 35 minutes.

Due to the all or none character of muscle excitability, a comparison of the mean peak AP amplitudes would not have been as informative as would be the proportion of animals recovering excitability following nerve injury and treatment. Comparison of the mean force of muscle contraction however provided a way to compare the relative degree of muscle "recovery" between the groups. The mean contraction force in dynes was significantly improved by the PEG treatment (X=23835±19991; range 0-163000) compared to Controls (X=433+276.3; range=0-2880. P=0.008, Mann-Whitney two tailed test).

No difference (behavioral or statistical) was detected between the groups when a 1 hour delayed application of PEG was tested (data not shown). Comparison between sham-treated and PEG-treated animals following a 4 hour delayed application was informative however—revealing a capability of PEG to still be able to improve functional outcomes. The proportion of Control animals (2 of 6) showing a recovery of at least one functional measure four hours post injury did not change subsequent to the sham application. Following PEG application however, this number quadrupled (1 of 6 animals showed spontaneous recovery by the time of the 4 hour application, which improved to 4 of 6 within 5 to 45 minutes of the treatment). Due to the reduced number of animals this increase in proportion relative to controls did not reach significance, but showed a strong trend in this direction ($P=0.06$, Fishers' exact test).

Discussion

Using both an in vitro and in vivo assessment of physiological functioning in cut and crushed sciatic nerve, it was discovered that a brief (about 2 minute) topical application of PEG is sufficient to restore variable levels of electrophysiological conduction through the lesion. This was demonstrated by PEG mediated reconnection of completely severed sciatic nerves maintained within a double sucrose gap recording chamber, and an in vivo evaluation of muscle excitability following a severe proximal crush injury to its motor efferent. In the latter, two other indices of muscle responsiveness were simultaneously monitored, the force of gastrocnemius contraction and the displacement of the muscle following electrical stimulation of the sciatic nerve. As described, muscle displacement was the most crude, and least sensitive measure of functional recovery. The measure of recovering muscle APs was an intermediate success. Sometimes APs could not be measured traversing the muscle preparation even though simultaneous gastrocnemius contraction was visible and measurable with the force transducer. This was not completely unexpected given the difficulty of measuring extracellular APs in a blood field.

In both testing procedures, PEG application resulted in a rapid recovery of functioning at a time when control preparations had not spontaneously recovered. This was easiest to detect when PEG was applied within minutes of the injury in situ, though a 4-hour delayed application of PEG greatly improved the percentage of cases recovering at least one functional measure. The reduced number of animals studied at these later times did not allow significance to be reached though a strong trend towards significance was noted.

Mechanical Damage to the Axon and its Reversal by PEG

It is now clear that in response to mechanical damage to nerve membranes, the instantaneous and primary insult is a local breakdown of the ability of the membrane to act as an ionic fence. Electrophysiological conduction is impaired or eliminated by the sustained collapse of the membrane potential at the site of damage caused by the unregulated exchange of ions—principally Potassium and Sodium. Anatomical integrity of the axon is compromised by the local increase in Calcium entering cytosol at the foci of damage. This increase in intracellular $Ca^{++}$ from unregulated entry into the cell is also exacerbated by rising levels of intracellular $Na^+$, which initiates release of $Ca^{++}$ from intracellular stores [Carafoli, E., Penniston, J. (1985): The Calcium Signal, Sci. Am., 253:70-78; Rosenberg, L., Lucas, J. (1996): Reduction of NaCl increases survival of mammalian spinal neurons subjected to dendrite transaction injury, Brain Research, 734:349-353; Lucas, J., Emery, D., Rosenberg, L. (1997): Physical injury of neurons: Important roles for sodium and Chloride ions, The Neuroscientist, 3: 89-111]. The net result is the depolymerization of the cytoskeleton, the activation of various $Ca^{++}$ dependent intracellular catabolic enzymes, and other biochemistries leading to local progressive cellular dissolution, axotomy in the most extreme cases, and degeneration of the distal axonal segment in mammals. The duration of this process is of course variable, depending on many characteristics of the nervous tissue damaged and the severity of the impact, compression, or stretch—however it may require many hours to days to run it's course. It is a working hypothesis that this process can be greatly reduced in scope, through the acute use of hydrophilic polymers that can seal even the worst breaches to axonal membrane. This can be demonstrated by the ability of PEG to actually fuse proximal and distal segments of axons restoring anatomical and physiological functioning [these data and Shi, R., Borgens, R. B., Blight, A. R. (1999): Functional reconnection of severed mammalian spinal cord axons with polyethylene glycol, J. Neurotrauma, 16:727-738]. In the less severe injuries to the axolemma, the action of the polymer likely enhances the natural reparative mechanism of sealing by axons. Natural or spontaneously sealing of crush injury to the sciatic nerve, and resultant functional recovery, was demonstrated in this study. This recovery was enhanced by PEG application. In the most severe cases of mechanical damage to axons, PEG-mediated sealing likely prevents axotomy, immediately permitting AP conduction through the injury site, and variable levels of immediate functional recovery dependent on it. Below the experimental evidence supporting these notions is set forth in detail.

The Action of PEG on Damaged Membranes

There are several hypotheses concerning the ability of large hydrophilic polymers like PEG and its cousins, the triblock polymers or non-ionic detergents to reverse cell permeabilization. In certain cases, and at lower molecular weights, PEG may have detergent like properties similar to amphipathic polymers (poloxamers and polaxamines). These may form thin micelle films covering the breach in the membrane. In the triblock polymers, the hydrophobic "head" of the molecules may actually insert itself into the breach in the membrane, since the hydrophobic core of the plasmalemma is exposed by the injury. The hydrophilic PEG "tails" integrate with the outer leaflet. It is also possible that PEG may seal porated membranes through acute dehydration of the local region where it is applied. This is envisioned to enable the structural elements of the membrane (proteins, glycolipids, etc) to resolve into each other as the polar forces arising from the aqueous phase (helping to maintain their organization within the membrane) is now absent or reduced. When PEG is removed and the local membrane(s) are rehydrated, spontaneous reassembly of these structural elements leads to a restoration of the membrane. The latter scenario helps explain the immediate recovery of excitability following topical PEG treatment to nerve membranes, and the success of only brief applications of the polymer to injured tissues. These putative mechanisms of action underlying the polymer mediated fusion and repair of traumatized cell membranes have been previously discussed [Shi, R., Borgens, R. B. (1999): Acute repair of crushed guinea pig spinal cord by polyethylene glycol, J. Neurophysiology, 81:2406-2414; Borgens, R. B., Shi, R. (2000): Immediate recovery from spinal cord injury through molecular repair of nerve membranes with polyethylene glycol, FASEB, 14:27-35; Lentz, B. R. (1994): Induced membrane fusion; potential mechanism and relation to cell fusion events, Chem. and Phys. of Lipids, 73: 91-106; Lee, J., Lentz, B. R. (1997): Evolution of lipid structures during model membrane fusion and the relation of this process to cell membrane fusion, Biochemistry, 36:6251-6259; Merchant, F. A., Holmes, W. H., Capelli-Schellpfeffer, M., Lee, R. C., Toner, M. (1998): Poloxamer 188 enhances functional recovery of lethally heat-shocked fibroblasts, J. Surgical Research, 74:131-140].

In general, use of these families of high molecular weight polymers represent a new concept, as well as a practical means, to deal with acute trauma to tissues caused by the primary breakdown of cell membranes. This includes a reversal of cell permeabilization in various and different injury models including electric shock myonecrosis [Lee, R. C., River, L. P., Pan, F. S., Ji, L., Wollman, R. S. (1992): Surfactant-induced sealing of electropermeabilized skeletal muscle membranes in vitro. P.N.A.S. 89:4524-4528], testicular reperfusion injury [Palmer, J. S., Cromie, W. J., Lee, R. C. (1998): Surfactant administration reduces testicular ischemia-reprefusion injury, Urology, 159:2136-2139], heat shock mediated cell death [Padanlam, J. T., Bischof, Cravalho, E. G., Tompkins, R. G., Yarmush, M. L., Toner, M. (1994): Effectiveness of Poloxamer 188 in arresting calcein leakage from thermally damaged isolated skeletal muscle cells, Ann N.Y. Acad. Sci, 0.92:111-123], and radiological damage to cells [Hannig, J., Yu, J., Beckett, M., Weichselbaum, R., Lee, R. C. (1999): Poloxamine 1107 sealing of radiopermeabilized erythrocyte membranes, Int. J. Radiat. Biol., 75:379-385].

Repair of Nervous System Damage with PEG

The ability of a hydrophilic polymer, PEG, to fuse and seal the axolemma subsequent to mechanical damage was tested. Studies first used ventral spinal cord white matter isolated from adult guinea pigs. Strips of spinal cord were maintained in the double sucrose gap recording chamber and completely transected—then fused with PEG [Shi, R., Borgens, R. B., Blight, A. R. (1999): Functional reconnection of severed mammalian spinal cord axons with polyethylene glycol, J. Neurotrauma, 16:727-738], or crushed within the chamber and repaired with PEG [Shi, R., Borgens, R. B. (1999): Acute repair of crushed guinea pig spinal cord by polyethylene glycol, J. Neurophysiology, 81:2406-2414]. In both of these cases, a topical, 2 minute application of the polymer (about 1400-1800 Daltons) rapidly restored physiological conduction of compound action potentials through the lesion within minutes following injury. Moreover, intracellular labeling with two different fluorescent markers (rhodamine and flourescein labeled dextrans) demonstrated that physiological functioning following transaction of spinal cord and PEG treatment was accompanied by restored anatomical integrity of axons across the transaction plane by the physical reattachment of their proximal and distal segments [Shi, R., Borgens, R. B., Blight, A. R. (1999): Functional reconnection of severed mammalian spinal cord axons with polyethylene glycol, J. Neurotrauma, 16:727-738].

The ability of PEG to repair a severe standardized compression of the spinal cord in vivo has also been tested. The research used extracellular stimulation of the tibial nerve of the hind leg and the recording of volleys of CAPS arriving at the contralateral sensorimotor cortex (so called somatosensory evoked potentials or SSEPs) as an index of electrophysiological recovery, and the recovery of the Cutaneus Trunchi Muscle Reflex (CTM) as a index of behavioral recovery subsequent to severe spinal cord injury. Spontaneous recovery from spinal cord injury through natural mechanisms of repair occurs in less than 20% of the animals followed for a minimum of 1-month post injury. A 2 minute PEG application to the exposed spinal cord injury immediately after the crush (or delayed for 7-8 hours) results in a recovery of the CTM reflex in over 90% of the treated population. A standardized lesioning technique [Moriarty, L. J., Duerstock, B. S., Bajaj, C. L., Lin, K., Borgens, R. B. (1998): Two and three dimensional computer graphic evaluation of the subacute spinal cord injury, J. Neurologic. Sci., 155:121-137] also results in a complete loss in SSEP conduction in the spinal cord in 100% of the injured animals, and there was no recovery of conduction through the lesion observed in any of these Control treatments. A striking and unexpected result was the recovery of SSEP conduction in 100% of PEG treated animals, usually between a few hours to one-day post treatment [Borgens, R. B., Shi, R. (2000): Immediate recovery from spinal cord injury through molecular repair of nerve membranes with polyethylene glycol, FASEB, 14:27-35]. By using a dye exclusion test, it was also learned that this brief PEG application indeed seals spinal cord axons [Shi, R., Borgens, R. (2000): Molecular repair of Nerve membranes in crushed mammalian spinal cord with polyethylene glycol, J. Neurocytology (in press)]. Brief exposure of acutely injured isolated guinea pig white matter to a solution of horseradish peroxidase lead to endocytosis of the label marking only damaged axons. Most axons in the crushed spinal cord took up the label. A striking and statistically significant reduction in HRP uptake was associated with a 2 minute PEG treatment prior to HRP exposure—demonstrating the polymer sealed these breaches [Shi, R., Borgens, R. (2000): Molecular repair of Nerve membranes in crushed mammalian spinal cord with polyethylene glycol, J. Neurocytology (in press)].

Clinical Relevance

This ability of PEG to functionally reconnect severed axons is the most challenging test of its reparative capability. In the sciatic nerve, the organization of the nerve trunk into fascicles and the tough surrounding epineureum raised the possibility that fusion of even some of the axons inside may not be possible—particularly given the possibility of their retrograde degeneration away from the plane of the transection with the facicles. It was discovered that sciatic nerve was similar to spinal cord white matter in that each attempt to fuse some axons within the cut nerve was successful. In spinal cord this has only limited importance to clinical injuries because spinal transection is rare. However this is a meaningful result in the context of neurosurgical reattachment of severely damaged peripheral nerves where the ends of damaged nerve trunks may be resected prior to fascicular alignment and suturing. Additional treatment with PEG requires that procedures to stabilize the perhaps delicate fused regions for an undetermined period of time will be necessary. This additional therapy may pay dividends in permitting a larger level of immediate functional return while eliminating variable degrees of Wallerian degeneration and the atrophy of muscle. A decision was made to begin such exploration with the non-survival procedures reported here—as long term (days to weeks) monitoring of animals with peripheral nerve injuries is complicated. Comparison of any functional testing is made problematic by the robust spontaneous repair and regeneration of rodent peripheral nerves. These data are indicative that a careful evaluation of the long term functional repair of peripheral nerves by PEG, and to define the critical window in time when the application is required, is indeed the next step in these investigations. With respect to spinal cord repair using PEG, these techniques have now been moved into clinical testing using naturally occurring cases of neurologically complete paraplegia in dogs [see Borgens, R. B., Toombs, J. P., Blight, A. R., McGinnis, M. E., Bauer, M. S., Widmer, W. R., Cook, Jr., J. R. (1993): Effects of applied electric fields on clinical cases of complete paraplegia in dogs, J. Restorative Neurology and Neurosci., 5:305-322; Borgens, R. B., Toombs, J. P., Breur, G., Widmer, W. R., Water, D., Harbath, A. M., March, P., Adams, L. G. (1999): An imposed oscillating electrical field improves the recovery of function in neurologically complete paraplegic dogs, J. Neurotrauma, 16:639-657; Blight, A. R., Toombs, J. P., Bauer, M. S. and Widmer, W. R. (1991): The effects of 4-aminopyridine on neurological deficits in chronic cases of traumatic spinal cord injury in dogs: a phase I clinical trial. J. Neurotrauma. 8:103-119].

EXAMPLE 8

Rapid Recovery from Spinal Cord Injury Following Subcutaneously Administered Polyethylene Glycol This example demonstrates that a biomembrane fusion agent, specifically the hydrophilic polymer PEG, can be safely introduced into the bloodstream by several routes of administration, and that the administered PEG specifically targets a hemorrhagic contusion of an adult guinea pig spinal cord. A single subcutaneous injection (30% weight by weight in sterile saline) made 6 hours after spinal injury was sufficient to produce a rapid recovery of CAP propagation through the lesion, accompanied by a significant level of behavioral recovery in only PEG-treated animals.

The results of these tests demonstrate (1) that PEG specifically targets the spinal cord contusion independent of whether it is applied directly to the exposed spinal injury, or by intravenous or subcutaneous injection, and (2) that a single subcutaneous injection of PEG approximately 6 hours after severe SCI is sufficient to induce a rapid reversal of functional losses in nearly all PEG-treated adult guinea pigs compared to the persistence of these deficits in nearly all sham-treated animals. The intravascular delivery of PEG for purposes of treating and repairing injured nerve tissue has also been investigated in a clinical setting using naturally produced cases of paraplegia in dogs, as discussed hereinafter.

Drawing FIG. 13A: Behavioral Model and Physiological Evaluation

This drawing shows the neural circuit of the Cutaneous Trunchi Muscle (CTM) reflex, and its interruption by spinal injury. Nociceptive sensory receptors in the skin project their axons into the spinal cord at each vertebral segment bilaterally via the Dorsal Cutaneus Nerves. These synapse within the spinal cord and project 2nd order ascending sensory nerves in the ventral funiculus of the white matter to the cervical region where these synapse on bilaterally organized constellations of CTM motor neurons. CTM motor neurons project their axons out of the cord on right and left sides via the brachial plexus, where these innervate the cutaneous muscle of the skin via the lateral thoracic branch of the plexus. When the spinal cord is intact, tactile stimulation of the back skin within the CTM receptive field causes a rippling contraction of the skin. Stimulation outside the receptive fields of back skin does not result in skin contractions. A spinal cord injury (drawn on only the left side of the cord for descriptive purposes) interrupts the ascending leg of this circuit producing a region of skin areflexia ipsilateral to the injury and on the same side. Tactile probing within this region does not produce CTM contractions, usually for the life of the animal. Stimulation of back skin above the level of this unilateral lesion, or on the right side produces CTM contractions, as these receptive fields remain unaffected by the unilateral injury to the left side of the spinal cord.

Methods

Animal Surgery and Spinal Cord Injury

Adult Guinea Pigs (<300 gm) were anesthetized with an intramuscular injection of 100 mg/kg ketamine HCL and 20 mg/kg xylazine and the spinal cord exposed by dorsal laminectomy. The midthoracic cord was crushed with special blunted forceps possessing a détente. This standardized, constant displacement injury [Moriarty, L. J., Duerstock, B. S., Bajaj, C. L., Lin, K., and Borgens, R. B. (1998) Two and three dimensional computer graphic evaluation of the subacute spinal cord injury, J. Neurologic. Sci., 155, 121-137] has produced more consistent anatomical injury to the cord and more consistent behavioral loss between animals than constant impact injuries (such as those produced by the various weight drop techniques). Animals were euthanized by deep anesthesia followed by perfusion/fixation. The localization of an FITC decorated PEG (Fl-PEG) in spinal cord was determined by killing the animals for histological processing approximately 24 hours after the application or injection of Fl-PEG. The spinal cords were dissected from the animals, and the segments of spinal cord containing the sites of injury and an intact, more rostral, segment were sectioned with a freezing microtome and evaluated with a fluorescent microscope. Histological cross sections were 5 µm thick, and observed on an Olympus Van Ox Fluorescent microscope using excitation wavelengths of 495 and 545 nm and barrier filters of 475 and 590 nm, respectively. Digital images were captured to the computer with an Optronics DEI 750 camera.

To test the effects of subcutaneous injections of PEG, adult guinea pigs were anesthetized and their mid-thoracic spinal cords were surgically exposed and then crushed by a standardized technique. [Blight, A. R. (1991): Morphometric analysis of a model of spinal cord injury in guinea pigs, with behavioral evidence of delayed secondary pathology, J. Neurolog. Sci., 103: 156-171.] Twenty animals were divided into equal groups of 10. One group received a single subcutaneous injection of PEG (1400 MW) beneath the skin of the neck (0.5 cc; 30% in sterile lactated Ringer's solution; SLR). The sham-treated control group received a single injection of the carrier, lactated Ringer's. Only this one subcutaneous injection per animal was made approximately 6 hours after the spinal cord injury. CTM testing and SSEP recordings were carried out on all 20 animals prior to spinal cord injury, 1 day, 1 week, 2 weeks, and 4 weeks post injury.

Tracing the Distribution of PEG in Injured Spinal Cord

The FITC decorated PEG (about 1400 Daltons; prepared by Molecular Probes, Chatsworth, Calif.) was used to trace the distribution of PEG following different routes of administration. Fl-PEG, 50% weight by weight in SLR was applied directly to exposed spinal cord injury site (with the dura removed) using a Pasteur pipette in two animals. As in prior experiments [Borgens, R. and Shi, R. (2000) Immediate recovery from spinal cord injury through molecular repair of nerve membranes with polyethylene glycol, *FASEB* 14, 27-35], PEG was removed by aspiration and the region irrigated with SLR two minutes later. Subcutaneous injection of 1 cc Fl-PEG (30% w/w in SLR) was made beneath the skin of the neck in two spinal injured guinea pigs using a 22-gauge needle. For IV injection, the jugular vein was surgically exposed, and 1 cc of FL-PEG was injected using a 26-gauge needle. PEG, 30% in lactated Ringer's was also administered by intraperitoneal injection in one case.

In Vivo Conduction Studies

Functional deficits produced by SCI are largely caused by the loss of nerve impulse conduction through mechanically damaged tracts of nerve fibers in spinal cord white matter [Blight, A. R. (1993) Remyelination, Revascularization, and Recovery of Function in Experimental Spinal Cord Injury, Advances in Neurobiology: Neural Injury and Regeneration (Seil, F. J. Ed.), Vol. 59, pp. 91-103, Raven Press, New York]. Accordingly, the loss and recovery of compound action potential (CAP) conduction through the spinal cord injury was evaluated by evoked potential techniques (somatosensory evoked potential testing or SSEP). Stimulation of the Tibial nerve of the hind limb produced ascending volleys of nerve impulses recorded at the contralateral sensory cortex of the brain. These were eliminated between the site of stimulation and recording by the spinal lesion—immediately abolishing the recording of these peaks (postcrush records). Each electrical record was comprised of a stimulus train of 200 stimulations (<2 mA square wave, 200 µs duration at 3 HZ). Three sets of these recordings were made at each measurement period and averaged to produce the single waveform presented in the following data. The appearance of original records prior to computer averaging can be found in prior reports [Borgens, R. and Shi, R. (2000) Immediate recovery from spinal cord injury through molecular repair of nerve membranes with polyethylene glycol, FASEB 14, 27-35]. Conduction of nerve impulses through a median nerve circuit following stimulation of the median nerve of the forelimb (unaffected by the spinal cord injury at the midthoracic level) was a control procedure during SSEP recording. This control stimulation regimen was carried out in every circumstance where a failure to record evoked potentials at the cortex occurred in response to hind limb tibial nerve stimulation—to eliminate the possibility these failures were "false negatives". SSEP recording and averaging was performed with a Nihon Kohden Neuropak 4 stimulator/recorder and a PowerMac G3 computer. Computation of the area beneath the early arriving SSEP peak (P1) was accomplished by scribing a reference line beneath the base of the peak, and determining the unit area contained within it as pixels using IP Lab Spectrum software.

Behavioral Studies

As an index of behavioral recovery, evaluations are made of a spinal cord dependent contraction of back skin in animals—the Cutaneus Trunchi Muscle reflex (CTM)[Blight, A. R., McGinnis, M. E., and Borgens, R. B. (1990): Cutaneus trunci muscle reflex of the guinea pig, J. Comp. Neurol., 296, 614-633; Borgens, R. B. (1992): Applied Voltages in Spinal Cord Reconstruction: History, Strategies, and Behavioral Models, in Spinal Cord Dysfunction, Volume III: Functional Stimulation, (Illis, L. S. ed.), Chapter 5, pp. 110-145, Oxford Medical Publications, Oxford]. The loss of CTM behavior following injury to the spinal cord is observed as a region of back skin, which no longer responds, by muscular contraction to local tactile stimulation [Blight, A. R., McGinnis, M. E., and Borgens, R. B. (1990): Cutaneus trunci muscle reflex of the guinea pig, J. Comp. Neurol., 296, 614-633; Borgens, R. B. (1992): Applied Voltages in Spinal Cord Reconstruction: History, Strategies, and Behavioral Models, in Spinal Cord Dysfunction, Volume III: Functional Stimulation, (Illis, L. S. ed.), Chapter 5, pp. 110-145, Oxford Medical Publications, Oxford; Borgens, R. B., Blight, A. R., and McGinnis, M. E. (1990): Functional recovery after spinal cord hemisection in guinea pigs: The effects of applied electric fields, J. Comp. Neurol., 296, 634-653; Borgens, R. B., Blight A. R., and McGinnis M. E. (1987): Behavioral recovery induced by applied electric fields after spinal cord hemisection in guinea pig, Science, 238, 366-369]. This areflexia does not recover for the life of the animal if the relevant (and identified) ascending CTM tract is severed within the ventral funiculus as the complete neural circuit underlying this behavior has been identified [Blight, A. R., McGinnis, M. E., and Borgens, R. B. (1990): Cutaneus trunci muscle reflex of the guinea pig, J. Comp. Neurol., 296, 614-633]. Following a severe bilateral crush injury of the mid-thoracic spinal cord (such as used here), a bilateral region of areflexia of back skin is produced that still shows very limited ability to spontaneously recover [Borgens, R. and Shi, R. (2000): Immediate recovery from spinal cord injury through molecular repair of nerve membranes with polyethylene glycol, FASEB, 14, 27-35; Borgens, R. B. (1992): Applied Voltages in Spinal Cord Reconstruction: History, Strategies, and Behavioral Models, in Spinal Cord Dysfunction, Volume Functional Stimulation. (Illis, L. S. ed.), Chapter 5, pp. 110-145, Oxford Medical Publications, Oxford]. A variable region of back skin recovery occurs in response to crush injury in a relatively small proportion of spinal injured animals (we estimate <15% rate of overall recovery in untreated animals based on over a decade of experience using this reflex as an index of white matter integrity). Furthermore, there is no compensatory sprouting of cutaneous innervation into non-functioning receptive fields which might mimic a centrally mediated recovery of CTM function as these regions of skin are not denervated [Blight, A. R., McGinnis, M. E., and Borgens, R. B. (1990): Cutaneus trunci muscle reflex of the guinea pig, J. Comp. Neurol., 296, 614-633; Borgens, R. B., Blight, A. R., and McGinnis, M. E. (1990): Functional recovery after spinal cord hemisection in guinea pigs: The effects of applied electric fields, J. Comp. Neurol., 296, 634-653]. Complete details of the anatomically identified circuit, its physiology, behavioral loss and monitoring, and other testing of the CTM as a spinal cord injury model can be found in previous reports [Blight, A. R., McGinnis, M. E., and Borgens, R. B. (1990): Cutaneus trunci muscle reflex of the guinea pig, J. Comp. Neurol., 296, 614-633; Borgens, R. B. (1992): Applied Voltages in Spinal Cord Reconstruction: History, Strategies, and Behavioral Models, in Spinal Cord Dysfunction, Volume IQ: Functional Stimulation, (Illis, L. S. ed.), Chapter 5, pp. 110-145, Oxford Medical Publications, Oxford; Borgens, R. B., Blight, A. R., and McGinnis, M. E. (1990): Functional recovery after spinal cord hemisection in guinea pigs: The effects of applied electric fields, J. Comp. Neurol., 296, 634-653; Borgens, R. B., Blight A. R., and McGinnis M. E. (1987): Behavioral recovery induced by applied electric fields after spinal cord hemisection in guinea pig, Science, 238, 366-369].

Evaluations were not made of walking, inclined plane performance, rope climbing, or other direct or indirect measures dependent on the functioning of hind limbs in spinal injured rodents. These tests are more subjective in interpretation, are not based on identified neural circuits, and cannot sufficiently discriminate movements dependent on intact bilateral hind limb reflexes from those based on restored functioning of damaged white matter tracts.

Statistics

Comparison of the proportions of animals in each group was carried out using Fisher's exact test, two tailed; and a comparison of means with Mann Whitney non parametric two tailed test on Instat software.

Results

FITC-Labeled PEG in Spinal Cord

Figure 21A:
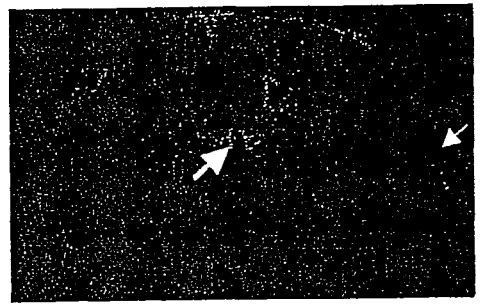
FIGS. 21A-21D are four photographic representations showing polyethylene glycol labeling in crushed guinea pig spinal cord.
Figure 21B:
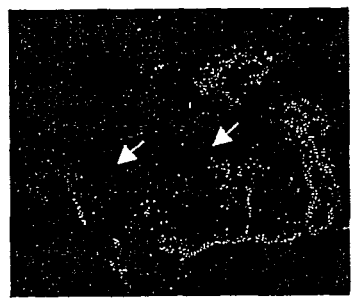
Figure 21C:
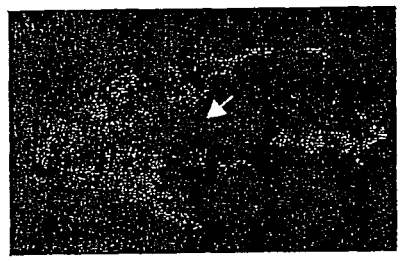
Figure 21D:

Very localized regions of spinal cord tissue surrounding blood vessels and capillaries were faintly marked in uninjured spinal cord rostral or caudal of the injury—nearly at the level of detection (FIG. 21A). This faint labeling was evident around larger vessels of the gray matter and those associated with the pia1 surface. Crushed regions of spinal cord were heavily labeled in all animals independent of the means of Fl-PEG administration. Furthermore, this intense labeling of spinal cord parenchyma was confined to the region of contused gray and white matter but did not extend into adjacent, intact, spinal cord parenchyma (FIG. 21, B-D). In summary, PEG specifically labeled the spinal cord lesion but not undamaged tissues of adjacent regions.

PEG Mediated Recovery of Conduction

Prior to the crush injury of the spinal cord, tibial nerve evoked SSEPs usually segregate into an early and late arriving peaks of CAPs recorded from the sensory cortex (P1 and P2) [Borgens, R. and Shi, R. (2000): Immediate recovery from spinal cord injury through molecular repair of nerve membranes with polyethylene glycol, FASEB, 14, 27-35]. As in prior experiments these peaks are completely eliminated following a severe constant displacement crush to the midthoracic spinal cord (FIG. 4).

Figures 22A, 22B:
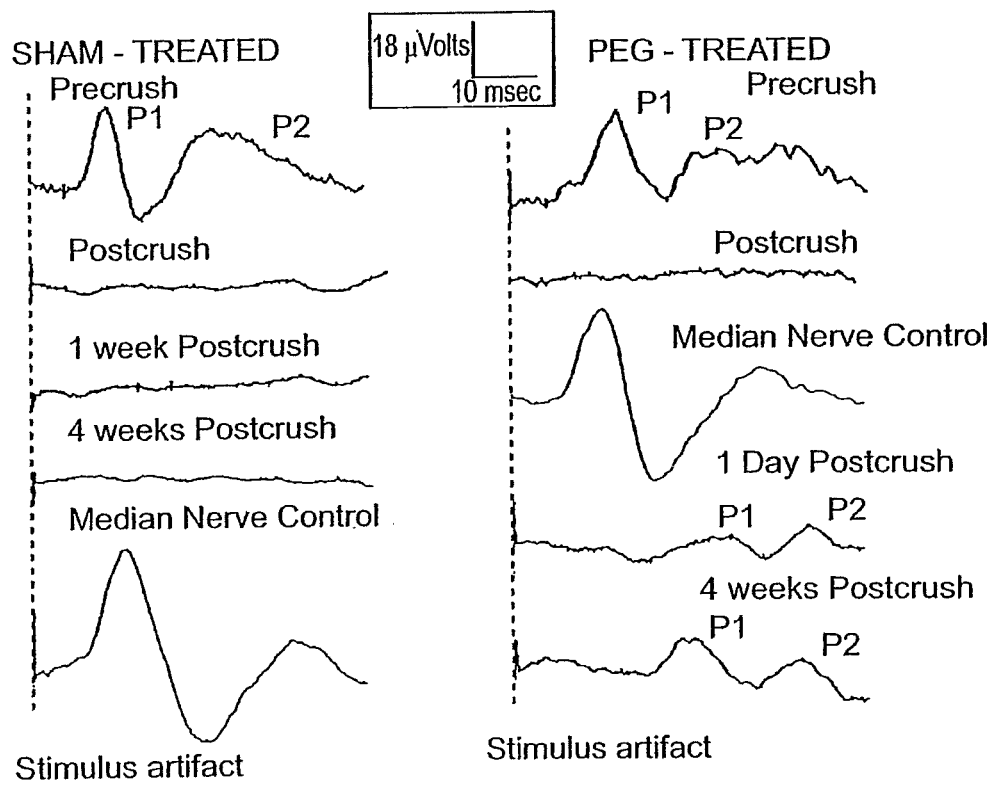
FIGS. 22A and 22B are graphs of electrical records showing loss and recovery of conduction in crushed guinea-pig sciatic nerves after administration of PEG. The first electrical record at the top of both

During the 1 month of observation following a single injection of PEG or an injection of carrier in Control animals, not one control animal recovered the ability to conduct CAPs through the lesion as measured by SSEP recording (FIG. 1) compared to a variable recovery of CAP magnitudes recorded to arrive at the sensorimotor cortex in 100% of the PEG-treated animals (P=0.0001; Fishers Exact two-tailed test; FIG. 22B; Table 5).

TABLE 5

| Treat-Ment | # of Animals | % loss, area of Areflexia[1] | % CTM Recovered[2] | # CTM Recoverd[2] | # SSEP Recovered[3] | Area: CAP(P1) pre-injury in pixels[4] | Area: CAP P1), Post-injury in pixels[4] | Stat[5] |
|---|---|---|---|---|---|---|---|---|
| PEG | 10 | 43.6 □ 0.03 | 32.7□7.5 | 7/10 | 10/10 | 17026 □ 258 | 11482 □ 144 | P = 0.14 |
| Cont | 10 | 42.5 □ 0.02 P = 0.8[6] | | 0/10 P = 0.003[7] | 0/10 P = 0.001[6] | | | |

[1]The % loss of the CTM receptive field = unit area of areflexia in mm$^2$/total intact pre-injury receptive field in mm$^2$
[2]The average percent (and SEM) of the former region of areflexia that recovered following PEG treatment at 1 month.
[3]Number of animals recovered/the total number of animals
[4]The unit area in pixels comprising the early arriving SSEP peak (see methods)
[5]Comparison of pre and post-injury CAP; Mann Whitney, two tailed test
[6]Fisher's exact test, two tailed
[7]Mann Whitney, two tailed test A decrease in the amplitude and extended duration of the CAP is typical of recovering nerve impulses. Thus, it is both useful and possible to compare the change in CAP shape before the injury and after recovery to determine a relative index of the degree of CAP recovery. In this study, the area under the early arriving peak (P 1) was measured in pixels in only PEG-treated animals (since there were no recoveries of SSEPs in Control animals). If 100% of all single nerve fibers contributing to the CAP were once again recruited into conduction subsequent to the injury—but with a decreased amplitude and extended latency period—the normalized mean area under the curve (CAP above baseline) divided by the same pre-injury data should approach unity (1.0). In this experiment, integration of the magnitude (in mVs) and latency (in ms) of PEG-treated animal's SSEP P1 divided by the same pre-injury data equaled 0.88 (Preinjury Mean=1706, SEM=2583 pixels. Post-PEG mean=11482, SEM=1445 pixels, N=10). Paired statistical comparison of these data also confirmed there was not a statistically significant difference in their means, further suggesting limited change in the CAP following PEG mediated recovery (P=0.14, Students T test, paired two tailed comparison). Altogether these calculations suggest a significant recruitment of injured nerve fibers into CAP conduction following PEG treatment that would not have occurred otherwise:

Recovery of the CTM Reflex

The proportion of recovered and unrecovered animals, as well as the unit area of the recovered CTM receptive fields between controls and PEG-injected animals was quantitatively compared. The unit area of back skin that did not respond to CTM stimulation following the injury—but before PEG treatment—was statistically similar in both groups (P=0.81; Mann Whitney, two tailed test; Table 5). Thus, the spinal injury produced a similar level of CTM behavioral loss in all animals. In the 10 PEG-treated animals, 3 recovered CTM function within 24 hours of the injection, 3 more within the first week of the treatment, and 7 by two weeks. The area of recovering backskin of these ten animals continued to increase in size to week four when the experiment was ended. The mean area of recovered CTM receptive fields was approximately 33%. Not one control animal of 10 showed spontaneous recovery of any portion of the CTM receptive field during the 1-month of observation (which was first observed at week 4). The differenced in the frequency of recovery between PEG-injected and sham-injected animals was statistically significant (P≤0.03, Fishers Exact Test, two tailed). Similar results were also achieved in a smaller number of spinal animals in response to a single intraperitoneal injection of PEG (data not shown).

Discussion

PEG is well known to be able to fuse numerous single cells in vitro into one giant cell, as well as join the membranes of neurons and giant invertebrate axons [Bittner, G. D., Ballinger, M. L., and Raymond, M. A. (1986): Reconnection of severed nerve axons with polyethylene glycol, Brain Research, 367, 351-355; Davidson, R. L. and Gerald, P. S. (1976): Improved techniques for the induction of mammalian cell hybridization by polyethylene glycol, Somat. Cell Genet., 2, 165-176; O'Lagae, P. H. and Huntter, S. L. (1980): Physiological and morphological studies of rat phechromocytoma calls (PC12) chemically fused and grown in culture, Proc. Nat. Acad. Sci. USA, 77, 1701-1705]. As a "proof of concept" of the reparative capability of PEG application, variable amounts of completely severed guinea pig white matter axons were physiologically and anatomically reconnected in isolated spinal cord [Shi, R., Borgens, R. B., and Blight, A. R. (1999): Functional reconnection of severed mammalian spinal cord axons with polyethylene glycol, J. Neurotrauma, 16, 727-738]. This result is less relevant to clinical spinal cord injury since transections are rare—but set the stage for further testing of the usefulness of the polymer in severely crushed CNS and PNS nerve fiber tracts. In previous reports it has been shown that the reversal of conduction loss in injured spinal cord was associated with a PEG-mediated sealing of breaches in the nerve membrane produced by mechanical damage [Shi, R and Borgens, R. B. (2001): Anatomical repair of nerve membranes in crushed mammalian spinal cord with polyethylene glycol, J Neurocytol, in press]. Breaches in nerve membrane allow the unregulated exchange of ions between the extracellular and intracellular compartments. This causes an immediate local collapse in membrane potential and the failure of nerve impulse conduction through this region of the axon. This initial conduction block accounts for the immediate functional loss following SCI, which becomes permanent due to progressive anatomical degeneration of injured nerve fibers and spinal parenchyma—so called "secondary injury" [Young, W. (1993): Secondary injury mechanisms in acute spinal cord injury, J. Emerg. Med., 11, 13-22; Tator, C. H. and Fehlings, M. G. (1991): Review of the secondary injury theory of acute spinal cord trauma with emphasis on vascular mechanisms, J. Neurosurg 75, 15-26]. The remarkable increases in cytosolic $Na^+$ and $Ca^{++}$ moving down their concentration gradients into the cell (or local region of its process) through compromised membrane is implicated in the destruction of the cell's cytoskeleton and triggers a cascade of degenerative changes that unchecked, leads to axotomy, sometimes cell death [Borgens, R. B. (1988): Voltage gradients and ionic currents in injured and regenerating axons, Advances in Neurology, Vol. 47: Functional Recovery in Neurological Diseases, (Waxman, S. G., ed.), pp. 51-66 Raven Press, New York; Maxwell, W. L. and Graham, D. I. (1997): Loss of axonal microtubules and neurofilaments after stretch-injury to guinea pig optic nerve fibers, I Neurotrauma, 14, 603-614]. There is clear evidence that PEG treatment intervenes in this process by sealing the membrane, quickly restoring its ability to propagate nerve impulses and inhibiting the progressive dissolution of cells of the spinal cord predicated on the breakdown of the membrane's barrier properties. This result was shown using a dye exclusion test where PEG treatment largely inhibited the uptake of a horseradish peroxidase (HRP; about 40,000 Daltons) marker into damaged axons of crushed guinea pig spinal cord. This effect was also independent of axon caliber [Shi, R. and Borgens, R. B. (2001): Anatomical repair of nerve membranes in crushed mammalian spinal cord with polyethylene glycol, J Neurocytol in press]. This seal produced by PEG is not perfect however, in spite of the recovery of membrane excitability. Reports have been made that local application of the fast potassium channel blocker 4-Aminopyridine nearly doubles the magnitude of the recovered CAP in vitro testing [Shi, R. and Borgens, R. (1999): Acute repair of crushed guinea pig spinal cord by polyethylene glycol, J. Neurophysiology, 81, 2406-2414] suggesting that the PEG-sealed region of membrane is still leaky to potassium.

Membrane breaches secondary to mechanical damage large enough to permit the uptake of large molecular weight intracellular labels such as horseradish peroxidase (HRP)—a common means to introduce such markers into neurons [Borgens, R. B., Blight, A. R. and Murphy, D. J. (1986): Axonal regeneration in spinal cord injury: A Perspective and new technique, J. Comp. Neurol., 250, 157-167; Malgrem, L. and Olsson, (1977): A sensitive histochemical method for light and electron microscope demonstration of horseradish peroxidase, Y. J. Histochem. Cytochem., 25, 1280-1283]—likely progress on to such a size as to lead to secondary axotomy. The destruction of the white matter has been implicated as producing a robust signal for the inflammatory processes which further destroy the cells and tissues of the spinal cord—essentially collateral damage to healthy cells. The histology of PEG-treated spinal cord lesions has been compared to controls by computer managed quantitative 3 D spinal cord reconstruction techniques [Duerstock, B. S., Bajaj, C. L., Pascucci, V., Schikore, D., Lin, K-N., and Borgens, R. B. (2000): Advances in three-dimensional reconstructions of the experimental spinal cord injury, Computer Medical Imaging and Graphics, 24 (6), 389-406]. In these studies a topical application of PEG produced 1-month-old spinal cord lesions of smaller volume, and possessing less cavitation than measured in control animals (to be reported elsewhere). These data strongly suggests that polymeric sealing of nerve cell membranes is also reflected in an overall reduction in spinal cord pathology which can be observed many weeks later.

Evaluation of the ability of this agent and other water-soluble membrane sealing polymers such as the poloxamers and poloxamines continues [Padanlam, J. T., Bischof, J. C., Cravalho, E. G., Tompkins, R. G., Yarmush, M. L. and Toner, M. (1994): Effectiveness of Poloxamer 188 in arresting calcein leakage from thermally damaged isolated skeletal muscle cells. Ann N.Y. Acad. Sci. 92, 111-123; Palmer, J. S., Cromie, W. J. and Lee, R. C. (1998): Surfactant administration reduces testicular ischemia-reprefusion injury, J. Urology, 159, 2136-2139; Lee, R., River, L. P., Pan, F. S., Wollmann, L. Jr. and R. L. (1992): Surfactant-induced sealing of electropermeabilized skeletal muscle membranes in vivo, Proc. Natl. Acad. Sci. U.S.A., 89, 4524-4528] as novel treatments for severe CNS and PNS injury, as well as head injury and stroke.

Since the PEG injection can be made many hours after injury, clinical testing of an intravenous (IV) PEG administration to severe, acute, natural cases of paraplegia in dogs has begun [Borgens, R. B., Toombs, J. P., Blight A. R., McGinnis M. E., Bauer, M. S., Widmer, W. R. and Cook Jr., W. R. (1993): Effects of applied electric fields on clinical cases of complete paraplegia in dogs, J. Restorative Neurology and Neurosci., 5, 305-322; Borgens, R. B., Toombs, J. P., Breur, G., Widmer, W. R., Water, D., Harbath, A. M., March, P. and Adams, L. G. (1999): An imposed oscillating electrical field improves the recovery of function in neurologically complete paraplegic dogs, J. of Neurotrama, 16, 639-657]. This means of clinical development is unique to this spinal research center and has been previously used to develop two other laboratory animal derived treatments for spinal injury [Borgens, R. B., Toombs, J. P., Breur, G., Widmer, W. R., Water, D., Harbath, A. M., March, P. and Adams, L. G. (1999): An imposed oscillating electrical field improves the recovery of function in neurologically complete paraplegic dogs, J. of Neurotrama, 16, 639-657; Blight, A. R., Toombs, J. P., Bauer, M. S. and Widmer, W. R. (1991): The effects of 4-aminopyridine on neurological deficits in chronic cases of traumatic spinal cord injury in dogs: a phase I clinical trial, J. Neurotrauma, 8, 103-119] into human clinical testing. In this new trial, PEG administration is an adjunct to the routine management of neurologically complete spinal injured dogs since the polymer can be safely introduced in the IV fluids administered soon after their admission to the hospital. Though this clinical trial is not yet completed, preliminary observations are encouraging, and appear to show unexpected recoveries of varied functions within hours to a few days after PEG injections.

EXAMPLE 9

Behavioral Recovery from Spinal Cord Injury Following Delayed Application of Polyethylene Glycol In this example, the behavioral character of the recovered CTM reflex produced by a delayed application of PEG is evaluated, and confirms observations of the physiological recovery of conduction in 100% of these spinal injured animals.

Methods and Materials

Surgery and Anesthesia

A total of 29 adult (300 gm) guinea pigs were used in this experiment. They were divided into two groups, PEG treated=15, Sham treated=14. One animal died following surgery in the control group. Guinea pigs were anesthetized with an intramuscular injection of 100 mg/kg ketamine HCL, and 20 mg/kg xylazine, prior to surgical exposure of the cord by dorsal laminectomy and removal of the Dura (Borgens et al., 1986, 1990). A standardized injury was produced using a constant displacement 15 second compression of the cord using a specially constructed forceps possessing a détente (Blight, 1991, see also Moriarty et al., 1998). This lesioning procedure had been calibrated to produce total loss of compound action potential (CAP) conduction through the spinal cord injury and behavioral functioning of the CTM reflex (Borgens and Shi, 2000). To sedate animals for behavioral and physiological testing, guinea pigs were injected with 0.1 cc $Na^+$ Pentobarbital, 50 mg/ml. All surgical procedures and testing were carried out under protocols approved by the Purdue University Animal Care and Use Committee, in accordance with Federal, State, and University guidelines governing animal use in research.

PEG Application

An aqueous solution of PEG (1800 daltons, 50% by weight in distilled water) was applied with a pateur pipette to the exposed injury for two minutes and removed by aspiration. The region was immediately washed with isotonic Krebs' solution (NaCl 124 mM, KCL 2 mM, $KH2PO_4$ 1.24 mM, $MgSO_4$ 1.3 mM, $CaCL_2$ 1.2 mM, dextrose 10 mM, $NaHCO_3$ 26 mM, sodium ascorbate 10 mM) which was also aspirated to remove excess PEG. In sham-treated animals, the injury site was re-exposed surgically at about 7 hours, a control application of water applied, for 2 minutes, followed by a lavage with Krebs' solution, which was removed by aspiration. The wounds were closed, and animals kept warm with heat lamps until awaking. Guinea pigs were housed individually and fed ad libidum.

Behavioral Analysis

The CTM behavior is observed as a rippling of the animal's backskin following light tactile stimulation. These contractions can be measured by tattooing a matrix of dots on the animal's shaved back. When the skin contracts towards the point of tactile stimulation—the dots move in this direction. The skin movement is dependent on sensory afferents projecting as a long tract of axons in each ventral funiculus of the spinal cord (just lateral to the spinothalamic tract) to a nuclei of CTM motor neurons located at the cervical/thoracic junction [Blight, A. R., Mcginnis, M. E., and Borgens, R. B. (1990): Cutaneus trunci muscle reflex of the guinea pig, J. Comp. Neurol., 296, 614-633; Thierault, E. and Diamond, J. (1998): Noceptive cutaneous stimuli evoke localized contractions in a skeletal muscle, J. Neurophys., 60 446-447] (see FIG. 12A). The reflex is bilaterally organized into segmentally arranged receptive fields, displays little supraspinal control, and is lost following spinal injury producing a region of areflexia below the level of the lesion [Borgens, R. B., Blight, A. R., and McGinnis, M. E. (1990): Functional recovery after spinal cord hemisection in guinea pigs: The effects of applied electric fields, J. Comp. Neurol., 296: 634-653; Blight, A. R., Mcginnis, M. E., and Borgens, R. B. (1990): Cutaneus trunci muscle reflex of the guinea pig, J. Comp. Neurol., 296, 614-633; Thierault, E. and Diamond, J. (1998): Noceptive cutaneous stimuli evoke localized contractions in a skeletal muscle, J. Neurophys., 60 446-447] (FIG. 12A). Recovery of the CTM reflex within this region of areflexia is usually not observed for the life of the animal following transection, and infrequently (<20%) following severe crush lesions to guinea pig spinal cord [Blight, A. R., Mcginnis, M. E., and Borgens, R. B. (1990): Cutaneus trunci muscle reflex of the guinea pig, J. Comp. Neurol., 296, 614-633; Borgens, R. B. and Shi, R. (2000): Immediate recovery from spinal cord injury through molecular repair of nerve membranes with polyethylene glycol, FASEB, 14:27-35].

To visualize and quantify the CTM behavior, we evaluated four individual components of it by stopframe analysis of videotaped records of the periods of behavioral testing. 1.) the unit area of recovery of receptive fields below the level of the lesion, 2) the direction of skin movement in normally functioning and recovered receptive fields following injury, 3.) the distance of skin movement during peak contraction, and 4) the velocity of skin contraction following tactile stimulation.

Figure 24A:
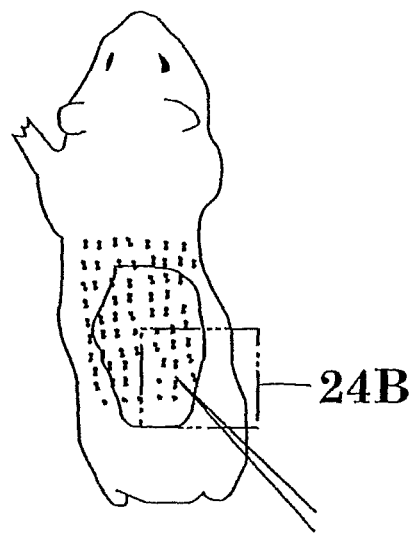
FIGS. 24A-24C are two tracings, on different scales, of captured and superimposed video images of a guinea pig during a period of CTM stimulation with a monofilament probe, showing a dot matrix evaluation of the CTM reflex.
Figure 24C:
Figure 24B:
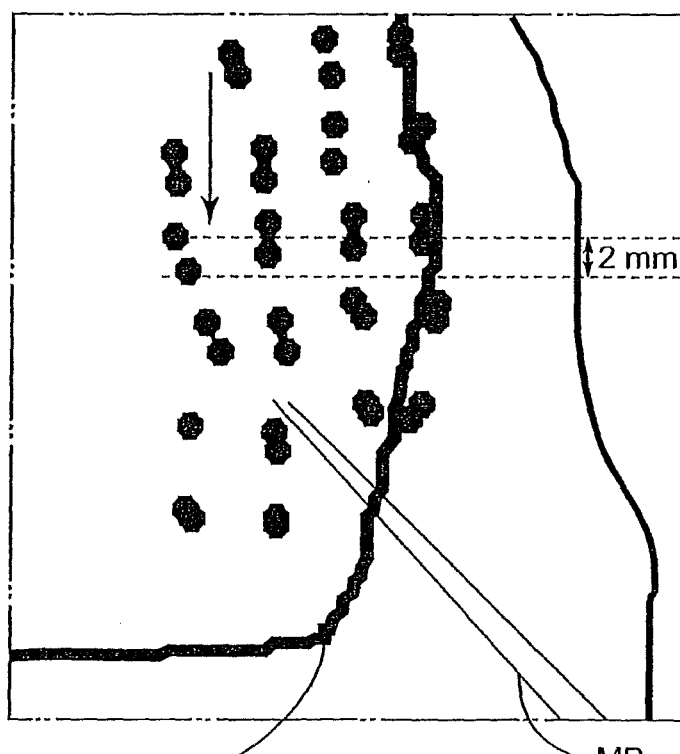

The overall pattern of skin movement can be quite complex in response to a very focal stimulus. Thus we chose to restrict our quantitative evaluation of backskin movement to the peak contractions in response to stimulation at any time point. When the region of peak skin contraction was determined as the region of skin where dots were displaced the greatest distance, the video tape was reversed to a time just prior to stimulation and skin movement. Then the video tape was advanced at intervals of $\frac{1}{24}^{th}$ of a second so that a timepoint prior to—and just at the peak of skin contraction—could be captured to the computer. These frames were superimposed over images of the animals, and the distance of peak contraction divided by the time required to produce it. This provided a measure of the velocity of skin contraction (FIGS. 24A-24C). The character of skin movement following tactile stimulation was determined at the preinjury evaluation for all but four animals, and for all animals at 1 day, 3 days, 2 weeks, and 1 month post treatment. When the peak contraction was determined for any one animal, a protractor was used to measure the angle in which skin pulled towards the monofilament probe used to stimulate the backskin relative to an imaginary line perpendicular to the animals long axis at the midline. The peak contraction of skin was recorded as a positive angle when pulling towards the probe, and a negative angle in the infrequent case where skin pulled away from the probe. The peak contraction was also recorded to be due to stimulation ipsilateral or contralateral of midline relative to the place of tactile stimulation.

Physiological Recording of SSEPs

Figure 25A:
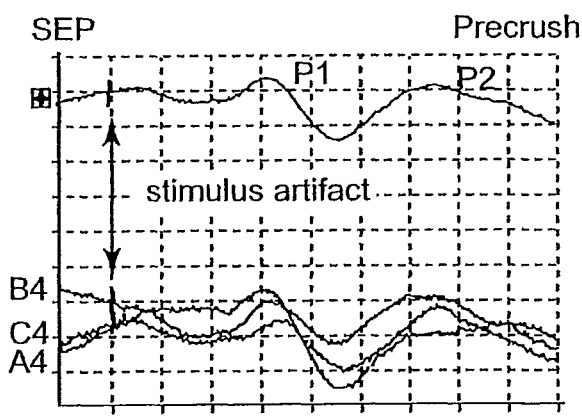
FIGS. 25A and 25B are graphs of measured somatossensory potentials SSEP. In a preinjury record (FIG. 25A), the bottom three overlapping traces were produced by three separate sets of standard stimulations (see methods of Example 9 below). These signals were averaged to produce the single top trace revealing two peaks of early and late arriving evoked potentials (P1 and P2) at the brain (see methods of Example 9). The peaks shown are characteristic SSEPs subsequent to tibial nerve stimulation in adult guinea pigs. The double headed arrow shows the stimulus artifacts. A similar recording is shown in FIG. 25B; however, this record was taken within 30 minutes of a standardized compression to the mid thoracic spinal cord. Note the complete loss of all ascending SSEPs.
Figure 25B:
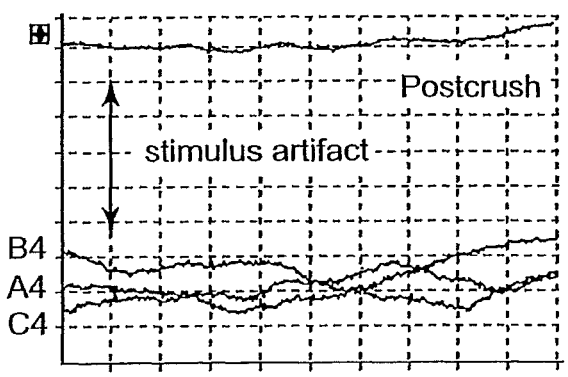
Figure 25C:
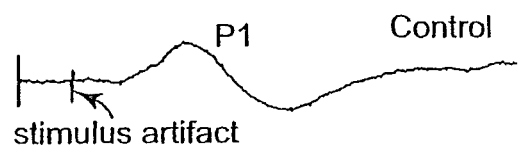
In FIG. 25C, a single averaged trace is shown of a median nerve stimulation control procedure recorded in this same animal within minutes of the traces shown in FIG. 25B.

Subdermal electrodes stimulated nerve impulses from the tibial nerve of the hind leg (stimuli trains in sets of 200 at 3 Hz; stimulus amplitude ≤3 mA square wave, 200 µs in duration; FIGS. 25A-25C). Evoked Potentials, more properly Somatosensory Evoked Potentials (SSEPs), were conducted through the spinal cord to the sensory cortex of the brain. Recording of SSEPs employed a pair of subdermal electrodes located above the level of the contralateral cortex with a reference electrode usually located in the ipsilateral pinna of the ear. The stimulation and computer management of evoked potential recordings utilized a Nihon Kohden Neuropak 4 stimulator/recorder and PowerMac G3 computer. In all animals, the failure to record an SSFP was further confirmed to be due to a lack of evoked potential conduction through the lesion by a control test carried out at this time. The medial nerve of the forelimb was stimulated, initiating evoked potentials in a neural circuit above the level of the crush injury. To perform this test, recording electrodes were left in place while stimulating electrodes were relocated to stimulate the median nerve of the foreleg.

Computer Management of Behavioral Data

Video images were acquired to an Intel® Dual Pentium® Pro computer. Superimposing of images, the coloring of receptive field boundaries made on the backskin of the animals during CTM testing, and the general management of video images was performed using Adobe® Photoshop® software. Final Plates were constructed with Microsoft® PowerPoint software and printed on an Epson Stylus Color 800 printer. Quantitative planimetry of the unit area of receptive fields—or regions of behavioral loss and recovery from these video images—was carried out using IP Lab Spectrum™ software.

Statistics

The Mann Whitney, two tailed test was used to compare the means of the data derived from experimental and sham-treated groups. To compare the proportions between groups, Fishers exact test was used. All tests were performed using INSTAT software.

Results

Only 1 animal died (subsequent to surgery) during the coarse of this study. The loss of the receptive fields subsequent to lesioning of the spinal cord resulted in a region of areflexia that was similar in all animals (mean loss of the total receptive field in sham treated animals=59.2%±5.0; in PEG treated animals=52.2%±2.4. P=0.19; Mann Whitney two tailed test).

A second surgery permitted the application of PEG about 7 hours post injury. A sham treatment (2 minute lavage of the lesion with water followed by aspiration, and a Kreb's lavage) was made to control animals at this same time. Animals were tested for behavioral and physiological recovery about 24 hours, 3 days, 2 weeks, and 1 month post treatment. In every case where an SSEP was not recorded following stimulation of the tibial nerve of the hind leg, the median nerve control procedure was used to test if this was due to any problem that would result in a "false negative" electrical recording. The control procedure confirmed the failure of evoked potentials to propagate through the lesion in every test.

As will be discussed below, since not one control animal recovered an SSEP, 13 of the 15 experimental animals with the best electrical records were quantitatively evaluated. Similarly, a full evaluation of CTM functioning by stop-frame videographic analysis was carried out on the three controls that recovered the reflex, and on 13 of the 15 recovered PEG-treated animals for comparison.

The Cutaneus Trunchi Muscle Reflex

Figure 26A:
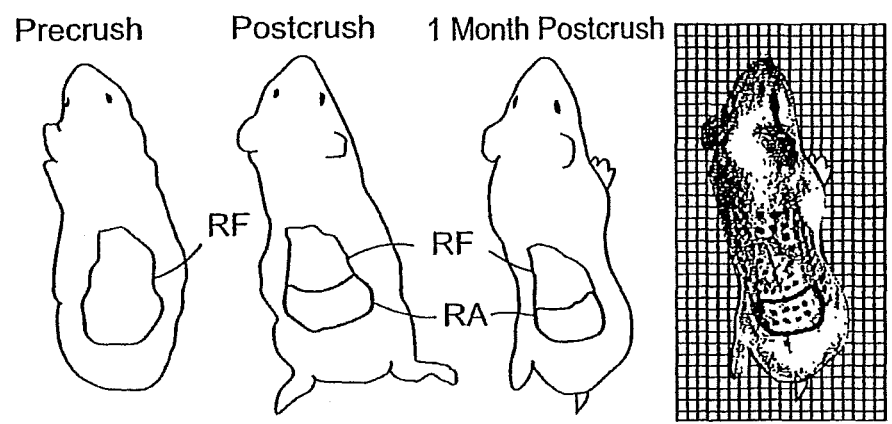
FIGS. 26A and 26B show loss and recovery of CTM receptive fields in the tests of Example 9.
Figure 26B:
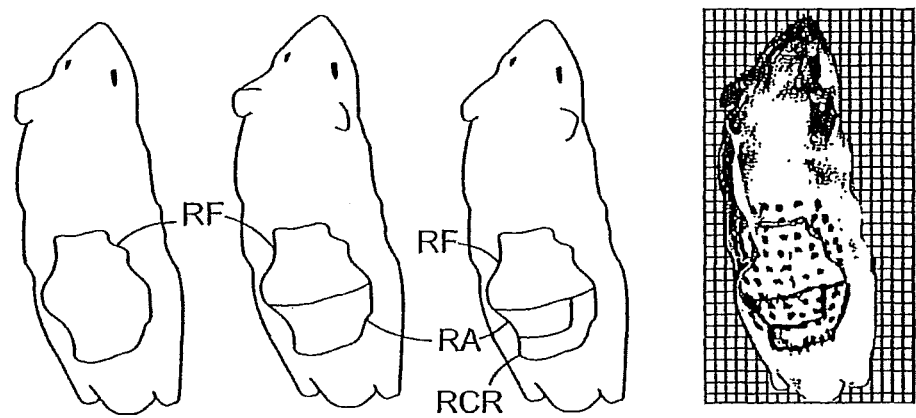
Figure 27A:
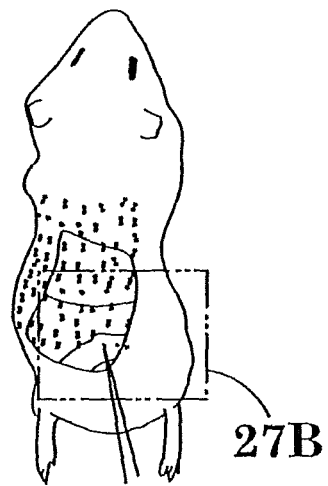
FIGS. 27A and 27B depict a dot matrix evaluation of a recovered CTM reflex in a PEG-treated animal per Example 9 discussed below.
Figure 27C:
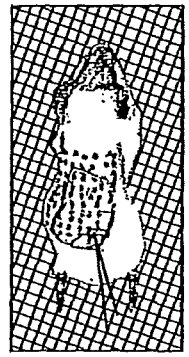
FIG. 27C shows the actual video images collapsed in layers to produce FIGS. 27A and 27B.
Figure 27B:
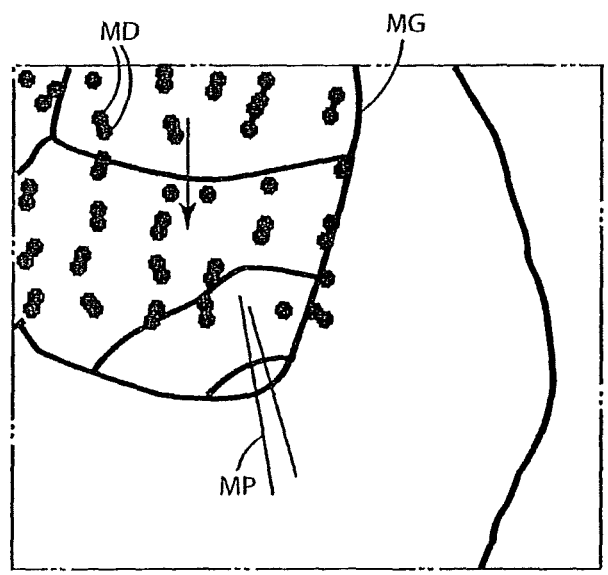

Application of PEG produced a very rapid recovery of CTM function in 73% of treated animals within the first 24 hours compared to a complete lack of spontaneous recovery in sham-treated animals at this time (FIGS. 26A and 26B). Some spontaneous recovery of the CTM reflex in controls began to appear on day 3 resulting in 3 recoveries out of a total of 13 animals (23%) by one month (Table 6). In marked contrast, 11 of 15 PEG-treated animals recovered the reflex activity within the region of areflexia during the first day post treatment (Table 6, FIGS. 26A and 26B), and another three animals by 1 month (total recovery=93%; P≤0.0003; Fisher's exact test, two tailed; FIGS. 26A, 26B, 27A, 27B). The unit area of recovered areflexic backskin was 27.6%±8.6 in the 15 PEG-treated animals, and 18.3%±3.4 for the three controls. Thus, the total area of PEG mediated recovery was not statistically different than that which occurs spontaneously—but infrequently (P=0.28; Mann Whitney, two tailed test).

TABLE 6

Functional and physiological recovery in experimental (Exp) and control (Ctl) animals.

| | | Cutaneous Trunci Muscle Recovery | | | | | | SSEP Recovery | | | | |
|---|---|---|---|---|---|---|---|---|---|---|---|---|
| | N[1] | Post[2] | Day 1[3] | Day 3 | Wk 2 | Wk 4 | Stat[4] | Post[2] | Day 1 | Day 3 | Wk 2 | Wk 4 | Stat[3] |
| Exp | 15 | 0 | 11 | 12 | 12 | 14 | P☐ .0003 | 0 | 13 | 14 | 14 | 15 | P☐ .0001 |
| Ctl | 13 | 0 | 0 | 1 | 2 | 3 | | 0 | 0 | 0 | 0 | 0 | |

[1]N = total number of animals evaluated
[2]The total number of animals showing CTM functioning when measurements were made within 30 minutes of surgical lesioning of the spinal cord - but prior to the PEG or sham treatment. Note that both CTM reflexes and SSEP conduction was eliminated in all animals.
[3]The number of animals showing recovery of either CTM functioning or SSEP conduction at the times specified.
[4]The P values for all comparisons between control and experimental animals at each time point; Fishers Exact Test, two tailed.

In general, back skin contracts towards the point of stimulus when the CTM reflex is activated. The largest response usually occurs ipsilateral to the point of stimulation, as the reflex is largely laid out bilaterally. However, there is a minor contralateral contraction in response to ipsilateral stimulation of the skin, thus details of the region of peak skin contraction on both sides of the midline are provided with reference to the focal area of stimulation in Table 7. Only 6 examples of 52 separate comparisons (Experimental and Control; left and right side) were observed where the peak contraction was directed away from the focal stimulus in the uninjured animal, emphasizing that this is normally an infrequent occurrence. When the direction of skin contraction, its angle, and velocity were compared between the preinjury and postinjury data in PEG-treated animals, there was no statistical difference—thus the recovered reflex was faithfully reproduced by PEG treatment (Table 6).

An evaluation was also made of the change in direction of skin contraction on both left and right sides of the animals by paired comparison of the angle of skin contraction in only PEG-treated animals (as will be emphasized below, control CTM behavior did not change at all following its spontaneous recovery and in only three animals). The mean angle of skin contraction following ipsilateral CTM stimulation was not significantly different after PEG mediated recovery than the normal CTM in the same animals prior to injury (P=0.43, Mann Whitney, two tailed paired comparison) as was the contralateral responses (P=0.44, same test). In the three spontaneous recoveries in control animals, the peak distance of contraction and its velocity (1 mm, and 25 mm/sec respectively) was identical in two, and the recovered reflex unchanged. In the third, only a reduction of the velocity of CTM contraction was measured while the angle of contraction and the peak distance of contraction remained unchanged (Table 6).

TABLE 7

Characteristics of CTM recovery prior to, and 1 month after Injury

Cutaneous Trunci Muscle Performance

|     |            | N[1] | Direction[2]      | Dist[3]   | Velocity (mm/sec)[4] | Range (mm/sec)[5] |
|-----|------------|------|-------------------|-----------|----------------------|-------------------|
| Exp | Pre[6]     | 11   | 10/11; (88.7±1.2) | 1.2±0.12  | 15.7 ± 1.9           | 8.4-25            |
|     | Post       | 15   | 13/15; (80.7±6.5) | 1.3±0.17  | 19.9 ± 4.4           | 8.4-50            |
|     | Statistic[7]|     | 0.2               | 0.62      | 0.4                  | —                 |
| Ctl | Pre        | 3    | 3/3 (90°)[8]      | 1.0[8]    | 25[8]                | —                 |
|     | Post       | 3    | 3/3 (90°)[8]      | 1.0       | 20.8 ± 4.2           | —                 |

CTM Angle of Contraction

|      | Ipsilateral | | | | | Contralateral | | | |
|------|---|---|---|---|---|---|---|---|---|
|      | N | X[10] | SEM[10] | Range | Statistic | X[10] | SEM[10] | Range | Statistic |
| Pre  | 11 | 45 | 18.7 | -90/90 | P = 0.44 | 49.4 | 25.9 | -90/90 | 0.43 |
| Post | 11 | 70 | 24.2 | -80/90 |          | 19.4 | 25.1 | -90/90 |      |

[1] N = total animals in presurgery and postsurgery data sets
[2] The direction and angle of orientation of CTM skin contraction. The number of observations where skin pulled towards the stimulus is given over the total animals evaluated. The angle of skin contraction is expressed relative to an imaginary line perpendicular to the long axis of the animal, and the mean angle of contraction and its standard error for those animals is given in parenthesis.
[3] The mean distance of peak contraction and its standard error
[4] The mean velocity of CTM contraction and its standard error
[5] The minimum and maximum velocities for each group are given
[6] Four PEG treated animals did not receive a presurgery evaluation.
[7] Statistical evaluation, comparing the mean data in each column, used the Mann Whitney two tailed test.
[8] All three control animals were identical in these measurements, thus there was no standard error to report.
[9] The angle of skin contraction relative to an imaginary line perpendicular to the long axis of the animal. Contractions pulling towards the probe were assigned positive numbers, and negative numbers for contractions pulling away from it. The data is given for animals where the peak contraction of backskin was detected on the same side of the animal's midline as the stimulus (ipsilateral) and when the peak contraction was measured to be on the other side of the midline (contralateral). Note that this data is presented for PEG treated animals only since all three control recoveries were identical and all peak responses were ipsilateral to the point of stimulation. Note as well that the data obtained prior to surgery (Pre) was not statistically different from that obtained 1 month post surgery (Post).

Recovery of Conduction Through the Injured Spinal Cord

Figures 28A, 28B:
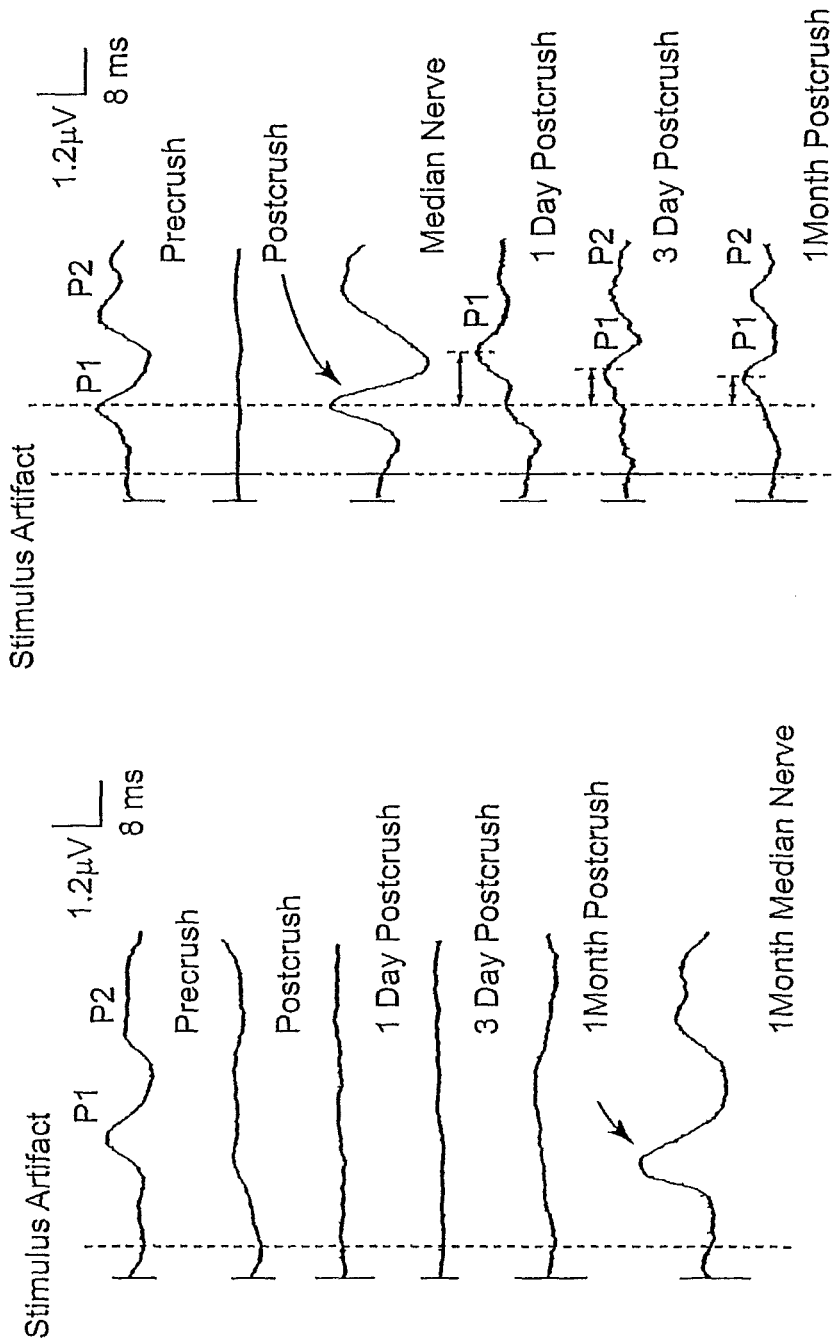
FIGS. 28A and 28B are graphs of evoked potentials measured in the test of Example 9.
Figure 29:
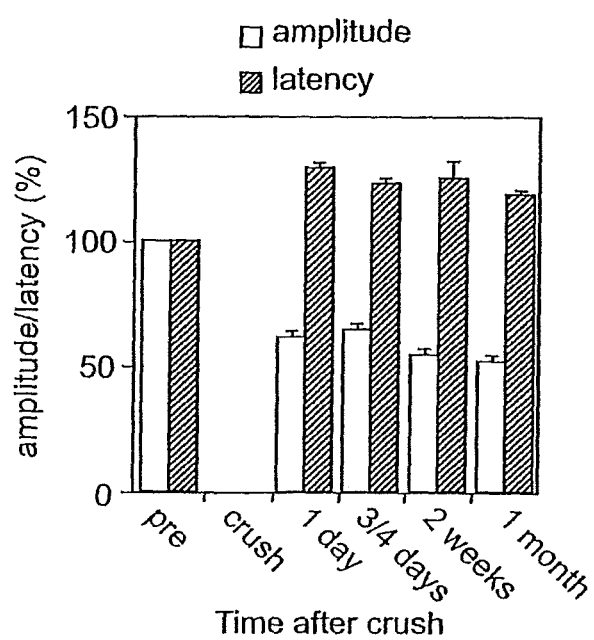
FIG. 29 is a bar graph showing amplitude and latency of recovered SSEPS in PEG treated animals per Example 9. The peak normalized amplitude of the early arriving SSEP is plotted for all time points as is the average latency (each represented as 100% for the preinjury histogram). Note that the average magnitude of the SSEP vacillates around about 50% of its preinjury level, while the latency incrementally declines. The latency at 1 month was statistically significantly reduced compared to day 1 measurements. The error bars are standard errors of the mean. Measurements from 13 animals total are shown for all points except at 2 weeks, where 9 animals were used for recordings.
Figure 30C:
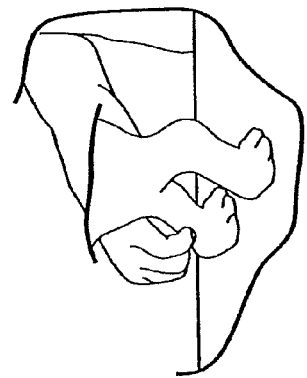
FIGS. 30A-30D depict a portion of a neurological examination for outcome measures and recovery from paraplegia. A dog is placed on its side while a neurologist tests for the presence of superficial pain (A), deep pain (B), and conscious proprioception (C and D). Skin of the flank and limbs was pinched sharply with hemostats probing for a reaction from the subject during tests of superficial pain response. Deep pain response was similarly determined, but by a sustained and sharp squeeze of the joints of the digits. Positive responses were provided for comparison by testing the fore limbs. The responses were quantified by a 1-5 score: 1=no detectable response; 2=a response at the limits of detection, indicated by an increased state of arousal, increased respiration or pulse; 3=consistent attention to the painful stimulus but without any overt defensive behavior; 4=mildly defensive behavior such as abrupt turning of the head towards the stimulus, and whining; 5=completely normal response to painful stimuli including yelping, biting, and aggressive behavior. These scores were obtained for both sides of the body and averaged. Conscious proprioceptive placing (CP) and weight support was tested in dogs by providing lateral support of the hind limbs, and turning one hind paw "under" so that the dorsal surface of the paw (and the animal's weight) rested on the table (inset C). A normal animal briskly replaces the paw to a normal stance instantly after the examiner releases the paw. Paraplegic animals rest in this "knuckled under" stance for extended periods of time. Testing the fore leg provided a positive control. The test was performed on each side of the body, and scored on each side: 1 point=complete absence of CP, and 2.5 points for a positive CP response. These scores were then summed for each animal. Voluntary locomotion (not shown) was evaluated with a similar 1-5 point score: 1=complete inability to step or voluntary ambulate; 2=stepping and load bearing at the limit of detection, at best a few steps before falling (paresis); 3=longer sequences of stepping, poorly coordinated before falling (paresis), and unable to climb stairs; 4=more robust and effective walking but with clear deficits in coordination, effective weight support, but able to climb stairs; 5=completely normal voluntary walking, indistinguishable from a normal animal. All neurological exams were videotaped for reference and half points were permitted at the examiner's discretion. A total neurological score (TNS) was determined for each animal at each testing period by summing the scores of these 4 independent tests. Thus the range of a possible score for any one animal was 4 (a totally paraplegic animal) to 20 (a totally normal animal, indistinguishable from an uninjured one).
Figure 30D:
Figure 30B:
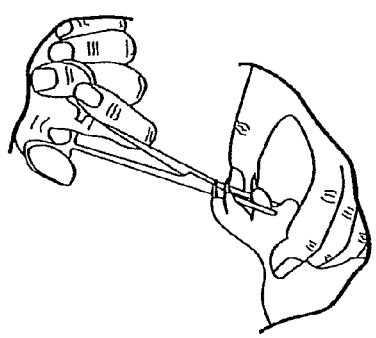
Figure 30A:
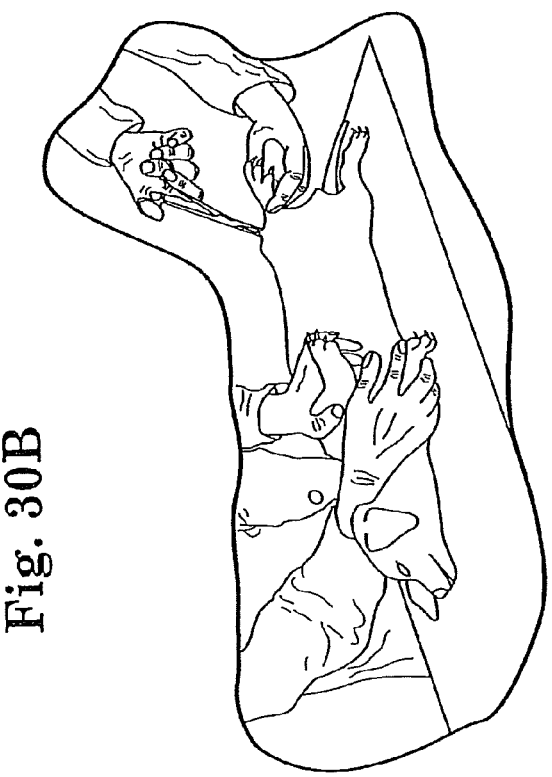
Figure 30E:
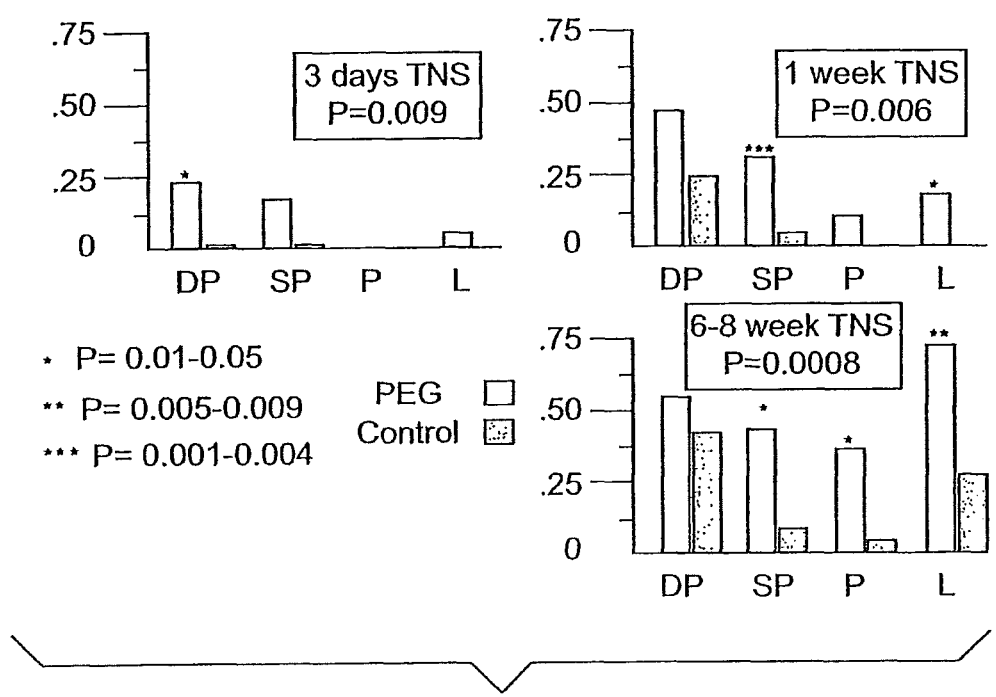
FIG. 30E shows a comparison of control and PEG-treated animals (FIG. 30A-30D) for each of the four outcome measures at approximately 3 days post injury (about 48 hours after the last PEG injection), 1 week, and 6-8 weeks post injury. The γ-axis for each bar graph is the percentage of the population (i.e., 25, 50, 75%). DP=deep pain, SP=superficial pain, P=proprioceptive placing, and L=voluntary locomotion. Asterisks note when a test for proportions (Fisher's exact test, two tailed) or a comparison of the means (Students T, or the Welch variation) revealed statistical significance. Note the clear recovery of outcome measures within 48 hours of the last PEG injection in that group, and the striking improvement in TNSs in PEG-treated dogs at every period of evaluation.

As in previous studies, SSEPs usually segregated into 2 peaks following tibial stimulation in the uninjured animal: an early arriving peak (about 20-35 ms), and a late arriving peak (40-50 ms). Table 6 shows the proportion of animals recovering an SSEP in the experimental population, which was 87% during the first day following PEG treatment, and by week 4 had reached 100%. Not one sham-treated animal recovered conduction during the same period of time (Table 6). FIG. 28A shows a typical example of SSEP records for sham treated animals, as well as a median nerve control procedure. Such control procedures were undertaken for any measurement that failed to demonstrate a repeatable SSEP, and in every case demonstrated that the lack of evoked potentials was due to a failure to conduct them through the lesion. In FIG. 28B, a typical process of PEG mediated recovery is shown. Note that the latency of the recovering evoked potentials was greater than normal in the early stages of recovery, but gradually declined with time (depicted for the early arriving peaks). FIG. 29 shows that normal latency was not reached during the 1 month of observation. FIG. 29 also plots the magnitude of the early arriving evoked potentials—which recover to more than 50% of their pre-injury values.

Discussion

This example confirms that PEG treatment can reverse behavioral loss and conduction loss secondary to severe spinal cord injury within hours. Here the focus has been exclusively on the delayed application of PEG to a standardized spinal cord injury. The constant displacement injury technique produces measurable pathology that is not statistically significantly different between individual animals in the group [Moriarty, L. J., Duerstock, B. S., Bajaj, C. L., Lin. K and Borgens, R. B. (1998): Two and three dimensional computer graphic evaluation of the subacute spinal cord. injury, J. Neurologic. Sci., 155:121-137]. However PEG mediated reversals are so rapid, with functional recoveries occurring in sometimes less than an hour, that injured animals can also serve as their own controls [Borgens, R. B. and Shi, R. (2000): Immediate recovery from spinal cord injury through molecular repair of nerve membranes with polyethylene glycol, FASEB, 14:27-35].

In this example, the character of the behavioral recovery is evaluated by comparing its characteristics to the pre-injury reflex. The results show that the recovered reflex activity is statistically similar in the direction, distance, and velocity of CTM contractions when compared to the normal reflex. The entire receptive field lost after injury was not restored however. The largest unit area recovered by PEG treatment approached 50% of the original area of areflexia. Only three control animals showed spontaneous recovery of the CTM reflex. Curiously, these animals displayed a recovered CTM that was mostly identical to the preinjury CTM reflex. This could be due to a slightly less severe injury in these animals— requiring possibly less robust spontaneous sealing to restore the reflex behavior without any measurable change in it. In PEG-treated animals, there were numerous small alterations in the character of the restored reflex in the treated population—however these changes were not statistically significant relative to the preinjury CTM reflex.

In summary, direct application of this hydrophilic polymer to the site of a spinal cord injury can rapidly reverse behavioral loss restoring an appropriately organized behavior as well as nerve impulse conduction through the lesion within a clinically useful time frame.

PEG-Mediated Repair of Neural Injury

This example is one of a series detailed herein that has explored the ability of a cell fusogen or biomembrane fusion agent such as PEG to reconnect severed mammalian spinal cord axons, as well as seal the axolelmma of severely compressed/crushed spinal axons [Shi, R., Borgens, R. B. and Blight, A. R. (1999): Functional reconnection of severed mammalian spinal cord axons with polyethylene glycol, J. Neurotrauma, 16: 727-738; Shi, R. and Borgens, R. B. (1999): Acute repair of crushed guinea pig spinal cord by polyethylene glycol, J. Neurophysiology, 81: 2406-2414]. The potential mechanisms of action of biomembrane fusions agents such as PEG are discussed elsewhere herein, as well as the possibly shared mechanisms with non-ionic triblock polymers such as the poloxamines and poloxamers discussed below [see Borgens, R. B. and Shi, R. (2000) Immediate recovery from spinal cord injury through molecular repair of nerve membranes with polyethylene glycol, FASEB, 14: 27-35; Shi, R. and Borgens, R. B. (1999): Acute repair of crushed guinea pig spinal cord by polyethylene glycol, J. Neurophysiology, 81: 2406-2414; Shi, R., Borgens, R. B. and Blight, A. R. (1999): Functional reconnection of severed mammalian spinal cord axons with polyethylene glycol, J. Neurotrauma, 16: 727-738]. Briefly; sealing of membrane breaches by high molecular weight molecules such as PEG may involve a dehydration of the plasmalemma where closely apposed regions of the bilayer resolve into each other—structural components of the plasmalemma no longer partitioned by the polar forces associated with the aqueous phase. Subsequent to the removal of the fusogen and rehydration, the now continuous phase undergoes spontaneous reassembly. We have shown that the restored membrane is repaired sufficient to exclude uptake of a large molecular weight intracellular tracer [Borgens, R. B. and Shi, R. (2000) Immediate recovery from spinal cord injury through molecular repair of nerve membranes with polyethylene glycol, FASEB, 14: 27-35]—but is still porous to a limited exchange of ions, in particular potassium [Shi, R. and Borgens, R. B. (1999): Acute repair of crushed guinea pig spinal cord by polyethylene glycol, J. Neurophysiology, 81: 2406-2414]. The magnitude of recovered CAPs in spinal cord strips in isolation can nearly be doubled by the addition of the fast potassium channel blocker 4 aminopyridine [Shi, R. and Borgens, R. B. (1999): Acute repair of crushed guinea pig spinal cord by polyethylene glycol, J. Neurophysiology, 81: 2406-2414]. Membrane fusion processes are still an active area of research—particularly as models for endogenous membrane and vesicle fusion [see Lee, J. and Lentz, B. R. (1997): Evolution of lipid structures during model membrane fusion and the relation of this process to cell membrane fusion, Biochemistry, 36: 6251-625; Lentz, B. R. (1994): Induced membrane fusion; potential mechanism and relation to cell fusion events, Chem. Physiol. Lipids, 73: 91-106].

Physical reconnection of axons contained within severed strips of guinea pig spinal cord ventral white matter was demonstrated in vitro using a double sucrose gap isolation and recording chamber. Reconnection of white matter was documented by the immediate recovery of CAPs traversing the original plane of transection following fusion as well as by the diffusion of two intracellular fluorescent labels and by high-resolution light microscopy [Shi, R., Borgens, R. B. and Blight, A. R. (1999): Functional reconnection of severed mammalian spinal cord axons with polyethylene glycol, J. Neurotrauma, 16: 727-738]. Immediate recovery of conduction across severe crush lesions to ventral white matter in vitro was documented by similar techniques [Shi, R. and Borgens, R. B. (1999): Acute repair of crushed guinea pig spinal cord by polyethylene glycol, J. Neurophysiology, 81: 2406-2414]. In all studies, an application of an aqueous solution of PEG (50% by weight in distilled water) was used for 2 minutes. No difference in response using PEG solutions prepared with polymers of 400 to about 3000 MW (ibid.) has been detected, but the viscosity of the solution may still be more important to PEG mediated repair than the MW of the polymer in this regard. This may be more important to eventual clinical use if topical applications of PEG to the damaged neural tissue are required.

Membrane Repair in Other Types of Injury

Non-ionic detergents, so called triblock polymers, are similar to PEG, and are believed to share some mechanisms of action in reversing cell permeabilization. Their structure usually incorporates a high molecular weight central hydrophobic core, with hydrophilic PEG side chains. Poloxamer 188 has proven to reverse muscle cell death subsequent to high voltage insult [Lee, R., River, L. P., Pan, F. S., Wollmann, L., (1992) Surfactant-induced sealing of electropermeabilized skeletal muscle membranes in vivo, Proc. Natl. Acad. Sci. U.S.A. 89, 4524-4528]. Isolated rat skeletal muscle cells were labeled with an intracellular fluorescent dye which leaked out of the cells after high voltage trauma. This insult was sufficient to disrupt muscle membranes allowing the leakage of the marker in 100% of the control preparations. Treatment of skeletal muscle cells in vitro with P188 reduced—even eliminated—dye leakage following the injury. Further in vivo tests extended these results since an intravenous injection of P188 produced a physiological and anatomical recovery of the rat muscle following electric shock [Lee, R., River, L. P., Pan, F. S., Wollmann, L., (1992) Surfactant-induced sealing of electropermeabilized skeletal muscle membranes in vivo, Proc. Natl. Acad. Sci. U.S.A. 89, 4524-4528]. This approach has also been tested to reverse cell death in a testicular reperfusion injury model in rats [Palmer, J. S. Cromie, W. L. and Lee, R. C. (1998): Surfactant administration reduces testicular ischemia-reprefusion injury, J. Urology, 159: 2136-2139] P188 can also seal heat shocked muscle cells in vitro. This was shown by an inhibition of calcein dye leakage from cells induced by elevated temperature [Padanlam, J. T., Bischof, J. C. Cravalho, E. G. Tompkins, R. G. Yarmush, M. L. and Toner, M. (1994) Effectiveness of Poloxamer 188 in arresting calcein leakage from thermally damaged isolated skeletal muscle cells, *Ann N.Y. Acad. Sci.* 92 111-123]. P188 also rescues fibroblasts from lethal heat shock [Merchant, F. A., Holmes, H. A., Capelli-Schellpfeffer, M., Lee R. C. and Toner, M. (1988) Poloxamer 188 enhances functional recovery of lethally heat-shocked fibroblasts, J. Surgical Research 74 131-140]. Another biocompatible detergent (Poloxamer 1107; administered IV) was used in an in vivo testicular ischemia—reperfusion injury model in rats, as well inhibiting the leakage of hemoglobin from irradiated erythrocytes [Palmer, J. S. Cromie, W. L. and Lee, R. C. (1998): Surfactant administration reduces testicular ischemia-reprefusion injury, J. Urology, 159: 2136-2139; Hannig, J., Yu, J., Beckett, M., Weichselbaum R., and Lee, R. C. (1999): Poloxamine 1107 sealing of radiopermeabilized erythrocyte membranes, Int. J. Radiat. Biol., 75: 379-385]. These studies demonstrate that nonionic biocompatible detergents and large hydrophilic molecules can reverse permeabilization of cell membranes, and that they can also be administered through the vascular system to reach damaged target cells.

EXAMPLE 10

Intravenous Hydrophilic Polymer Induces Rapid Recovery from Clinical Paraplegia in Dogs This example demonstrates a swift, striking, and statistically significant recovery of multiple functions in clinical cases of severe, acute, naturally occurring paraplegia in dogs. Recovery of function occurred in response to a combination of topically applied, and intravenously administered, polyethylene glycol (PEG). Recoveries of sensory and motor functions occurred rapidly and at all time points studied between 3 days and 6-8 weeks post-injury.

Admission and Treatment

Dogs with spinal cord injuries were admitted to the emergency services of the University Veterinary Teaching Hospitals (UVTH) at Texas A&M University, College Station, Tex., and at Purdue University, West Lafayette, Ind. An identical protocol for admission, neurological evaluation, treatment, and follow up (R. B. Borgens et al., *J. Restorative Neurology and Neurosci.* 5, 305 (1993); R. B. Borgens et al., *J. Neurotrauma* 16, 639 (1999)) was adhered to by each Research Center. In special circumstances, computerized x-ray tomography (CT) imaging was available in addition to routine radiography and myelography at the Texas Center, while electrophysiological study of nerve impulse conduction through the spinal cord lesion by evoked potential testing was performed at Purdue University.

Each dog received a radiological examination (FIGS. 30A-30D), and a thorough, videotaped, neurological examination (FIG. 31A) that included: 1) tests for deep pain in hind limbs and digits, 2) superficial pain appreciation below the level of the injury in flank, lower limbs and digits, 3) proprioceptive evaluation of the hind limbs (i.e. conscious proprioception), 4) evaluation of hind limb load-bearing and voluntary locomotion, and 5) spinal reflex testing (patellar, tibialis, cranialis, flexor withdrawal, and sciatic reflexes). Tests 1-4 were also used as functional measures of outcome and were quantitatively scored using previously reported techniques and methods (R. B. Borgens et al., *J. Restorative Neurology and Neurosci.* 5, 305 (1993); R. B. Borgens et al., *J. Neurotrauma* 16, 639 (1999)). These data then provided a total neurological score (TNS) (R. B. Borgens et al., *J. Restorative Neurology and Neurosci.* 5, 305 (1993); R. B. Borgens et al., *J. Neurotrauma* 16, 639 (1999)) for each dog at each time point tested. Since neurological recovery is varied in its expression between animals, the most valid means to compare outcomes is by comparison of the TNS(R. B. Borgens et al., *J. Restorative Neurology and Neurosci.* 5, 305 (1993)). All dogs admitted to the clinical trial possessed the worst clinical signs for spinal injury secondary to spinal cord compression characterized by complete paraplegia, urinary and fecal incontinence, and lack of deep pain response [grade 5 lesions (J. R. Coates, *Common Neurological Problems* 30, 77 (2000))]. These functional tests (and others, see below) were also used as exclusion criterion so that neurologically "incomplete" dogs were not included in the trial. Additionally, only paraplegic dogs with upper motor neuron syndrome—true spinal cord injuries—were study candidates. A persistent lack, or hyporeflexia of the lower limb(s) revealed segmental compromise of spinal cord circuitry or "lower motor neuron sequela". This was sufficient to exclude animals from the study (R. B. Borgens et al., *J. Restorative Neurology and Neurosci.* 5, 305 (1993); R. B. Borgens et al., *J. Neurotrauma* 16, 639 (1999)). During the initial clinical evaluation, owners were asked to review a document concerning the experimental treatment, and then requested to sign an informed consent should they wish to participate in the study.

Next, paraplegic dogs received the first of two intravenous injections of PEG. Later, but within 24 hours of admission, the location of the lesion was determined by survey radiography and myelography (FIG. 1). The latter examination insured that myelomalacia was limited to less than 1 vertebral segment. All dogs received an injection of methylprednisolone sodium succinate (30 mg/kg body weight), underwent general anesthesia, and taken to surgery. All injured dogs received standard-of-care veterinary management of these injuries, including surgical decompression of the affected site and fixation of the vertebral column when required. The dura was removed during decompressive surgery, exposing the spinal cord lesion, and about 1 cc of the PEG solution (about 2000 daltons, 50% W/W in sterile saline; 150 mg/kg body weight) was layered onto the injury site. The polymer was aspirated from the surface of the exposed cord within 2 min of application, next the region lavaged with sterile Ringer's solution, and these fluids aspirated as well. A fat pad graft was placed superficially, the incision closed, and the animals taken to the Intensive Care Unit (ICU) for recovery. Within 24 hours of surgery, a second injection of PEG, identical to the first, was performed usually in ICU. Animals were monitored within the hospital for 7-10 days, and a full neurological exam, videotaped as was the original, was performed approximately 3 days (74±9 hours) post surgery, approximately 1 week post surgery at discharge (6.8 days±1.2 days) and at 6-8 weeks post surgery at recheck. As in past clinical trials, owners were provided detailed instructions concerning care of their animals (i.e. bladder expression, skin care, etc.) and, initially, use of a wheeled cart (K-9 Carts, Montana) to aid in the dog's rehabilitation (R. B. Borgens et al., *J. Restorative Neurology and Neurosci.* 5, 305 (1993); R. B. Borgens et al., *J. Neurotrauma* 16, 639 (1999)). However this latter practice was discontinued after only 3 admissions because the recovery of function was so rapid (see below) such as to make the use of the cart unnecessary.

Control Dogs

During the development of the experimental protocol, paraplegic dogs recovered rapidly and unexpectedly within a few days after PEG administration. Participating neurosurgeons believed it unethical to carry out a control procedure (intravenous injection of the solvent for PEG-sterile saline) knowing full well these client-owned animals would sustain variable, but severe, life long behavioral losses (R. B. Borgens et al., *J. Neurotrauma* 16, 639 (1999)). Given the ca. 48-hour window in treatment, it was also not possible to perform a single cross-over study. Thus a medical decision was made to use historical controls rather than inject such severely injured animals with sterile salt water. Relevant historical control data was obtained for sham-treated dogs from recent peer reviewed and published studies performed at the Indiana Center (R. B. Borgens et al., *J. Restorative Neurology and Neurosci.* 5, 305 (1993); R. B. Borgens et al., *J. Neurotrauma* 16, 639 (1999)). These control dogs were 1) also admitted to veterinary clinical trials restricted to only neurologically complete cases of acute canine paraplegia, 2) received identical conventional management as described above, 3) were neurologically evaluated by identical methods, and excluded from the studies by identical exclusion criteria (R. B. Borgens et al., *J. Restorative Neurology and Neurosci.* 5, 305 (1993); R. B. Borgens et al., *J. Neurotrauma* 16, 639 (1999)) (see FIGS. 30A-30E and FIGS. 32A and 32B) were evaluated at the same time points, and 5) in most cases, their neurological scores were derived by the same investigators participating in this trial (R. W., G. B., J. T., R. B). It is important to emphasize that all investigators were completely blinded to the experimental or control status of all dogs recruited into these previous trials. The use of these identical procedures in recruitment and particularly in the scoring of neurological functions yielded little to no variation between the multiple investigators when their individual scores were compared (R. B. Borgens et al., *J. Restorative Neurology and Neurosci.* 5, 305 (1993); R. B. Borgens et al., *J. Neurotrauma* 16, 639 (1999)). The validity of this comparison appears to be eminently greater than data gathered from the veterinary literature. These latter investigations do not: i) use multiple neurological functions as exclusion criteria to limit the possibility that evaluations would include neurologically incomplete dogs, ii) report a complete axis of neurological behavior including the function of relevant lower spinal reflexes, use the outcome measures used here, or iv) evaluate animals at the same post-surgical time points post surgery.

For our comparison complete medical records, score sheets, and video tapes were available for 14 control (sham-treated) dogs from 1993 (R. B. Borgens et al., *J. Restorative Neurology and Neurosci.* 5, 305 (1993)) and 11 control dogs from 1999 (3)—25 dogs total for comparison to 20 PEG-treated dogs. Moreover, in the latter clinical trial (R. B. Borgens et al., *J. Neurotrauma* 16, 639 (1999)), the experimental application (oscilating field stimulation) was delayed in 12 experimental dogs for about 96 hours after surgery to determine what, if any, early functional recovery could be associated with surgery and steroid treatment alone. The neurological status of this subset of dogs was reported (R. B. Borgens et al., *J. Neurotrauma* 16, 639 (1999)). These data then, provided a total of 37 control dogs to compare to 20 PEG-treated dogs at the 3 day time point, and 25 control dogs for comparison at the 1 week and 6-8 week neurological checkups.

Clinical Responses to Polymer Administration in Paraplegic Dogs

The most sensitive indicator of early functional recovery in clinical cases of neurologically complete canine paraplegia is the reappearance of deep pain response in hind limbs and digits (R. B. Borgens et al., *J. Restorative Neurology and Neurosci.* 5, 305 (1993); R. B. Borgens et al., *J. Neurotrauma* 16, 639 (1999); J. R. Coates, *Common Neurological Problems* 30, 77 (2000)). This was evaluated in 17 of the 20 acutely injured PEG-treated dogs approximately 3 days after surgery (approximately 48 hours after the second injection of PEG (FIG. 2). During this time, 4 of the 17 PEG-treated dogs recovered deep pain, while only one of the 37 control dogs had (P=0.03; Fisher's exact test, two tailed, in this and all subsequent comparison of proportions).

Comparison of the mean TNS at this time, a numbers derived largely from recoveries in deep and superficial pain, was markedly statistically significantly improved in the PEG-treated group compared to controls (P=0.009; comparison of means here and below were made using a Students' T test, two tailed, or the Welch variation, FIGS. 30A-30E).

Though more than half of the population of PEG-treated dogs had recovered deep pain responses by 1 week post-treatment, improvements in deep pain in 25 control dogs eliminated significance in this one functional comparison between the groups at this time point (P=0.2). However, recoveries in proprioception, improvement in load bearing in hind limbs and voluntary walking in 8 PEG-treated dogs of 20 at this time were unmatched by such improvements in control dogs. Analysis revealed marked statistically significant improvement in the TNSs of PEG-treated dogs at this time point (P=0.007; FIGS. 30A-30E).

The total neurological scores of control dogs showed modest and progressive improvement by the 6-week recheck, however, this remained manifest as mainly improvements in the quality of pain appreciation (R. B. Borgens et al., *J. Restorative Neurology and Neurosci.* 5, 305 (1993); R. B. Borgens et al., *J. Neurotrauma* 16, 639 (1999)). Thus, there was no significant difference between the PEG-treated and control dogs when the proportions of animals with positive deep and superficial pain responses were compared (P=0.1 and 0.6, respectively). However, this improvement in pain appreciation was not matched by any of the other outcome measures evaluated in control dogs. Thirty-five percent (7 of 20) of the PEG-treated dogs recovered measurable proprioception by 6 weeks, while only 1 of 25 (4%) of control animals had improved proprioception (P=0.01). Fully 70% of all PEG-treated dogs (14 of 20) could ambulate voluntarily, compared to only 28% (7 of 25) of controls (P=0.007). Furthermore, the overall quality of functional recovery secondary to PEG administration at the 6 week recheck (as given by the total neurological score) was strikingly improved by PEG treatment relative to controls (P≤0.0008; FIGS. 30A-30E).

Qualitatively, the two groups appeared quite different in a manner masked by the dry recitation of quantitative neurological scores and proportions. The possible range of an individual dog's total neurological score was 4 (a totally paraplegic dog) to 20 (a totally normal dog (see FIGS. 30A-30E). Fifteen of the 25 control dogs (60%) remained neurogically complete paraplegics 6-8 weeks after decompressive surgery and corticosteroid treatment, all were individually assessed a neurological score of 4. The best performing control dog scored 11 at this time point (R. B. Borgens et al., *J. Neurotrauma* 16, 639 (1999)). However, this animal remained seriously impaired; locomotion alone was evaluated as only a score of 2. PEG treatment resulted in 35% (7 dogs of the 20) individually scoring 13 to 16. By the 6-8 week recheck some dogs had made a such a striking recovery—to the extent any remaining functional loss could only be determined by a thorough neurological examination. Only 3 of 20 PEG-treated dogs (15%) remained paraplegic at the end of the 6-8 week period of observation (a highly significant comparison to controls, P=0.003).

Electrophysiology and Bladder Management

Figure 31A:
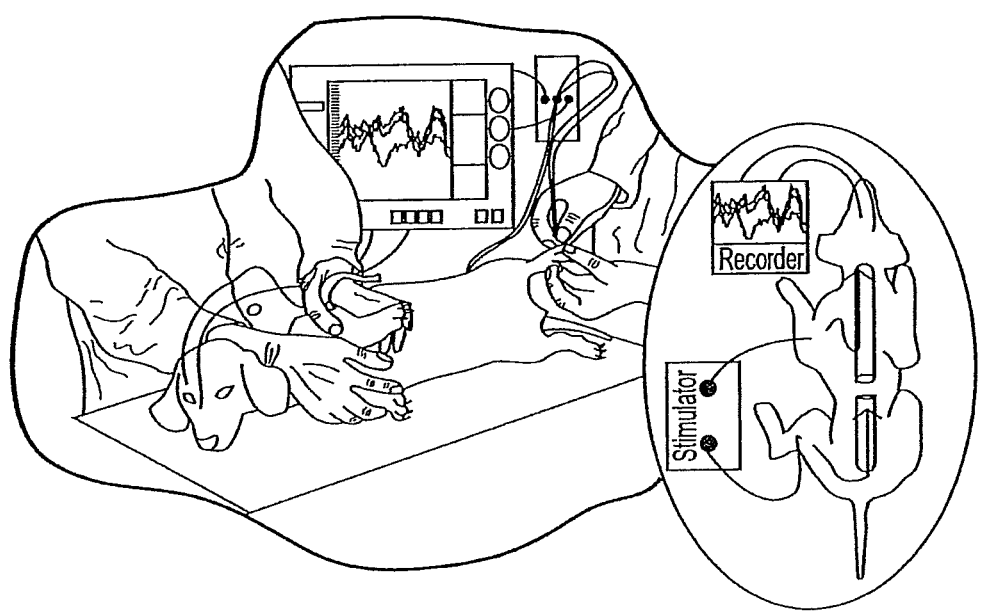
FIG. 31A shows a sedated dog and electrode placement in electrophysiological tests for conduction through a spinal cord injury to determine a Somatosensory Evoked Potential (SSEP). At each evaluation, four to seven sets of evoked potentials (SSEPs) were stimulated, recorded, averaged, and stored using a Nihon Kohden ME#B-5304K 4 Neuropak recorder. More particularly.
Figure 31B:
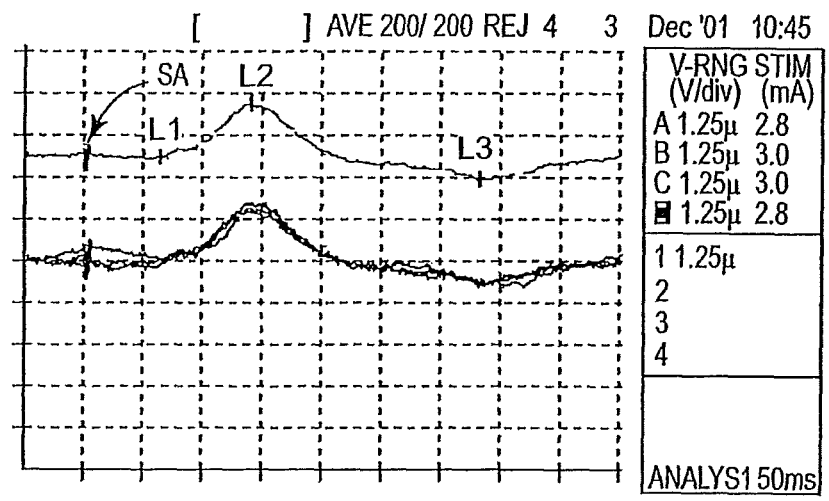
FIG. 31B is a graph of a complete set of SSEP recordings from the procedure of FIG. 31A. A lower group of waveforms in this pair are the three individual trains of 200 stimulations as discussed, and an upper waveform is the averaged evoked SSEP (only such averaged SSEPs are provided in subsequent records, FIGS. 32A and 32B). This record is of a control procedure. Note the clear evoked potential, recorded approximately 10 ms after stimulation of the median nerve.
Figure 31C:
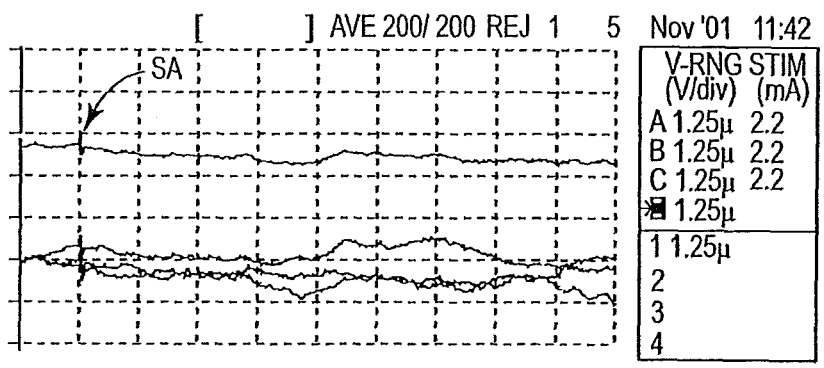
FIG. 31C is a graph showing a portion of an electrical recording, displaying three trains of stimulation, as well as the averaged SSEP as in FIG. 31B. This record was in response to stimulation of the tibial nerve in the same paraplegic dog providing the record in FIG. 31B, approximately 4 days post-injury. The complete elimination of SSEP conduction through the lesion is characteristic of all neurologically complete paraplegic animals meeting the criteria described in the text, both in this and all previous reports using identical procedures (R. B. Borgens et al., *J. Restorative Neurology and Neurosci.* 5, 305 (1993); R. B. Borgens et al., *J. Neurotrauma* 16, 639 (1999)). SA=stimulus artifact; time base=50 msec full screen, 5 msec/div; sensitivity=1.25 μV/div.
Figure 32A:
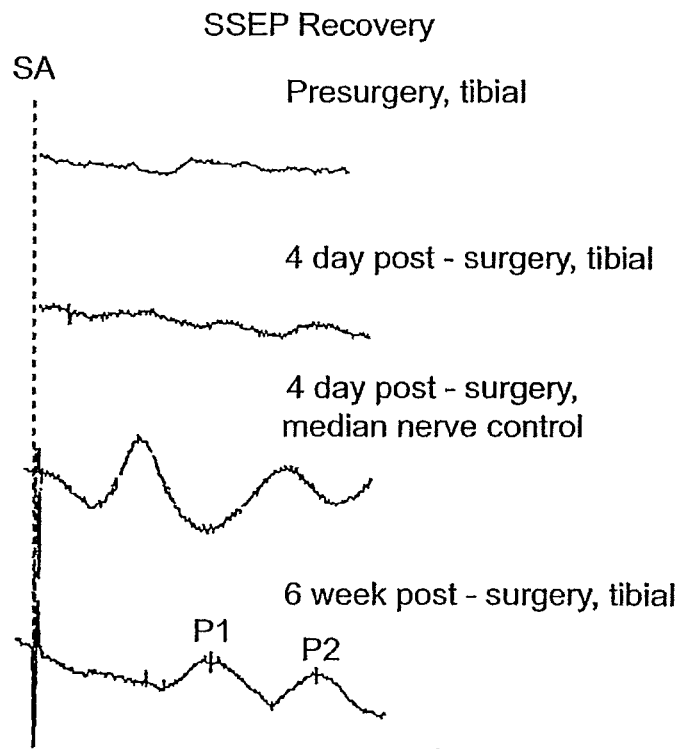
FIGS. 32A and 32B relate to PEG induced recovery of nerve impulse conduction through the site of spinal injury.
Figure 32B:
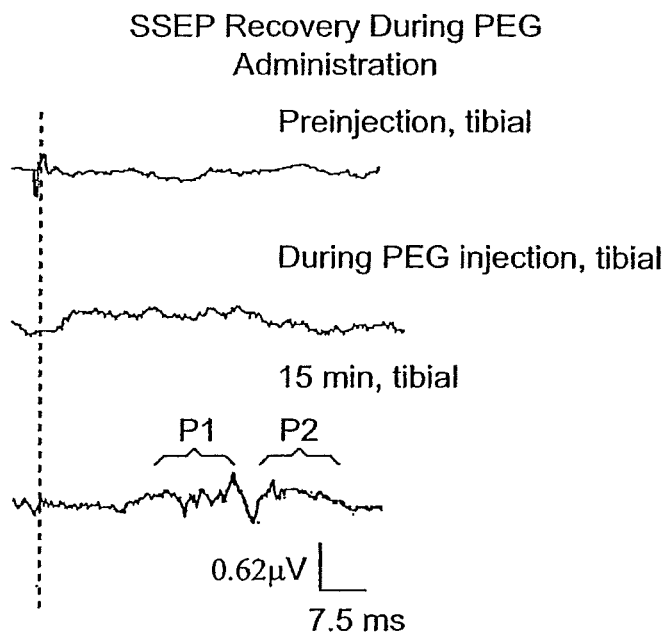

Evoked potential testing [Somatosensory Evoked Potential or SSEP (R. B. Borgens et al., *J. Restorative Neurology and Neurosci.* 5, 305 (1993); R. B. Borgens et al., *J. Neurotrauma* 16, 639 (1999)), FIGS. 31A-31C] was performed on 11 of the 12 PEG-treated dogs recruited to the Purdue Center to determine if nerve conduction through the lesion had been restored (FIGS. 31A-31C). Somatosensory Evoked Potential recordings could not usually be obtained prior to the first PEG injection and surgery due to the need to move these animals through the battery of evaluations and on to surgery as soon as possible after admission. In addition, most dogs were unable to be sedated for such tests in the first few hours after admission due to food intake and other complicating factors. Of the 11 dogs on which electrophysiological tests of conductance were performed at more than two recheck periods, 7 were recorded to have positive SSEPs, while 4 did not demonstrate evidence of nerve impulse conductance through the lesion. All four dogs scoring above the median TNS of 12 showed a clear recovery of conductance through the lesion. Furthermore, one severely injured animal (fracture/dislocation and subluxation of the vertebral column) was accessible for SSEP testing during the second of two PEG injections. This animal showed a progression from a negative SSEP (flatline) to low amplitude, long duration, cortical potentials during the 30 min period of injection and observation of the sedated animal (FIGS. 32A, 32B).

In contrast, of the 11 control dogs from the 1993 study, none recovered SSEP conduction by even 6 months post injury [refer to page 313 (R. B. Borgens et al., *J. Restorative Neurology and Neurosci.* 5, 305 (1993))]. Only two control dogs of 14 recovered measurable conduction by 6-8 months in the 1999 clinical trial [refer to page 649 (R. B. Borgens et al., *J. Neurotrauma* 16, 639 (1999))]. This proportion of PEG-treated dogs (7 of 11) that recovered ascending electrophysiological conduction through the lesion was highly statistically significant compared to the relative lack of recorded evoked potentials in control dogs (P=0.001).

The status of bladder continence due to paraplegia is problematic in dogs just as in man. We have found that electrophysiological measurements of micturation (urethral pressure profilemetry and cystometry) while providing data relevant to isolating cases of lower motor neuron syndrome, do not correlate highly with observations of recovery of urinary continence particularly by owners (R. B. Borgens et al., *J. Neurotrauma* 16, 639 (1999)). Incontinence is not easily confused by owners, since it represents a major behavioral loss in the dog's "house training" and is the most common reason given for euthanasia of their pets. Moreover, a consistent failure of owners to manually express the bladder of incontinent dogs leads to readmission for urinary tract infection. Of the 20 PEG-treated dogs, owners reported all but 6 were continent, and did not require bladder expression. These latter animals were of a group of PEG treated dogs exhibiting the least recovery at the end of the study. We offer these facts as additional but modest evidence that recovery from paraplegia mediated by PEG likely improved or eliminated at least urinary incontinence as well.

Paraplegia in Laboratory Animals, Dogs, and Man

The history of spinal cord injury research can be characterized in some part by the quest for standardized injury methods and credible means to assay behavioral loss and recovery in laboratory animals—usually adult guinea pigs, rats, or cats. There has always been debate and controversy concerning both of these quests. In the former, the difficulty centers on various different techniques used to induce injury to the exposed spinal cord. For example, constant impact [usually standardized weight drop techniques (S. K. Somerson, and B. T. Stokes, *Exp. Neurol.* 96, 82 (1987))], constant compression of the spinal cord [using specially fabricated clips (A. S. Rivlin, C. H. Tator, *Surg. Neural.* 10, 39 (1978)) or forceps (A. R. Blight. *J. Neurologic. Sci.* 103, 156 (1990))] and partial or complete transection (R. B. Borgens, A. R. Blight, D. J. Murphy, *J. Comp. Neural.* 250, 157 (1986)), of the spinal cord have been employed and contrasted (R. B. Borgens, A. R. Blight, D. J. Murphy, *J. Comp. Neurol.* 250, 157 (1986)). With the exception of the latter technique, an important goal of these methods has been to reduce the variability in lesions, and to produce a central hemorrhagic injury typical of clinical injury in man (A. R. Blight. *J. Neurologic. Sci.* 103, 156 (1990); A. R. Allen, *J. Am. Med. Assoc.* 57, 878 (1911); C. H. Tator, M. J. Fehlings, *Neurosurg.* 75, 15, (1991)). While the successes of the different approaches can be debated relative to these goals, there is no question that modern laboratory injuries are made to the surgically exposed spinal cords of anesthetized animals producing an initially dorsal locus of injury. This is inconsistent with most clinical injuries where the initial site of SCI ("spinal cord injury") injury is anterior (ventral), and the impact is to the trunk of the body or neck (so called "closed" injuries). Moreover, during experimental insult to the cord, anesthesia provides neuroprotection (S. K. Salzman, M. M. Mendez, S. Sabato, et al., *Brain Res.* 521, 33 (1990)), and is a complicating factor. Thus, naturally-occurring injuries in dogs provide a more direct comparison to clinical injuries in man (R. B. Borgens, in *Spinal Cord Dysfunction, Volume III: Functional Stimulation*, L. S. Illis, Ed. (Oxford Medical Publications, Oxford, 1992), chap 5).

There have also been numerous and varied attempts to measure and/or quantitate the behavioral recovery from SCI in laboratory models of spinal injury. Measurement of hindlimb locomotion (M. D. Basso, M. Beattie, J. D. Bresnahan, *J. Neurotrauma* 12, 1 (1995)), or some form of it (A. S. Rivilin, C. H. Tator, *J. of Neurosurgery* 47, 577-581 (1977)), has dominated rodent studies of SCI—usually because of the underlying notion that the results might be relevant to lower limb locomotion in man even though there is no evidence to support such a view. Humans are the only obligatory bipedal mammals, and upright walking is completely dominated by supraspinal control (S. Mori, K. Matsuyama, E. Miyashita, K. Nakajima, M. Asanome, *Folia Primatologica* 66, 192 (1996)). In experimental SCI models, locomotion is dominated by locally controlled and generated stepping (S. Rossignol, R. Dubuc, *Curr. Opin. Neurobiol.* 4, 894-902 (1994); A. Naito, Y. Shimuza, Y. Handa, *Neurosci Res* 8, 281 (1990)). Such walking behavior is often called "spinal walking" to separate it from walking behavior that requires the restored transmission of nerve impulses through the spinal cord lesion from higher centers. Because restored nerve impulse traffic through the lesion is not required for voluntary ambulation in animals, walking behavior by itself does not represent a valid behavioral recovery with which to infer restored conduction through the lesion. This requires use of kinestheseological methods confirming fore limb and hind limb coordination during voluntary locomotion.

For all of the above reasons, no attempt has been made to develop even more complicated systems to grade walking behavior associated with clinical paraplegia in dogs. Instead, reliance is placed on a simple 5 point score that provides a reliable, precise reflection of increasing capabilities in ambulation, but without additionally attempting to indicate the neural mechanisms of action underlying it (R. B. Borgens' et al., *J. Restorative Neurology and Neurosci.* 5, 305 (1993); R. B. Borgens et al., *J. Neurotrauma* 16, 639 (1999)).

In the present example, whatever the mechanism underlying the return of voluntary walking—a strikingly significant number of dogs walked with superior capability than occurred in controls. Moreover, the statistically significant improvement in TNS is a clear indication of substantive, and meaningful recovery in several other clinically relevant areas of function, including: recovery in the neurological appreciation of both deep and superficial pain, recovery of ascending nerve impulse conductance through the lesion, recovery of conscious proprioception, as well as substantial load bearing and voluntary walking.

The strengths of these methods as applied to naturally occurring paraplegia are that they provide real potential for assessing the clinical importance of experimental therapies for human SCI (R. B. Borgens et al., *J. Neurotrauma* 16, 639 (1999); A. R. Blight, J. P. Toombs, M. S. Bauer, W. R. Widmer, *J. Neurotrauma* 8, 103-119 (1991)). The weakness of this SCI model is that little is learned about the biological basis for the response to treatment. This is more easily achieved in laboratory models where invasive physiological testing and anatomical techniques can be applied (R. B. Borgens, in *Spinal Cord Dysfunction, Volume III: Functional Stimulation*, L. S. Illis, Ed. (Oxford Medical Publications, Oxford, 1992), chap 5).

Polymer Application in Experimental SCI

Both topical and/or intravascular administration of polyethylene glycol (2000-3000 Daltons, approximately 30-50% W/W in water) has been documented to induce:
1) Rapid (minutes) anatomical fusion of severed white matter axons (R. Shi, R. B. Borgens, A. R. Blight, *J. Neurotraum* 16, 727 (1999)) and rapid sealing of anatomic breaches in both myelinated and unmyelinated axons of guinea pig ventral white matter (R. Shi, R. B. Borgens, *J. Neurophysiology* 81, 2406 (1999)). In both cases neural tissue was maintained and evaluated in vitro in a double sucrose gap recording chambers (R. Shi, A. R. Blight, *Neuroscience* 77, 553-562 (1997)).

2) Rapid (minutes) recovery of nerve impulse conduction through the lesion in these same studies (R. Shi, R. B. Borgens, A. R. Blight, *J. Neurotraum* 16, 727 (1999); R. Shi, R. B. Borgens, *J. Neurophysiology* 81, 2406 (1999))—or through severe and standardized crush injuries to the guinea pig spinal cord in vivo, measured by SSEP testing (R. B. Borgens, R. Shi, *FASEB* 14, 27 (2000); R. B. Borgens, D. M. Bohnert, *J. Neurosci. Res.* 66, 1179 (2001); R. B. Borgens, R. Shi, D. M. Bohnert, *J. Exp. Bio.* 205, 1 (2002)).

3) Rapid (hours to days) recovery of long-tract dependent spinal cord reflex (the cutaneous trunchi muscle or CTM reflex) (R. B. Borgens, R. Shi, *FASEB* 14, 27 (2000); R. B. Borgens, D. M. Bohnert, *J. Neurosci. Res.* 66, 1179 (2001); R. B. Borgens, R. Shi, D. M. Bohnert, *J. Exp. Bio.* 205, 1 (2002)), which is totally dependent on the integrity of an identified white matter column of axons within the ventral funiculus of the guinea pig (A. R. Blight, M. E. McGinnis, R. B. Borgens, *J. Comp. Neurol.* 296, 614-633 (1990)) and rat (E. Thierault, J. Diamond, *J. Neurophysiol.* 60, 446-447 (1988)) spinal cord.

A variable level of recovery of the CTM reflex (produced by compression of the spinal cord) occurred in >90% of PEG-treated guinea pigs, compared to a range of 0-17% in sham-treated control populations in three separate studies (R. B. Borgens, R. Shi, *FASEB* 14, 27 (2000); R. B. Borgens, D. M. Bohnert, *J. Neurosci. Res.* 66, 1179 (2001); R. B. Borgens, R. Shi, D. M. Bohnert, *J. Exp. Bio.* 205, 1 (2002)). The recovery of cortical potentials was documented as restored volleys of SSEPs measured to arrive at the sensory motor cortex following electrical stimulation of the tibial nerve of the hind limb. In all (100%) of the control guinea pigs, such nerve impulse conduction through the lesion was eliminated for the 1 month of observation. In PEG-treated animals, SSEPs recovered in 100% of the population in these same three investigations (R. B. Borgens, R. Shi, *FASEB* 14, 27 (2000); R. B. Borgens, D. M. Bohnert, *J. Neurosci. Res.* 66, 1179 (2001); R. B. Borgens, R. Shi, D. M. Bohnert, *J. Exp. Bio.* 205, 1 (2002)).

Mechanisms of Polymer Based Therapy for Neurological Injuries

The molecular mechanisms of action of, for instance, surfactants and tri-block polymers in sealing or fusing cell membranes have been reviewed in the literature. (R. B. Borgens, *Neurosurgery* 49, 370-379 (2001); B. R. Lentz, *Chem. Phys. Lipid* 73, 91 (1994); J. Lee, B. R. Lentz, *Biochemistry* 36, 6251 (1997); J. M. Marks, C—Y. Pan, T. Bushell, W. Cromie, R. C. Lee *FASEB J* 15, 1107 (2001).) Briefly: an initial mechanism common to all hydrophilic surfactants that may be beneficial to soft tissue trauma is the formation of a chemical film sealing defects in the cell membranes at the site of mechanical damage. However, it is the watery-hungry character of this class of hydrophilic polymers (PEG, EPAN, and some dextrans) that is believed to instantly dehydrate the membrane locally. Furthermore, either removal or rearrangement of water molecules in the vicinity of membrane breach permits the lipid core of the intact membrane surrounding the breach—and perhaps the structural elements suspended in it—to merge into each other. When the polymer is removed, or in lowered concentration, variable amounts of structural self-assembly occur in response to reintroduction of the aqueous phase of the membrane. Triblock polymers such as poloxamers are comprised largely of PEG—yet they also posses a hydrophobic component (polypropylene oxide) which may actually target breaches in membranes—inserting into the breach where the hydrophobic core of the membrane is exposed (J. M. Marks, C-Y. Pan, T. Bushell, W. Cromie, R. C. Lee *FASEB J* 15, 1107 (2001)). The long PEG side chains likely contribute to sealing in the fashion described above. We have tested poloxamer 188 in a spinal injury model in guinea pigs and have found no difference in the physiological and behavioral recoveries in response to PEG as described above. These findings suggest various polymers may prove beneficial for application to soft tissue trauma and other injuries to the nervous system (J. M. Marks, C-Y. Pan, T. Bushell, W. Cromie, R. C. Lee *FASEB J* 15, 1107 (2001); J. Donaldson, R. Shi, R. Borgens, *Neurosurgery* 50, 147-157 (2002)).

Likely any large molecular polymer like PEG or poloxamers, introduced to the blood supply, will target only regions of tissue trauma where there is a loss of vascular integrity. We have demonstrated this by observing accumulation of a fluorescently labeled PEG in crushed guinea pig spinal cord—comparing intravenous, subcutaneous, and peritoneal administration with a topical application of the polymer to the exposed lesion (R. B. Borgens, D. M. Bohnert, *J. Neurosci. Res.* 66, 1179 (2001)). Labeling was barely detectable or non-existent in intact regions of the spinal cord in these same animals.

Of the putative mechanisms of action for PEG, formal proof of its membrane sealing properties have been demonstrated. The uptake of extracellular applied labels such as horseradish peroxidase (HRP), ethidium bromide, or the leakage of lactic dehydrogenase into the extracellular space, are excellent indices of cell membrane compromise (R. Shi, R. B. Borgens, *J. Neurocytology* 29, 633-643 (2000)). Both uptake of, and leakage of, these intracellular labels from injured white matter of the spinal cord is strikingly reduced or eliminated by PEG administration. Furthermore, the susceptibility for axonal sealing is equal across a broad range of axon calibers (R. Shi, R. B. Borgens, *J. Neurocytology* 29, 633-643 (2000)).

We hypothesized this inhibition of leakage of the nerve fiber membrane reduces the opportunity for secondary axotomy to occur. This is consistent with the observation that PEG-treated cords are more intact, possess greater amounts of intact white matter, and a reduced lesion volume than in untreated guinea pig spinal cord as shown by quantitative comparison of three dimensional reconstructions of these spinal cords (B. S. Duerstock, R. B. Borgens, *J. Exp. Biol.* 205, 13 (2002)).

In summary, intravenous and topical administration of a hydrophilic polymer in clinical cases of acute neurologically complete spinal cord injury in dogs results in an unexpected, rapid recovery of multiple measures of functional outcome. Such a rapid and complete clinical recovery is not observed in response to conventional clinical/surgical management of neurologically complete injuries, including the administration of steroids, and decompressive surgery (J. R. Coats et. al., *Veterinary Surgery* 24, 128-139 (1995)).

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. In addition, all references cited herein are indicative of the level of skill in the art and are hereby incorporated by reference in their entirety.

What is claimed is:

1. A method for treating an injury to nerve tissue of a mammalian patient, the method comprising administering an effective amount of a composition comprising polyethylene glycol to the patient so that the polyethylene glycol is delivered via the patient's vascular system to the site of the injured nerve tissue and wherein the polyethylene glycol is about 15% to about 50% by weight in the composition.

2. The method of claim 1, wherein said polyethylene glycol is in a pharmaceutically acceptable carrier.

3. The method of claim 2, wherein said carrier is water.

4. The method of claim 1, wherein delivery by way of the patient's vascular system is effected by intravascular injection.

5. The method of claim 4, wherein the intravascular injection comprises an intravenous injection.

6. The method of claim 1, wherein delivery by way of the patient's vascular system is effected by intramuscular injection.

7. The method of claim 1, wherein delivery by way of the patient's vascular system is effected by subcutaneous injection.

8. The method of claim 1, wherein delivery by way of the patient's vascular system is effected by intraperitoneal injection.

9. The method of claim 1, wherein the injured nerve tissue is spinal cord tissue.

10. The method of claim 1, wherein the injured nerve tissue is peripheral nerve tissue.

11. The method of claim 1, wherein the injury comprises a mechanical injury.

12. The method of claim 1, wherein the injury comprises a biochemical injury.

13. The method of claim 1, wherein the injury comprises an ischemic injury.

14. The method of claim 1, wherein the wherein the polyethylene glycol is at least 30% by weight in the composition.

* * * * *